(12) United States Patent
Glenn, Jr. et al.

(10) Patent No.: US 7,276,089 B2
(45) Date of Patent: Oct. 2, 2007

(54) KERATIN DYEING COMPOUNDS, KERATIN DYEING COMPOSITIONS CONTAINING THEM, AND USE THEREOF

(75) Inventors: Robert Wayne Glenn, Jr., Virginia Water (GB); Mu'Ill Lim, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 225 days.

(21) Appl. No.: 11/210,045

(22) Filed: Aug. 23, 2005

(65) Prior Publication Data
US 2006/0042025 A1 Mar. 2, 2006

Related U.S. Application Data

(60) Provisional application No. 60/604,650, filed on Aug. 26, 2004.

(51) Int. Cl.
A61K 7/13 (2006.01)
(52) U.S. Cl. .................. 8/405; 8/406; 8/408; 8/409; 8/570; 8/571; 8/574; 8/575; 8/576; 549/311
(58) Field of Classification Search .............. 8/405, 8/406, 408, 409, 570, 571, 574, 575, 476; 549/311
See application file for complete search history.

(56) References Cited

U.S. PATENT DOCUMENTS

| | | | |
|---|---|---|---|
| 2,281,583 A | 5/1942 | Kranzlcin | |
| 3,804,823 A | 4/1974 | Fisher et al. | |
| 4,013,404 A | 3/1977 | Parent et al. | |
| 4,301,071 A | 11/1981 | Giles et al. | |
| 4,354,970 A | 10/1982 | Fleischer et al. | |
| 4,396,392 A | 8/1983 | Konrad et al. | |
| 4,396,710 A | 8/1983 | Bergthaller | |
| 4,567,272 A | 1/1986 | Orth et al. | |
| 4,843,153 A | 6/1989 | Ellingsfeld et al. | |
| 5,019,130 A | 5/1991 | Flood | |
| 5,120,637 A | 6/1992 | Furusawa et al. | |
| 5,306,815 A | 4/1994 | Hahn et al. | |
| 5,578,087 A | 11/1996 | Audousset et al. | |
| 5,616,150 A | 4/1997 | Moeller et al. | |
| 5,980,585 A | 11/1999 | Terranova et al. | |
| 6,022,379 A | 2/2000 | Genard et al. | |
| 6,027,538 A | 2/2000 | Vandenbossche | |
| 6,139,589 A * | 10/2000 | Vidal et al. ............ | 8/409 |
| 6,248,137 B1 | 6/2001 | Terranova et al. | |
| 6,391,064 B1 | 5/2002 | Baudry et al. | |
| 6,395,042 B1 | 5/2002 | Andoosset | |
| 6,730,789 B1 | 5/2004 | Birault et al. | |
| 6,774,244 B2 | 8/2004 | Lim et al. | |
| 6,884,265 B2 | 4/2005 | Vidal | |
| 2002/0032935 A1 | 3/2002 | Ohashi | |
| 2002/0170124 A1 | 11/2002 | Lim et al. | |
| 2004/0040098 A1 | 3/2004 | Lang | |
| 2004/0093676 A1 | 5/2004 | Laurent | |
| 2004/0133992 A1 | 7/2004 | Herve | |
| 2004/0187229 A1 | 9/2004 | Guerin | |
| 2004/0194231 A1 | 10/2004 | Guerin | |
| 2004/0216247 A1 | 11/2004 | Guerin | |
| 2005/0060815 A1 | 3/2005 | Kravtchenko | |
| 2005/0193502 A1 | 9/2005 | Murphy | |
| 2005/0193504 A1 | 9/2005 | Glenn | |
| 2005/0198745 A1 | 9/2005 | Murphy | |

FOREIGN PATENT DOCUMENTS

| | | |
|---|---|---|
| DE | 2715680 A1 | 10/1978 |
| DE | 2719179 A1 | 11/1978 |
| DE | 3804221 A1 | 3/1989 |
| DE | 3731395 A1 | 4/1989 |
| DE | 19856342 A1 | 8/2000 |
| DE | 10025672 | 11/2001 |
| EP | 1040818 | 10/2000 |
| EP | 1386603 A | 2/2004 |
| FR | 2845283 A | 4/2004 |
| GB | 1 546 575 A | 5/1979 |
| GB | 2337530 A | 11/1999 |
| JP | 57040559 A | 3/1982 |
| JP | 63045282 A2 | 2/1988 |
| JP | 3258713 A2 | 11/1991 |
| JP | 06130603 A | 5/1994 |
| WO | WO 02/09661 A1 | 2/2002 |
| WO | WO-02/058657 A1 | 8/2002 |
| WO | WO-03/030848 A1 | 9/2002 |

OTHER PUBLICATIONS

STIC Search Report dated on May 23, 2007.*
Lion, C., et al., "Reaction of 2,5-dimethylpyrroles with Quinones. Synthesis of New Pyrrolylquinones Dyes", J. of Heterocyclic Chemistry, Hetero Corp., Tampa, FL., US, vol. 39, pp. 125-130 (Jan.-Feb. 2002).
XP-002335822, Chemical Abstracts Service, Columbus, OH, Sudiyama, N., "2- Phenylcoumarone Derivatives. III. Synthesis of a New Dye, Dicoumarone Red I and 2,3- diarylcoumaronoquinone" (Apr. 22, 2001).

(Continued)

Primary Examiner—Eisa Elhilo
(74) Attorney, Agent, or Firm—Melissa Krasovec; Marianne Dressman; Tara M. Rosnell

(57) ABSTRACT

Compositions for the oxidative dyeing of keratin fibers, comprising a medium suitable for dyeing and at least one bicyclic fused 5-5-membered aza heteroaromatic keratin dyeing compound with an N-hydroxy or N-amino group and derivatives thereof. A method for oxidative dyeing of keratin fibers, comprising applying such compositions in the presence of an oxidizing agent, for a period sufficient to develop the desired coloration.

23 Claims, No Drawings

OTHER PUBLICATIONS

XP-002335823, Chemical Abstracts Service, Columbus, OH, Greenlalgh, C.W., et al., "The Benzofuranone Chromogen and Its Application to Disperse Dyes" (Nov. 8, 1994).

XP-002335824, Chemical Abstracts Service, Columbus, OH, Sessler, J.L., et al., "Method for the Preparation of cyclo[n]pyrroles Via An Oxidative Coupling Procedure" Sep. 5, 2003).

XP-002335825, Chemical Abstracts Service, Columbus, OH, Dann, O., et al., "Polynuclear Thiophenes. IV. Thioopheno ['2',3', 5,6]thianaphthene" (Apr. 22, 2001).

Kyziol, J.B.; Lyzniak, A., "2-Aminocarbazole Synthesis", *Tetrahedron*, vol. 36, No. 20-21, 1980, pp. 3017-3019, XP002349627, Pergamon Press, UK.

* cited by examiner

KERATIN DYEING COMPOUNDS, KERATIN DYEING COMPOSITIONS CONTAINING THEM, AND USE THEREOF

FIELD OF INVENTION

This invention relates to bicyclic fused 5-5-membered aza heteroaromatic keratin dyeing compounds with an N-hydroxy or N-amino group and derivatives thereof and compositions for the oxidative dyeing of keratin fibers (preferably hair) comprising such compounds, and use thereof.

BACKGROUND OF THE INVENTION

The most extensively used method currently employed to color hair is by an oxidative process that utilizes one or more oxidative hair coloring agents in combination with one or more oxidizing agents.

Commonly, a peroxy oxidizing agent is used in combination with one or more developers or couplers, generally small molecules capable of diffusing into hair. In this procedure, a peroxide material, such as hydrogen peroxide, activates the developers so that they react with the couplers to form larger sized compounds in the hair shaft to give a variety of shades and colors.

A wide variety of developers and couplers have been employed in such oxidative hair coloring systems and compositions. However, there still exists a need for additional keratin dyeing compounds that can act as both developers and couplers that safely provide color benefits.

SUMMARY OF THE INVENTION

This invention relates to bicyclic fused 5-5-membered aza heteroaromatic keratin dyeing compounds with an N-hydroxy or N-amino group and derivatives thereof according to the formulas defined herein. This invention also relates to a composition for the oxidative dyeing of keratin fibers, comprising a medium suitable for dyeing and bicyclic fused 5-5-membered aza heteroaromatic keratin dyeing compounds with an N-hydroxy or N-amino group and derivatives thereof. This invention further relates to a method for oxidative dyeing of keratin fibers, comprising applying such compositions in the presence of an oxidizing agent, for a period sufficient to develop the desired coloration. The keratin dyeing compounds of the present invention can act as a developer and/or a coupler.

It is to be understood that within the scope of this invention, numerous potentially and actually tautomeric compounds are involved. Thus, for example, 2-mercaptopyridine (I) exists under known conditions in the pyridine-2-thione tautomer form (II).

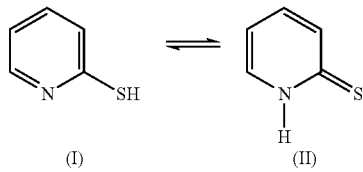

(I)    (II)

It is to be understood that when this development refers to a particular structure, all of the reasonable additional tautomeric structures are included. In the art, tautomeric structures are frequently represented by one single structure and the present invention follows this general practice.

DETAILED DESCRIPTION OF THE INVENTION

While the specification concludes with claims that particularly point out and distinctly claim the invention, it is believed the present invention will be better understood from the following description.

The present invention relates to bicyclic fused 5-5-membered aza heteroaromatic keratin dyeing compounds with an N-hydroxy or N-amino group and derivatives thereof. The compounds of the present invention can act as developers and/or couplers that safely provide color benefits.

Herein, "comprising" means that other steps and other ingredients which do not affect the end result can be added. This term encompasses the terms "consisting of" and "consisting essentially of". The compounds/compositions and methods/processes of the present invention can comprise, consist of, and consist essentially of the essential elements and limitations of the invention described herein, as well as any of the additional or optional ingredients, components, steps, or limitations described herein.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

Except as otherwise noted, all amounts including part, percentages, and proportions are understood to be modified by the word "about", and amounts are not intended to indicate significant digits. Except as otherwise noted, the articles "a", "an", and "the" mean "one or more".

As used herein, the term "keratin" refers to a scleroprotein found in epidermal tissues and modified into hard structures such as horns, hair, and nails. Thus, "keratinous fibers" refers to those found in hair, skin and nails and various animal body parts such as horns, hooves and feathers.

As used herein, the term "hair" refers to keratinous fibers on a living, e.g. a person, or non-living body, e.g. in a wig, hairpiece, or other aggregation of non-living keratinous fibers. Mammalian, preferably human, hair is a preferred. Notably, hair, wool, fur, and other keratinous fibers are suitable substrates for coloring by the compounds and compositions described herein.

As used herein, the term "keratin dyeing compounds" refers to compounds that may be used in the composition to act as developers, couplers, or both, in order to provide color to ketatinous fibers.

As used herein, the term "keratin dyeing composition" refers to the composition containing one or more keratin dyeing compounds, including the compounds described herein.

As used herein, "cosmetically acceptable" means that ingredients which the term describes are suitable for use in contact with the skin or hair of humans and lower animals without undue toxicity, incompatibility, instability, irritation, allergic response, and the like.

I. Keratin Dyeing Compounds

The inventive compounds are bicyclic fused 5-5-membered aza heteroaromatic keratin dyeing compounds with an N-hydroxy or N-amino group and derivatives thereof, according to the following formulas:

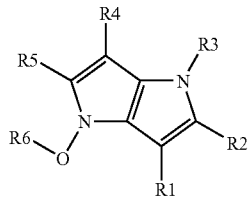

I

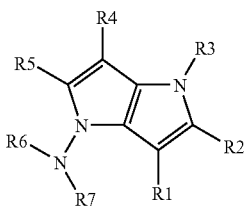

II

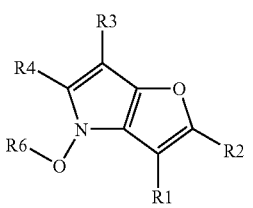

III

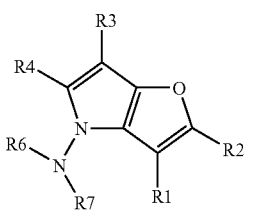

IV

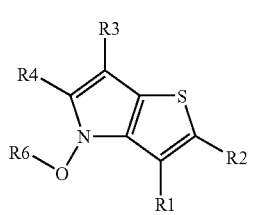

V

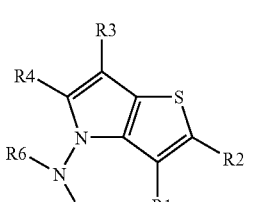

VI

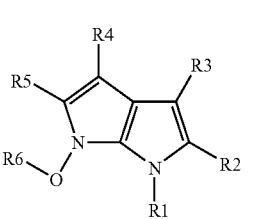

VII

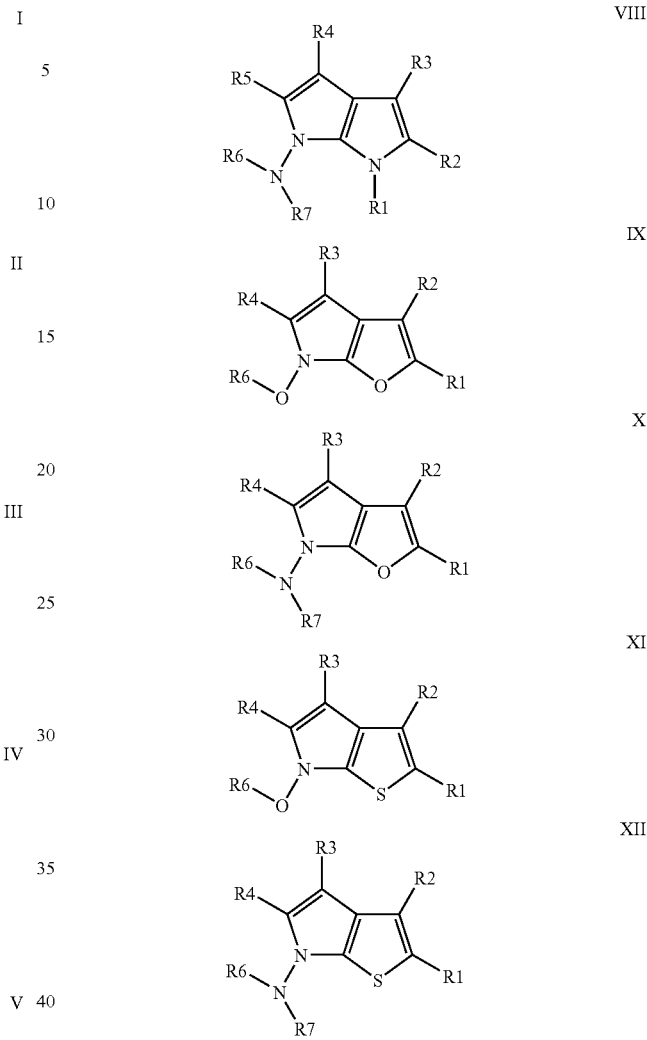

wherein R1, R2, R3, R4, R5, R6, and R7 are the same or different and are selected from the group consisting of:
(a) C-linked monovalent substituents selected from the group consisting of:
(i) substituted or unsubstituted, straight or branched, alkyl, mono- or poly-unsaturated alkyl, heteroalkyl, aliphatic, heteroaliphatic, or heteroolefinic systems,
(ii) substituted or unsubstituted, mono- or poly-cyclic aliphatic, aryl, or heterocyclic systems, and
(iii) substituted or unsubstituted, mono-, poly-, or perfluoro alkyl systems;
wherein said systems of (i), (ii) and (iii) comprise from about 1 to about 10 carbon atoms and from about 0 to about 5 heteroatoms selected from the group consisting of O, S, N, P, and Si;
wherein substituents of the substituted systems of the C-linked monovalent substituents are selected from the group consisting of amino, hydroxyl, alkylamino (linear, branched, or cyclic C1-C5), dialkylamino (linear, branched, or cyclic C1-C5), hydroxyalkylamino (linear, branched, or cyclic C1-C5), dihydroxyalkylamino (linear, branched, or cyclic C1-C5), arylamino or substituted arylamino (substituents are halogen, C1-C5 alkyl, C1-C5 alkoxy, trifluoromethyl, amino, C1-C5 alkylamino), heteroarylamino or substituted heteroarylamino (substituents are halogen, C1-C5 alkyl, C1-C5 alkoxy, trifluoromethyl, amino, C1-C5 alkylamino), arylmethylamino or substituted arylmethylamino (substituents are halogen, C1-C5 alkyl, C1-C5 alkoxy, trifluoromethyl, amino, C1-C5 alkylamino), and heteroarylmethylamino or substituted heteroarylmethylamino (substituents are halogen, C1-C5 alkyl, C1-C5 alkoxy, trifluoromethyl, amino, C1-C5 alkylamino).

(b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;

(c) O-linked monovalent substituents selected from the group consisting of $OA^1$, and $ONA^1A^2$;

(d) N-linked monovalent substituents selected from the group consisting of $NA^1A^2$, $(NA^1A^2A^3)^+$, $NA^1OA^2$, $NA^1SA^2$, $NO_2$, $N=NA^1$, $N=NOA^1$, $NA^1CN$, and $NA^1NA^2A^3$;

(e) monovalent substituents selected from the group consisting of $COOA^1$, $CONA^1_2$, $CONA^1COA^2$, $C(=NA^1)NA^1A^2$, $CN$, and $X$; and (f) fluoroalkyl monovalent substituents selected from the group consisting of mono-, poly-, and per-fluoro alkyl systems comprising from about 1 to about 12 carbon atoms and from about 0 to about 4 heteroatoms;

(g) hydrogen;

wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, or per-fluoro alkyl systems, or $A^1$ and $A^2$ together with nitrogen atoms to which they are bound form a ring; wherein said systems comprise from about 1 to about 10 carbon atoms and from about 0 to about 5 heteroatoms selected from the group consisting of O, S, N, P, and Si;

wherein X is a halogen selected from the group consisting of F, Cl, Br, and I.

In a preferred embodiment, $R^1$, $R^2$, $R^3$, $R^4$, $R^5$, $R^6$, and $R^7$ are selected from the group consisting of a hydrogen atom; a halogen atom such as chlorine, bromine or fluorine; an amino substituent, a hydroxyl substituent; a cyano substituent; a $C_1$-$C_4$ alkyl substituent; a trifluoromethyl substituent, an alkylamino substituent (e.g., N,N-dimethylamino, N,N-diethylamino, N-methylamino, or N-ethylamino); a hydroxyalkylamino substituent (e.g., N-(hydroxyethyl) amino, N-hydroxymethylamino, N-hydroxypropylamino, N,N-bis(hydroxyethyl)amino, N-(2,3-dihydroxypropyl) amino or N,N-bis(hydroxypropyl)amino); an acetylamido substituent; a carboxyl substituent or its esters; an alkoxy substituent (e.g., methoxy, ethoxy, propyloxy, benzyloxy, methoxyethoxy, phenoxyethoxy, 2-cyanoethoxy, phenethyloxy, phenoxyethoxy, p-chlorobenzyloxy or methoxyethylcarbamoylmethoxy); an alkoxyalkyl substituent (e.g., methoxymethyl, methoxyethyl, methoxypropyl, ethoxymethyl, ethoxyethyl or ethoxypropyl); a carbamoyl substituent; an alkylcarbamoyl substituent (e.g., methylcarbamoyl, ethylcarbamoyl, dimethylcarbamoyl, or diethylcarbamoyl); a hydroxyalkylcarbamoyl substituent (e.g., 2-hydroxyethylcarbamoyl, bis(2-hydroxyethyl)carbamoyl, hydroxymethylcarbamoyl, bis(hydroxymethyl)carbamoyl); an amido substituent; an alkylamido substituent (e.g., acetamido, propionamido, or butyramido); an alkylcarbonyl substituent (e.g., acetyl, butyryl, or propionyl), an alkoxycarbonyl substituent (e.g., methoxycarbonyl, ethoxycarbonyl, or propoxycarbonyl); an aryloxy substituent (e.g., phenoxy, 4-methoxyphenoxy, 4-nitrophenoxy, 4-cyanophenoxy, 4-methanesulfonamidophenoxy, 4-methanesulfonylphenoxy, 3-methylphenoxy or 1-naphthyloxy); an acyloxy substituent (e.g., acetoxy, propanoyloxy, benzolyloxy, 2,4-dichlorobenzolyloxy, ethoxyalkyloxy, pyruviloyloxy, cinnamoyloxy or myristoyloxy); an alkylthio substituent (e.g., methylthio, ethylthio, propylthio, butylthio, 2-cyanoethylthio, benzylthio, phenethylthio, 2-(diethylamino)ethylthio, ethoxyethylthio or phenoxyethylthio); an arylthio substituent (e.g., phenylthio, 4-carboxyphenylthio, 2-ethoxy-5-tert-butylphenylthio, 2-carboxyphenylthio or 4-methanesulfonylphenylthio); a heteroarylthio substituent (e.g., 5-phenyl-2,3,4,5-tetrazolyloxy or 2-benzothiazolyloxy); a heteroaryloxy substituent (e.g., 5-phenyl-2,3,4,5-tetrazolyloxy or 2-benzothiazolyloxy); a 3-, 4-, 5-, 6-, or 7-membered heterocycle having at least one nitrogen, oxygen or sulfur atom (e.g., pyridyl, quinolyl, morpholyl, furyl, tetrahydrofuryl, pyrazolyl, triazolyl, tetrazolyl, oxazolyl, imidazolyl, thiadiazolyl, pyrollidine, piperidine, morpholine, piperazine, indoline, hexahydroazepine, aziridine, and azetidine) and being optionally substituted; an aryl substituent (e.g., phenyl or naphthyl) which is optionally substituted; a sulfonyl substituent; a sulfinyl substituent; a phosphonyl substituent; a sulfamoyl substituent; a siloxy substituent; an acyloxy substituent; a carbamoyloxy substituent; a sulphonamide substituent; an imide substituent; a ureido substituent; a sulfamoylamino substituent; an alkoxycarbonylamino substituent; an aryloxycarbonylamino substituent; an aryloxycarbonyl substituent; and a benzenesulfonamido substituent.

If the compound of the present invention is utilized as a developer, at least one of $R^1$, $R^2$, $R^3$, and $R^4$ is an amino group. Preferably, at least one of the remaining $R^1$, $R^2$, $R^3$, and $R^4$ substituents are selected from substituents selected from the group consisting of amino, hydroxyl, a 3-, 4-, 5-, 6-, or 7-membered heterocycle having at least one nitrogen, oxygen or sulfur atom (e.g., pyridyl, quinolyl, morpholyl, furyl, tetrahydrofuryl, pyrazolyl, triazolyl, tetrazolyl, oxazolyl, imidazolyl, thiadiazolyl, pyrollidine, piperidine, morpholine, piperazine, indoline, hexahydroazepine, aziridine, and azetidine) and being optionally substituted, alkylamino (linear, branched, or cyclic C1-C5), dialkylamino (linear, branched, or cyclic C1-C5), hydroxyalkylamino (linear, branched, or cyclic C1-C5), dihydroxyalkylamino (linear, branched, or cyclic C1-C5), arylamino or substituted arylamino (substituents are halogen, C1-C5 alkyl, C1-C5 alkoxy, trifluoromethyl, amino, C1-C5 alkylamino), heteroarylamino or substituted heteroarylamino (substituents are halogen, C1-C5 alkyl, C1-C5 alkoxy, trifluoromethyl, amino, C1-C5 alkylamino), arylmethylamino or substituted arylmethylamino (substituents are halogen, C1-C5 alkyl, C1-C5 alkoxy, trifluoromethyl, amino, C1-C5 alkylamino), and heteroarylmethylamino or substituted heteroarylmethylamino (substituents are halogen, C1-C5 alkyl, C1-C5 alkoxy, trifluoromethyl, amino, C1-C5 alkylamino).

If the compound of the present invention is utilized as a coupler, at least one of $R^1$, $R^2$, $R^3$, and $R^4$ is selected from substituents selected from the group consisting of Amino, Hydroxyl, Alkylamino (linear, branched, or cyclic C1-C5), Hydroxyalkylamino (linear, branched, or cyclic C1-C5), Arylamino or substituted arylamino (substituents are halogen, C1-C5 alkyl, C1-C5 alkoxy, trifluoromethyl, amino, C1-C5 alkylamino), Heteroarylamino or substituted heteroarylamino (substituents are halogen, C1-C5 alkyl, C1-C5 alkoxy, trifluoromethyl, amino, C1-C5 alkylamino), Arylmethylamino or substituted arylmethylamino (substituents are halogen, C1-C5 alkyl, C1-C5 alkoxy, trifluoromethyl, amino, C1-C5 alkylamino), and Heteroarylmethylamino or substituted heteroarylmethylamino (substituents are halogen, C1-C5 alkyl, C1-C5 alkoxy, trifluoromethyl, amino, C1-C5 alkylamino).

The developers and couplers of the present invention can also accommodate nucleofugic leaving groups selected from the group consisting of hydrogen, chlorine, cyano, alkoxy, phenoxy, methylsulfonyoxy, pyridone and pyridazone.

In a preferred embodiment, the couplers of the present invention are utilized in compositions together with suitable 5-membered ring developers chosen from the following classes: thiophenes, pyrroles, furans, pyrazoles, imidazoles, thiazoles, oxazoles, isothiazoles, or isoxazoles. In a more preferred embodiment, the couplers of the present invention are utilized in compositions together with pyrazoles. In an even more preferred embodiment, the couplers of the present invention are utilized in compositions together with the following pyrazoles: 1-methyl-1H-pyrazole-4,5-diamine, 2-(4,5-diamino-1H-pyrazol-1-yl)ethanol, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5-diamine and 1-Hydroxyethyl-4,5-diaminopyrazole sulphate. Even more preferably, the couplers of the present invention are utilized in compositions together with 1-methyl-1H-pyrazole-4,5-diamine; 1-Hydroxyethyl-4,5-diaminopyrazole sulphate; and 2-(4,5-diamino-1H-pyrazol-1-yl)ethanol. While not being bound to theory, such combinations enable the achievement of desired more hypsochromic colors (e.g., yellow) relative to conventional combinations of developers and couplers.

Preferred developers and couplers are selected from the group consisting of pyrrolo[3,2-b]pyrrole, furo[3,2-b]pyrrole, thieno[3,2-b]pyrrole, pyrrolo[2,3-b]pyrrole, furo[2,3-b]pyrrole, and thieno[2,3-b]pyrrole. Preferred developers and couplers include the following bicyclic fused 5-5-membered aza heteroaromatic keratin dyeing compounds with an N-hydroxy or N-amino group and derivatives thereof.

A. Pyrrolo[3,2-b]pyrrole

1. Preferred Developers

Preferred Pyrrolo[3,2-b]pyrrole developers are selected from the group consisting of 2,5-Diamino-4H-pyrrolo[3,2-b]pyrrol-1-ol, 2,5-diamino-4-methyl-4H-pyrrolo[3,2-b]pyrrol-1-ol, 1-methoxy-4-methyl-1,4-dihydro-pyrrolo[3,2-b]pyrrole-2,5-diamine, 1-ethoxy-4-methyl-1,4-dihydro-pyrrolo[3,2-b]pyrrole-2,5-diamine, 2-(2,5-diamino-4-methyl-4H-pyrrolo[3,2-b]pyrrol-1-yloxy)-ethanol, 2-(5-amino-2-ethylamino-4-methyl-4H-pyrrolo[3,2-b]pyrrol-1-yloxy)-ethanol, 2-[5-amino-2-(2-hydroxy-ethylamino)-4-methyl-4H-pyrrolo[3,2-b]pyrrol-1-yloxy]-ethanol, 2-{5-amino-2-[bis-(2-hydroxy-ethyl)-amino]-4-methyl-4H-pyrrolo[3,2-b]pyrrol-1-yloxy}-ethanol, 2-(5-amino-4-methyl-2-pyrrolidin-1-yl-4H-pyrrolo[3,2-b]pyrrol-1-yloxy)-ethanol, 2-amino-4-methyl-5-methylamino-4H-pyrrolo[3,2-b]pyrrol-1-ol, N5-ethyl-1-methoxy-4-methyl-1,4-dihydro-pyrrolo[3,2-b]pyrrole-2,5-diaamine, 2-[(5-amino-4-methoxy-1-methyl-1,4-dihydro-pyrrolo[3,2-b]pyrrol-2-yl)-(2-hydroxy-ethyl)-amino]-ethanol, 2-[(5-amino-4-methoxy-1-methyl-1,4-dihydro-pyrrolo[3,2-b]pyrrol-2-yl)-(2-hydroxy-ethyl)-amino]-ethanol, 2-amino-4H-pyrrolo[3,2-b]pyrrole-1,5-diol, 2-amino-4-methyl-4H-pyrrolo[3,2-b]pyrrole-1,5-diol, 5-amino-4-methoxy-1-methyl-1,4-dihydro-pyrrolo[3,2-b]pyrrol-2-ol, 5-amino-1-ethoxy-4-ethyl-1,4-dihydro-pyrrolo[3,2-b]pyrrol-2-ol, 5-amino-1-(2-hydroxy-ethoxy)-4-methyl-1,4-dihydro-pyrrolo[3,2-b]pyrrol-2-ol, 5-amino-4-(2-hydroxy-ethoxy)-1-methyl-1,4-dihydro-pyrrolo[3,2-b]pyrrol-2-ol, 4,5-diamino-1,4-dihydro-pyrrolo[3,2-b]pyrrol-2-ol, 4,5-diamino-1-methyl-1,4-dihydro-pyrrolo[3,2-b]pyrrol-2-ol, 5-amino-1-methyl-4-methylamino-1,4-dihydro-pyrrolo[3,2-b]pyrrol-2-ol, 5-amino-4-ethyl-1-ethylamino-1,4-dihydro-pyrrolo[3,2-b]pyrrol-2-ol, 5-amino-1-(2-hydroxy-ethylamino)-4-methyl-1,4-dihydro-pyrrolo[3,2-b]pyrrol-2-ol, 5-amino-4-(2-hydroxy-ethylamino)-1-methyl-1,4-dihydro-pyrrolo[3,2-b]pyrrol-2-ol, 5-amino-4-dimethylamino-1,4-dihydro-pyrrolo[3,2-b]pyrrol-2-ol, 5-amino-4-[bis-(2-hydroxy-ethyl)-amino]-1-methyl-1,4-dihydro-pyrrolo[3,2-b]pyrrol-2-ol, 4H-pyrrolo[3,2-b]pyrrole-1,2,5-triamine, 4-methyl-4H-pyrrolo[3,2-b]pyrrole-1,2,5-triamine, 4, N1-dimethyl-4H-pyrrolo[3,2-b]pyrrole-1,2,5-triamine, N1-ethyl-4-methyl-4H-pyrrolo[3,2-b]pyrrole-1,2,5-triamine, 2-(2,5-diamino-4-methyl-4H-pyrrolo[3,2-b]pyrrol-1-ylamino)-ethanol, 2-(5-amino-2-ethylamino-4-methyl-4H-pyrrolo[3,2-b]pyrrol-1-ylamino)-ethanol, 2-[5-amino-2-(2-hydroxy-ethylamino)-4-methyl-4H-pyrrolo[3,2-b]pyrrol-1-ylamino]-ethanol, 2-{5-amino-2-[bis-(2-hydroxy-ethyl)-amino]-4-methyl-4H-pyrrolo[3,2-b]pyrrol-1-ylamino}-ethanol, 2-(5-amino-4-methyl-2-pyrrolidin-1-yl-4H-pyrrolo[3,2-b]pyrrol-1-ylamino)-ethanol, 4N5-dimethyl-4H-pyrrolo[3,2-b]pyrrole-1,2,5-triamine, N5-ethyl-4,N1-dimethyl-4H-pyrrolo[3,2-b]pyrrole-1,2,5-triamine, 2-[(5-amino-1-methyl-4-methylamino-1,4-dihydro-pyrrolo[3,2-b]pyrrol-2-yl)-(2-hydroxy-ethyl)-amino]-ethanol, 2-(2-amino-4-methyl-5-pyrrolidin-1-yl-4H-pyrrolo[3,2-b]pyrrol-1-ylamino)-ethanol, 4N1,N1-trimethyl-4H-pyrrolo[3,2-b]pyrrole-1,2,5-triamine, N1,N1-Diethyl-4-methyl-4H-pyrrolo[3,2-b]pyrrole-1,2,5-triamine, 2-[(2,5-diamino-4-methyl-4H-pyrrolo[3,2-b]pyrrol-1-yl)-(2-hydroxy-ethyl)-amino]-ethanol, 1-methyl-4-pyrrolidin-1-yl-1,4-dihydro-pyrrolo[3,2-b]pyrrole-2,5-diamine, 2-[(5-amino-4-2-pyrrolidin-1-yl-4H-pyrrolo[3,2-b]pyrrol-1-yl)-(2-hydroxy-ethyl)-amino]-ethanol, and 2-[(2-amino-4-methyl-5-pyrrolidin-1-yl-4H-pyrrolo[3,2-b]pyrrol-1-yl)-methyl-amino]-ethanol.

Especially preferred developers are selected from the group consisting of 2,5-Diamino-4H-pyrrolo[3,2-b]pyrrol-1-ol, 2,5diamino-4-methyl-4H-pyrrolo[3,2-b]pyrrol-1-ol, 1-methoxy-4-methyl-1,4-dihydro-pyrrolo[3,2-b]pyrrole-2,5-diamine, 1-ethoxy-4-methyl-1,4-dihydro-pyrrolo[3,2-b]pyrrole-2,5-diamine, 2-(2,5-diamino-4-methyl-4H-pyrrolo[3,2-b]pyrrol-1-yloxy)-ethanol, 2-(5-amino-2-ethylamino-4-methyl-4H-pyrrolo[3,2-b]pyrrol-1-yloxy)-ethanol, 4, N1-dimethyl-4H-pyrrolo[3,2-b]pyrrole-1,2,5-triamine, N1-ethyl-4-methyl-4H-pyrrolo[3,2-b]pyrrole-1,2,5-triamine, 2-(2,5-diamino-4-methyl-4H-pyrrolo[3,2-b]pyrrol-1-ylamino)-ethanol, 2-(5-amino-2-ethylamino-4-methyl-4H-pyrrolo[3,2-b]pyrrol-1-ylamino)-ethanol, 2-[5-amino-2-(2-hydroxy-ethylamino)-4-methyl-4H-pyrrolo[3,2-b]pyrrol-1-ylamino]-ethanol, 2-{5-amino-2-[bis-(2-hydroxy-ethyl)-amino]-4-methyl-4H-pyrrolo[3,2-b]pyrrol-1-ylamino}-ethanol, 2-(5-amino-4-methyl-2-pyrrolidin-1-yl-4H-pyrrolo[3,2-b]pyrrol-1-ylamino)-ethanol, 4N5-dimethyl-4H-pyrrolo[3,2-b]pyrrole-1,2,5-triamine, N5-ethyl-4,N1-dimethyl-4H-pyrrolo[3,2-b]pyrrole-1,2,5-triamine, 2-[(5-amino-1-methyl-4-methylamino-1,4-dihydro-pyrrolo[3,2-b]pyrrol-2-yl)-(2-hydroxy-ethyl)-amino]-ethanol, 2-(2-amino-4-methyl-5-pyrrolidin-1-yl-4H-pyrrolo[3,2-b]pyrrol-1-ylamino)-ethanol, 4N1,N1-trimethyl-4H-pyrrolo[3,2-b]pyrrole-1,2,5-triamine, N1,N1-diethyl-4-methyl-4H-pyrrolo[3,2-b]pyrrole-1,2,5-triamine, 2-[(2,5-diamino-4-methyl-4H-pyrrolo[3,2-b]pyrrol-1-yl)-(2-hydroxy-ethyl)-amino]-ethanol, 1-methyl-4-pyrrolidin-1-yl-1,4-dihydro-pyrrolo[3,2-b]pyrrole-2,5-diamine, 2-[(5-amino-4-methyl-2-pyrrolidin-1-yl-4H-pyrrolo[3,2-b]pyrrol-1-yl)-(2-hydroxyethyl)-amino]-ethanol, and 2-[(2-amino-4-methyl-5-pyrrolidin-1-yl-4H-pyrrolo[3,2-b]pyrrol-1-yl)-methyl-amino]-ethanol.

2. Preferred Couplers

Preferred Pyrrolo[3,2-b]pyrrole couplers are selected from the group consisting of 4H-Pyrrolo[3,2-b]pyrrol-1-ol, 1-methoxy-1,4-dihydro-pyrrolo[3,2-b]pyrrole, 1-ethoxy-1,4-dihydro-pyrrolo[3,2-b]pyrrole, 2-(4H-pyrrolo[3,2-b]pyrrol-1-yloxy)-ethanol, 1-isopropoxy-1,4-dihydro-pyrrolo[3,2-b]pyrrole, 4H-pyrrolo[3,2-b]pyrrole-1,2-diol, 1-methoxy-4-methyl-1,4-dihydro-pyrrolo[3,2-b]pyrrol-2-ol, 4H-pyrrolo[3,2-b]pyrrole-1,5-diol, 4-methyl-4H-pyrrolo[3,2-pyrrole-1,5-diol, 4-methoxy-1,4-dihydro-pyrrolo[3,2-b]pyrrol-2-ol, 4-methoxy-1-methyl-1,4-dihydro-pyrrolo[3,2-b]pyrrol-2-ol, 4-methyl-4H-pyrrolo[3,2-b]pyrrole-1,6-diol, 4-methoxy-1-methyl-1,4-dihydro-pyrrolo[3,2-b]pyrrol-3-ol, 4H-pyrrolo[3,2-b]pyrrole-1,3-diol, 1-methoxy-4-methyl-1,4-dihydro-pyrrolo[3,2-b]pyrrol-3-ol, 3-amino-4H-pyrrolo[3,2-b]pyrrol-1-ol, 1-methoxy-4-methyl-1,4-dihydro-pyrrolo[3,2-b]pyrrol-3-ylamine, 6-amino-4H-pyrrolo[3,2-b]pyrrol-1-ol, 4-methyl-1-methyl-1,4-dihydro-pyrrolo[3,2-b]pyrrol-3-ylamine, 5-amino-4H-pyrrolo[3,2-]pyrrol-1-ol, 4-methoxy-1-methyl-1,4-dihydro-pyrrolo[3,2-b]pyrrol-2-ylamine, 4H-pyrrolo[3,2-b]pyrrol-1-ylamine, methyl-(4H-pyrrolo[3,2-b]pyrrol-1-yl)-amine, ethyl-(4H-pyrrolo[3,2-b]pyrrol-1-yl)-amine, 2-(4H-pyrrolo[3,2-b]pyrrol-1-ylamino)-ethanol, isopropyl-(4H-pyrrolo[3,2-b]pyrrol-1yl)-amine, 1-amino-1,4-dihydro-pyrrolo[3,2-b]pyrrol-2-ol, 1-diethylamino-4-methyl-1,4-dihydro-pyrrolo-[3,2-b]pyrrol-2-ol, 1-[bis-(2-hydroxy-ethyl)-amino]-4-methyl-1,4-dihydro-pyrrolo[3,2-b]pyrrol-2-ol, 4-diethylamino-1,4-dihydro-pyrrolo[3,2-b]pyrrol-2-ol, 4-amino-1-methyl-1,4-dihydro-pyrrolo[3,2-b]pyrrol-2-ol, 4-diethylamino-1,4-dihydro-pyrrolo[3,2-b]pyrrol-2-ol, 4-[bis-(2-hydroxy-ethyl)-amino]-1-methyl-1,4-dihydro-pyrrolo[3,2-b]pyrrol-2-ol, 4-amino-1-methyl-1,4-dihydro-pyrrolo[3,2-b]pyrrol-3-ol, 4-diethylamino-1-methyl-1,4-dihydro-pyrrolo[3,2-b]pyrrol-3-ol, 1-diethylamino-1,4-dihydro-pyrrolo[3,2-b]pyrrol-3-ol, 1-[bis-(2-hydroxy-ethyl)-amino]-4-methyl-1,4-dihydro-pyrrolo[3,2-b]pyrrol-3-ol, 4H-pyrrolo[3,2-b]pyrrole-1,2-diamine, N1,N1-diethyl-4-methyl-4H-pyrrolo[3,2-b]pyrrole-1,2-diamine, 4H-pyrrolo[3,2-b]pyrrole-1,3-diamine, N1,N1-diethyl-4-methyl-4H-pyrrolo[3,2-b]pyrrole-1,3-diamine, 4H-pyrrolo[3,2-b]pyrrole-1,6-diamine, 4N1-dimethyl-4H-pyrrolo[3,2-b]pyrrole-1,6-diamine, 4H-pyrrolo[3,2-b]pyrrole-1,5-diamine, and 4N1-dimethyl-4H-pyrrolo[3,2-b]pyrrole-1,5-diamine.

Especially preferred couplers are selected from the group consisting of 4H-pyrrolo[3,2-b]pyrrol-1-ol, 1-methoxy-1,4-dihydro-pyrrolo[3,2-b]pyrrole, 1-ethoxy-1,4-dihydro-pyrrolo[3,2-b]pyrrole, 2-(4H-pyrrolo[3,2-b]pyrrol-1-yloxy)-ethanol, 1-isopropoxy-1,4-dihydro-pyrrolo[3,2-b]pyrrole, 4H-pyrrolo[3,2-b]pyrrole-1,2-diol, 1-methoxy-4-methyl-1,4-dihydro-pyrrolo[3,2-b]pyrrol-2-ol, 4H-pyrrolo[3,2-b]pyrrole-1,5-diol, 4-methyl-4H-pyrrolo[3,2-b]pyrrole-1,5-diol, 4-methoxy-1,4-dihydro-pyrrolo[3,2-b]pyrrol-2-ol, 4-methoxy-1-methyl-1,4-dihydro-pyrrolo[3,2-b]pyrrol-2-ol, 4-methyl-4H-pyrrolo[3,2-b]pyrrole-1,6-diol, 4-methoxy-1-methyl-1,4-dihydro-pyrrolo[3,2-b]pyrrol-3-ol, 4H-pyrrolo[3,2-b]pyrrole-1,3-diol, 1-methoxy-4-methyl-1,4-dihydro-pyrrolo[3,2-b]pyrrol-3-ol, 3-amino-4H-pyrrolo[3,2-b]pyrrol-1-ol, 1-methoxy-4-methyl-1,4-dihydro-pyrrolo[3,2-b]pyrrol-3-ylamine, 6-amino-4H-pyrrolo[3,2-b]pyrrol-1-ol, 4-methoxy-1-methyl-1,4-dihydro-pyrrolo[3,2-b]pyrrol-3-ylamine, 5-amino-4H-pyrrolo[3,2-]pyrrol-1-ol, and 4-methoxy-1-methyl-1,4-dihydro-pyrrolo[3,2-b]pyrrol-2-ylamine.

B. Furo[3,2-b]pyrrole

1. Preferred Developers

Preferred furo[3,2-b]pyrrole developers are selected from the group consisting of 2,5-Diamino-furo[3,2-b]pyrrol-4-ol, 2,5-diamino-furo[3,2-b]pyrrol-4-ol, 4-methoxy-4H-furo[3,2-b]pyrrole-2,5-diamine, 4-ethoxy-4H-furo[3,2-b]pyrrole-2,5-diamine, 2-(2,5-diamino-furo[3,2-b]pyrrol-4-yloxy)-ethanol, 2-(2-amino-5-ethylamino-furo[3,2-b]pyrrol-4-yloxy)-ethanol, 2-[2-amino-5-(2-hydroxy-ethylamino)-furo[3,2-b]pyrrol-4-yloxy]-ethanol, 2-{2-amino-5-[bis-(2-hydroxy-ethyl)-amino]-furo[3,2-b]pyrrol-4-yloxy}-ethanol, 2-(2-amino-5-pyrrolidin-1-yl-furo[3,2-b]pyrrol-4-yloxy)-ethanol, 5-amino-2-methylamino-furo[3,2-b]pyrrol-4-ol, N2-ethyl-4-methoxy-4H-furo[3,2-b]pyrrole-2,5-diamine, 2-[(5-amino-4-methoxy-4H-furo[3,2-b]pyrrol-2-yl)-(2-hydroxy-ethyl)-amino]-ethanol, 2-(5-amino-2-pyrrolidin-1-yl-furo[3,2-b]pyrrol-4-yloxy)-ethanol, furo[3,2-b]pyrrole-2,4,5-triamine, N4-methyl-furo[3,2-b]pyrrole-2,4,5-triamine, N4-ethyl-furo[3,2-b]pyrrole-2,4,5-triamine, 2-(2,5-diamino-furo[3,2-b]pyrrol-4-ylamino)-ethanol, 2-(2-amino-5-ethylamino-furo[3,2-b]pyrrol-4-ylamino)-ethanol, 2-[2-amino-5-(2-hydroxy-ethylamino)-furo[3,2-b]pyrrol-4-ylamino]-ethanol, 2-{2-amino-5-[bis-(2-hydroxy-ethyl)-amino]-furo[3,2-b]pyrrol-4-ylamino}-ethanol, 2-(2-amino-5-pyrrolidin-1-yl-furo[3,2-b]pyrrol-4-ylamino)-ethanol, 2-[(2-Amino-5-pyrrolidin-1-yl-furo[3,2-b]pyrrol-4-yl)-hydroxyethyl-amino]-ethanol, N2-methyl-furo[3,2-b]pyrrole-2,4,5-triamine, N2-ethyl-N4-methyl-furo[3,2-b]pyrrole-2,4,5-triamine, 2-[(5-amino-4-pyrrolidin-1-yl-4H-furo[3,2-b]pyrrol-2-yl)-(2-hydroxy-ethyl)-amino]-ethanol, 2-[(5-amino-2-pyrrolidin-1-yl-furo[3,2-b]pyrrol-4-yl)-methyl-amino]-ethanol, 2-[(5-amino-2-pyrrolidin-1-yl-furo[3,2-b]pyrrol-4-yl)-(2-hydroxy-ethyl)-amino]-ethanol, 5-amino-furo[3,2-b]pyrrole-2,4-diol, 5-amino-furo[3,2-b]pyrrole-2,4-diol, 5-amino-4-methoxy-4H-furo[3,2-b]pyrrol-2-ol, 2-amino-4-ethoxy-4H-furo[3,2-b]pyrrol-5-ol, 2-amino-4-(2-hydroxy-ethoxy-4H-furo[3,2-b]pyrrol-5-ol, 5-amino-4-(2-hydroxy-ethoxy)-4H-furo[3,2-b]pyrrol-2-ol, 4,5-diamino-4H-furo[3,2-b]pyrrol-2-ol, 2,4-diamino-4H-furo[3,2-b]pyrrol-5-ol, 5-amino-4-methylamino-4H-furo[3,2-b]pyrrol-2-ol, 2-amino-4-ethylamino-4H-furo[3,2-b]pyrrol-5-ol, 2-amino-4-(2-hydroxy-ethylamino)-4H-furo[3,2-b]pyrrol-5-ol, 5-amino-4-(2-hydroxy-ethylamino)-4H-furo[3,2-b]pyrrol-2-ol, 5-amino-4-morpholin-4-yl-4H-furo[3,2-b]pyrrol-2-ol, 5-amino-4-dimethylamino-4H-furo[3,2-b]pyrrol-2-ol, 5-amino-4-[bis-(2-hydroxy-ethyl)-amino]-4H-furo[3,2-b]pyrrol-2-ol, and 2-amino-4-[bis-(2-hydroxy-ethyl)-amino]-4H-furo[3,2-b]pyrrol-5-ol.

Especially preferred developers are selected from the group consisting of 2,5-diamino-furo[3,2-b]pyrrol-4-ol, 2,5-diamino-furo[3,2-b]pyrrol-4-ol, 4-methoxy-4H-furo[3,2-b]pyrrole-2,5-diamine, 4-ethoxy-4H-furo[3,2-b]pyrrole-2,5-diamine, 2-(2,5-diamino-furo[3,2-b]pyrrol-4-yloxy)-ethanol, 2-(2-amino-5-ethylamino-furo[3,2-b]pyrrol-4-yloxy)-ethanol, 2-[2-amino-5-(2-hydroxy-ethylamino)-furo[3,2-b]pyrrol-4-yloxy]-ethanol, 2-{2-amino-5-[bis-(2-hydroxy-ethyl)-amino]-furo[3,2-b]pyrrol-4-yloxy}-ethanol, 2-(2-amino-5-pyrrolidin-1-yl-furo[3,2-b]pyrrol-4-yloxy)-ethanol, 5-amino-2-methylamino-furo[3,2-b]pyrrol-4-ol, N2-ethyl-4-methoxy-4H-furo[3,2-b]pyrrole-2,5-diamine, 2-[(5-amino-4-methoxy-4H-furo[3,2-b]pyrrol-2-yl)-(2-hydroxy-ethyl)-amino]-ethanol, 2-(5-amino-2-pyrrolidin-1-yl-furo[3,2-b]pyrrol-4-yloxy)-ethanol, furo[3,2-b]pyrrole-2,4,5-triamine, N4-methyl-furo[3,2-b]pyrrole-2,4,5-triamine, N4-ethyl-furo[3,2-b]pyrrole-2,4,5-triamine, 2-(2,5-diamino-furo[3,2-b]pyrrol-4-ylamino)-ethanol, 2-(2-amino-5-ethylamino-furo[3,2-b]pyrrol-4-ylamino)-ethanol, 2-[2-amino- 5-(2-hydroxy-ethylamino)-furo[3,2-b]pyrrol-4-ylamino]-ethanol, 2-{2-amino-5-[bis-(2-hydroxy-ethyl)-amino]-furo[3,2-b]pyrrol-4-ylamino}-ethanol, 2-(2-amino-5-pyrrolidin-1-yl-furo[3,2-b]pyrrol-4-ylamino)-ethanol, 2-[(2-Amino-5-pyrrolidin-1-yl-furo[3,2-b]pyrrol-4-yl)-hydroxyethyl-amino]-ethanol, N2-methyl-furo[3,2-b]pyrrole-2,4,5-triamine, N2-ethyl-N4-methyl-furo[3,2-b]pyrrole-2,4,5-triamine, 2-[(5-amino-4-pyrrolidin-1-yl-4H-furo[3,2-b]pyrrol-2-yl)-(2-hydroxy-ethyl)-amino]-ethanol, 2-[(5-amino-2-pyrrolidin-1-yl-furo[3,2-b]pyrrol-4-yl)-methyl-amino]-ethanol, and 2-[(5-amino-2-pyrrolidin-1-yl-furo[3,2-b]pyrrol-4-yl)-(2-hydroxy-ethyl)-amino]-ethanol.

2. Preferred Couplers

Preferred furo[3,2-b]pyrrole couplers are selected from the group consisting of Furo[3,2-b]pyrrole4,5-diol, 4-methoxy-4H-furo[3,2-b]pyrrol-5-ol, furo[3,2-b]pyrrole4,6-diol, 4-methoxy-4H-furo[3,2-b]pyrrol-6-ol, furo[3,2-b]pyrrole-2,4-diol, 4-methoxy-4H-furo[3,2-b]pyrrol-2ol, 4-ethoxy-4H-furo[3,2-b]pyrrol-2-ol, furo[3,2-b]pyrrole-3,4-diol, 4-methoxy-4H-furo[3,2-b]pyrrol-3-ol, 5-amino-furo[3,2-b]pyrrol-4-ol, 4-ethoxy-4H-furo[3,2-b]pyrrol-5-ylamine, 6-amino-furo[3,2-b]pyrrol-4-ol, 4-methoxy-4H-furo[3,2-b]pyrrol-6-ylamine, 2-amino-furo[3,2-b]pyrrol-4-ol, 4-methoxy-4H-furo[3,2-b]pyrrol-2-ylamine, 3-amino-furo[3,2-b]pyrrol-4-ol, 4-methoxy-4H-furo[3,2-b]pyrrol-3-ylamine, 4-amino-4H-furo[3,2-b]pyrrol-5-ol, 4-methylamino-4H-furo[3,2-b]pyrrol-5-ol, 4-diethylamino-4H-furo[3,2-b]pyrrol-5-ol, 4-amino-4H-furo[3,2-b]pyrrol-6-ol, 4-methylamino-4H-furo[3,2-b]pyrrol-6-ol, 4-diethylamino-4H-furo[3,2-b]pyrrol-6-ol, 4-amino-4H-furo[3,2-b]pyrrol-2-ol, 4-methylamino-4H-furo[3,2-b]pyrrol-2-ol, 4-methylamino-4H-furo[3,2-b]pyrrol-2-ol, 4-amino-4H-furo[3,2-b]pyrrol-3-ol, 4-ethylamino-4H-furo[3,2-b]pyrrol-3ol, 4-diethylamino-4H-furo[3,2-b]pyrrol-3-ol, furo[3,2-b]pyrrole-4,5-diamine, N4-ethyl-furo[3,2-b]pyrrole-4,5-diamine, N4,N4-diethyl-furo[3,2-b]pyrrole-4,6-diamine, furo[3,2-b]pyrrole-4,6-diamine, N4-ethyl-furo[3,2-b]pyrrole-4,6-diamine, N4,N4-diethyl-furo[3,2-b]pyrrole-4,6-diamine, furo[3,2-b]pyrrole-2,4-diamine, N4-ethyl-furo[3,2-b]pyrrole-2,4-diamine, N4,N4-diethyl-furo[3,2-b]pyrrole-2,4-diamine, furo[3,2-b]pyrrole-3,4-diamine, N4-ethyl-furo[3,2-b]pyrrole-3,4-diamine, and N4,N4-diethyl-furo[3,2-b]pyrrole-3,4-diamine.

Especially preferred couplers are selected from the group consisting of furo[3,2-b]pyrrole-4,5diol, 4-methoxy-4H-furo[3,2-b]pyrrol-5-ol, furo[3,2-b]pyrrole-4,6-diol, 4-methoxy-4H-furo[3,2-b]pyrrol-6-ol, furo[3,2-b]pyrrole-2,4-diol, 4-methoxy-4H-furo[3,2-b]pyrrol-2ol, 4-ethoxy-4H-furo[3,2-b]pyrrol-2-ol, 4-amino-4H-furo[3,2-b]pyrrol-5-ol, 4-methylamino-4H-furo[3,2-b]pyrrol-5-ol, 4-diethylamino-4H-furo[3,2-b]pyrrol-5-ol, 4-amino-4H-furo[3,2-b]pyrrol-6-ol, 4-methylamino4H-furo[3,2-b]pyrrol-6-ol, and 4-diethylamino-4H-furo[3,2-b]pyrrol-6-ol.

C. Thieno[3,2-b]pyrrole

1. Preferred Developers

Preferred thieno[3,2-b]pyrrole developers are selected from the group consisting of 2,5-Diamino-thieno[3,2-b]pyrrol-4-ol, 2,5-diamino-thieno[3,2-b]pyrrol-4-ol, 4-methoxy-4H-thieno[3,2-b]pyrrole-2,5-diamine, 4-ethoxy-4H-thieno[3,2-b]pyrrole-2,5-diamine, 2-(2,5-diamino-thieno[3,2-b]pyrrol-4-yloxy)-ethanol, 2-(2-amino-5-ethylamino-thieno[3,2-b]pyrrol-4-yloxy)-ethanol, 2-[2-amino-5-(2-hydroxy-ethylamino)-thieno[3,2-b]pyrrol-4-yloxy]-ethanol, 2-{2-amino-5-[bis-(2-hydroxy-ethyl)-amino]-thieno[3,2-b]pyrrol-4-yloxy}-ethanol, 2-(2-amino-5-pyrrolidin-1-yl-thieno[3,2-b]pyrrol-4-yloxy)-ethanol, 5-amino-2-methylamino-thieno[3,2-b]pyrrol-4-ol, N2-ethyl-4-methoxy-4H-thieno[3,2-b]pyrrole-2,5-diamine, 2-[(5-amino-4-methoxy-4H-thieno[3,2-b]pyrrol-2-yl)-(2-hydroxy-ethyl)-amino]-ethanol, 2-(5-amino-2-pyrrolidin-1-yl-thieno[3,2-b]pyrrol-4-yloxy)-ethanol, thieno[3,2-b]pyrrole-2,4,5-triamine, N4-methyl-thieno[3,2-b]pyrrole-2,4,5-triamine, N4-ethyl-thieno[3,2-b]pyrrole-2,4,5-triamine, 2-(2,5-diamino-thieno[3,2-b]pyrrol-4-ylamino)-ethanol, 2-(2-amino-5-ethylamino-thieno[3,2-b]pyrrol-4-ylamino)-ethanol, 2-[2-amino-5-(2-hydroxy-ethylamino)-thieno[3,2-b]pyrrol-4-ylamino]-ethanol, 2-{2-amino-5-[bis-(2-hydroxy-ethyl)-amino]-thieno[3,2-b]pyrrol-4-ylamino}-ethanol, 2-(2-amino-5-pyrrolidin-1-yl-thieno[3,2-b]pyrrol-4-ylamino)-ethanol, 2-[(2-amino-5-pyrrolidin-1-yl-thieno[3,2-b]pyrrol-4-yl)-(2-hydroxy-ethyl)-amino]-ethanol, N2-methyl-thieno[3,2-b]pyrrole-2,4,5-triamine, N2-ethyl-N4-methyl-thieno[3,2-b]pyrrole-2,4,5-triamine, 2-[(5-amino-4-pyrrolidin-1-yl-4H-thieno[3,2-b]pyrrol-2-yl)-(2-hydroxy-ethyl)-amino]-ethanol, 2-[(5-amino-2-pyrrolidin-1-yl-thieno[3,2-b]pyrrol-4-yl)-methyl-amino]-ethanol, 2-[(5-amino-2-pyrrolidin-1-yl-thieno[3,2-b]pyrrol-4-yl)-(2-hydroxy-ethyl)-amino]-ethanol, 5-amino-thieno[3,2-b]pyrrole-2,4-diol, 5-amino-thieno[3,2-b]pyrrole-2,4-diol, 5-amino-4-methoxy-4H-thieno[3,2-b]pyrrol-2-ol, 2-amino-4-ethoxy-4H -thieno[3,2-b]pyrrol-5-ol, 2-amino-4-(2-hydroxy-ethoxy)-4H-thieno[3,2-b]pyrrol-5-ol, 5-amino-4-(2-hydroxy-ethoxy)-4H-thieno[3,2-b]pyrrol-2-ol, 4,5-diamino-4H-thieno[3,2-b]pyrrol-2-ol, 2,4-diamino-4H-thieno[3,2-b]pyrrol-5-ol, 5-amino-4-methylamino-4H-thieno[3,2-b]pyrrol-2-ol, 2-amino-4-ethylamino-4H-thieno[3,2-b]pyrrol-5-ol, 2-amino-4-(2-hydroxy-ethylamino)-4H-thieno[3,2-b]pyrrol-5-ol, 5-amino-4-(2-hydroxy-ethylamino)-4H-thieno[3,2-b]pyrrol-2-ol, 5-amino-4-morpholin-4-yl-4H-thieno[3,2-b]pyrrol-2-ol, 5-amino-4-dimethylamino-4H-thieno[3,2-b]pyrrol-2-ol, 5-amino-4-[bis-(2-hydroxy-ethyl)-amino]-4H-thieno[3,2-b]pyrrol-2-ol, and 2-amino-4-[bis-(2-hydroxy-ethyl)-amino]-4H-thieno[3,2-b]pyrrol-5-ol.

Especially preferred developers are selected from the group consisting of 2,5-diamino-thieno[3,2-b]pyrrol-4-ol, 2,5-diamino-thieno[3,2-b]pyrrol-4-ol, 4-methoxy-4H-thieno[3,2-b]pyrrole-2,5-diamine, 4-ethoxy-4H-thieno[3,2-b]pyrrole-2,5-diamine, 2-(2,5-diamino-thieno[3,2-b]pyrrol-4-yloxy)-ethanol, 2-(2-amino-5-ethylamino-thieno[3,2-b]pyrrol-4-yloxy)-ethanol, 2-[2-amino-5-(2-hydroxy-ethylamino)-thieno[3,2-b]pyrrol-4-yloxy]-ethanol, 2-{2-amino-5-[bis-(2-hydroxy-ethyl)-amino]-thieno[3,2-b]pyrrol-4-yloxy}-ethanol, 2-(2-amino-5-pyrrolidin-1-yl-thieno[3,2-b]pyrrol-4-yloxy)-ethanol, 5-amino-2-methylamino-thieno[3,2-b]pyrrol-4-ol, N2-ethyl-4-methoxy-4H-thieno[3,2-b]pyrrole-2,5-diaamine, 2-[(5-amino-4-methoxy-4H-thieno[3,2-b]pyrrol-2-yl)-(2-hydroxy-ethyl)-amino]-ethanol, 2-(5-amino-2-pyrrolidin-1-yl-thieno[3,2-b]b]pyrrol-4-yloxy)-ethanol, thieno[3,2-b]pyrrole-2,4,5-triamine, N4-methyl-thieno[3,2-b]pyrrole-2,4,5-triamine, N4-ethyl-thieno[3,2-b]pyrrole-2,4,5-triamine, 2-(2,5-diamino-thieno[3,2-b]pyrrole-4-ylamino)-ethanol, 2-(2-amino-5-ethylamino-thieno[3,2-b]pyrrol-4-ylamino)-ethanol, 2-[2-amino-5-(2-hydroxy-ethylamino)-thieno[3,2-b]pyrrol-4-ylamino]-ethanol, 2-{2-amino-5-[bis-(2-hydroxy-ethyl)-amino]-thieno[3,2-b]pyrrol-4-ylamino}-ethanol, 2-(2-amino-5-pyrrolidin-1-yl-thieno[3,2-b]pyrrol-4-ylamino)-ethanol, 2-[(2-amino-5-pyrrolidin-1-yl-thieno[3,2-b]pyrrol-4-yl)-(2-hydroxy-ethyl)-amino]-ethanol, N2-methyl-thieno[3,2-b]pyrrole-2,4,5-triamine, N2-ethyl-N4-methyl-thieno[3,2-b]pyrrole-2,4,5-triamine, 2-[(5-amino-4-pyrrolidin-1-yl-4H-thieno[3,2-b]pyrrol-2-yl)-(2-hydroxy-ethyl)-amino]-ethanol, 2-[(5-amino-2-pyrrolidin-1-yl-thieno[3,2-b]pyrrol-4-yl)-methyl-amino]-ethanol, and 2-[(5-amino-2-pyrrolidin-1-yl-thieno[3,2-b]pyrrol-4-yl)-(2-hydroxy-ethyl)-amino]-ethanol.

2. Preferred Couplers

Preferred thieno[3,2-b]pyrrole couplers are selected from the group consisting of Thieno[3,2-b]pyrrole-4,5-diol, 4-methoxy-4H-thieno[3,2-b]pyrrol-5-ol, thieno[3,2-b]pyrrole-4,6-diol, 4-methoxy-4H-thieno[3,2-b]pyrrol-6-ol, thieno[3,2-b]pyrrole-2,4-diol, 4-methoxy-4H-thieno[3,2-b]pyrrol-2-ol, 4-ethoxy-4H-thieno[3,2-b]pyrrol-2-ol, thieno[3,2-b]pyrrole-3,4-diol, 4-methoxy-4H-thieno[3,2-b]pyrrol-3-ol, 5-amino-thieno[3,2-b]pyrrol-4-ol, 4-ethoxy-4H-thieno[3,2-b]pyrrol-5-ylamine, 6-amino-thieno[3,2-b]pyrrol-4-ol, 4-methoxy-4H-thieno[3,2-b]pyrrol-6-ylamine, 2-amino-thieno[3,2-b]pyrrol-4-ol, 4-methoxy-4H-thieno[3,2-b]pyrrol-2-ylamine, 3-amino-thieno[3,2-b]pyrrol-4-ol, 4-methoxy-4H-thieno[3,2-b]pyrrol-3-ylamine, 4-amino-4H-thieno[3,2-b]pyrrol-5-ol, 4-methylamino-4H-thieno[3,2-b]pyrrol-5-ol, 4-diethylamino-4H-thieno[3,2-b]pyrrol-5-ol, 4-amino-4H-thieno[3,2-b]pyrrol-6-ol, 4-methylamino-4H-thieno[3,2-b]pyrrol-6-ol, 4-diethylamino-4H-thieno[3,2-b]pyrrol-6-ol, 4-amino-4H-thieno[3,2-b]pyrrol-2-ol, 4-methylamino-4H-thieno[3,2-b]pyrrol-2-ol, 4-diethylamino-4H-thieno[3,2-b]pyrrol-2-ol, 4-amino-4H-thieno[3,2-b]pyrrol-3-ol, 4-ethylamino-4H-thieno[3,2-b]pyrrol-3-ol, 4-diethylamino-4H-thieno[3,2-b]pyrrol-3-ol, thieno[3,2-b]pyrrole-4,5-diamine, N4-ethyl-thieno[3,2-b]pyrrole-4,5-diamine, N4,N4-diethyl-thieno[3,2-b]pyrrole-4,6-diamine, thieno[3,2-b]pyrrole-4,6-diamine, N4-ethyl-thieno[3,2-b]pyrrole-4,6-diamine, N4,N4-diethyl-thieno[3,2-b]pyrrole-4,6-diamine, thieno[3,2-b]pyrrole-2,4-diamine, N4-ethyl-thieno[3,2-b]pyrrole-2,4-diamine, N4,N4-diethyl-furo[3,2-b]pyrrole-2,4-diamine, thieno[3,2-b]pyrrole-3,4-diamine, N4-ethyl-thieno[3,2-b]pyrrole-3,4-diamine, N4,N4-diethyl-thieno[3,2-b]pyrrole-3,4-diamine, and thieno[3,2-b]pyrrole-2,4-diamine.

Especially preferred couplers are selected from the group consisting of thieno[3,2-b]pyrrole-4,5-diol, 4-methoxy-4H-thieno[3,2-b]pyrrol-5-ol, thieno[3,2-b]pyrrole-4,6-diol, 4-methoxy-4H-thieno[3,2-b]pyrrol-6-ol, 4-amino-4H-thieno[3,2-b]pyrrol-5-ol, 4-methylamino-4H-thieno[3,2-b]pyrrol-5-ol, 4-diethylamino-4H-thieno[3,2-b]pyrrol-5-ol, 4-amino-4H-thieno[3,2-b]pyrrol-6-ol, 4-methylamino-4H-thieno[3,2-b]pyrrol-6-ol, and 4-diethylamino-4H-thieno[3,2-b]pyrrol-6-ol.

D. Pyrrolo[2,3-b]pyrrole
1. Preferred Developers

Preferred pyrrolo[2,3-b]pyrrole developers are selected from the group consisting of 2,3-Diamino-6H-pyrrolo[2,3-b]pyrrol-1-ol, 1-methoxy-1,6-dihydro-pyrrolo[2,3-b]pyrrole-2,3-diamine, 1-ethoxy-1,6-dihydro-pyrrolo[2,3-b]pyrrole-2,3-diamine, 2-(2,3-diamino-6H-pyrrolo[2,3-b]pyrrol-1-yloxy)-ethanol, 1-isopropoxy-1,6-dihydro-pyrrolo[2,3-b]pyrrole-2,3-diamine, 1-benzyloxy-1,6-dihydro-pyrrolo[2,3-b]pyrrole-2,3-diamine, 2,3-diamino-6-methyl-6H-pyrrolo[2,3-b]pyrrol-1-ol, 6-ethyl-1-methoxy-1,6-dihydro-pyrrolo[2,3-b]pyrrole-2,3-diamine, 2-(4,5-diamino-6-methoxy-6H-pyrrolo[2,3-b]pyrrol-1-yl)-ethanol, 2-(4,5-diamino-6-methoxy-6H-pyrrolo[2,3-b]pyrrol-1-yl)-ethanol, 6-benzyl-1-methoxy-1,6-dihydro-pyrrolo[2,3-b]pyrrole-2,3-diamine, 2-amino-6-methyl-6H-pyrrolo[2,3-b]pyrrole-1,3-diol, 2-amino-6-isopropyl-6H-pyrrolo[2,3-b]pyrrole-1,3-diol, 4,5-diamino-6-methyl-6H-pyrrolo[2,3-b]pyrrol-1-ol, 6-methoxy-1-methyl-1,6-dihydro-pyrrolo[2,3-b]pyrrole-2,3-diamine, 5-amino-6-methyl-6H-pyrrolo[2,3-b]pyrrole-1,4-diol, 6H-pyrrolo[2,3-b]pyrrole-1,2,3-triamine, N1-methyl-6H-pyrrolo[2,3-b]pyrrole-1,2,3-triamine, N1-ethyl-6H-pyrrolo[2,3-b]pyrrole-1,2,3-triamine, 2-(2,3-diamino-6H-pyrrolo[2,3-b]pyrrol-1-ylamino)-ethanol, N1-isopropyl-6H-pyrrolo[2,3-b]pyrrole-1,2,3-triamine, N1-benzyl-6H-pyrrolo[2,3-b]pyrrole-1,2,3-triamine, 6-methyl-6H-pyrrolo[2,3-b]pyrrole-1,2,3-triamine, 6-ethyl-N1-methyl-6H-pyrrolo[2,3-b]pyrrole-1,2,3-triamine, 2-(4,5-diamino-6-methylamino-6H-pyrrolo[2,3-b]pyrrol-1-yl)-ethanol, 2-(4,5-diamino-6-methylamino-6H-pyrrolo[2,3-b]pyrrol-1-yl)-ethanol, 6-benzyl-N1-methyl-6H-pyrrolo[2,3-b]pyrrole-1,2,3-triamine, 1,2-diamino-6-methyl-1,6-dihydro-pyrrolo[2,3-b]pyrrol-3-ol, 2-amino-6-isopropyl-1-methylamino-1,6-dihydro-pyrrolo[2,3-b]pyrrol-3-ol, 6N1,N1-trimethyl-6H-pyrrolo[2,3-b]pyrrole-1,4,5-triamine, 6N1-dimethyl-6H-pyrrolo[2,3-b]pyrrole-1,4,5-triamine, 2-amino-6-dimethylamino-1-methyl-1,6-dihydro-pyrrolo[2,3-b]pyrrol-3-ol, N1,N1-dimethyl-6H-pyrrolo[2,3-b]pyrrole-1,2,3-triamine, 2-[(2,3-diamino-6H-pyrrolo[2,3-b]pyrrol-1-yl)-(2-hydroxy-ethyl)-amino]-ethanol, 1-pyrrolidin-1-yl-1,6-dihydro-pyrrolo[2,3-b]pyrrole-2,3-diamine, and 2-(4,5-diamino-6-dimethylamino-6H-pyrrolo[2,3-b]pyrrol-1-yl)-ethanol.

Especially preferred developers are selected from the group consisting of 2,3-diamino-6H-pyrrolo[2,3-b]pyrrol-1-ol, 1-methoxy-1,6-dihydro-pyrrolo[2,3-b]pyrrole-2,3-diamine, 1-ethoxy-1,6-dihydro-pyrrolo[2,3-b]pyrrole-2,3-diamine, 2-(2,3-diamino-6H-pyrrolo[2,3-b]pyrrol-1-yloxy)-ethanol, 1-isopropoxy-1,6-dihydro-pyrrolo[2,3-b]pyrrole-2,3-diamine, 1-benzyloxy-1,6-dihydro-pyrrolo[2,3-b]pyrrole-2,3-diamine, 6H-pyrrolo[2,3-b]pyrrole-1,2,3-triamine, N1-methyl-6H-pyrrolo[2,3-b]pyrrole-1,2,3-triamine, N1-ethyl-6H-pyrrolo[2,3-b]pyrrole-1,2,3-triamine, 2-(2,3-diamino-6H-pyrrolo[2,3-b]pyrrol-1-ylamino)-ethanol, N1-isopropyl-6H-pyrrolo[2,3-b]pyrrole-1,2,3-triamine, and N1-benzyl-6H-pyrrolo[2,3-b]pyrrole-1,2,3-triamine.

2. Preferred Couplers

Preferred pyrrolo[2,3-b]pyrrole couplers are selected from the group consisting of 3-Amino-6H-pyrrolo[2,3-b]pyrrol-1-ol, 1-methoxy-1,6-dihydro-pyrrolo[2,3-b]pyrrol-3-ylamine, 1-ethoxy-1,6-dihydro-pyrrolo[2,3-b]pyrrol-3-ylamine, 2-(3-amino-6H-pyrrolo[2,3-b]pyrrol-1-yloxy)-ethanol, 1-isopropoxy-1,6-dihydro-pyrrolo[2,3-b]pyrrol-3-ylamine, 1-benzyloxy-1,6-dihydro-pyrrolo[2,3-b]pyrrol-3-ylamine, 4-amino-6-methyl-6H-pyrrolo[2,3-b]pyrrol-1-ol, 1-ethyl-6-methoxy-1,6-dihydro-pyrrolo[2,3-b]pyrrol-3-ylamine, 2-(3-amino-6-methoxy-6H-pyrrolo[2,3-b]pyrrol-1-yl)-ethanol, 1-benzyl-6-methoxy-1,6-dihydro-pyrrolo[2,3-b]pyrrol-3-ylamine, 6-methyl-6H-pyrrolo[2,3-b]pyrrole-1,3-diol, 1-ethoxy-6-isopropyl-1,6-dihydro-pyrrolo[2,3-b]pyrrol-3-ol, 6-methyl-6H-pyrrolo[2,3-b]pyrrole-1,4-diol, 6-methoxy-1-methyl-1,6-dihydro-pyrrolo[2,3-b]pyrrol-3-ol, 6-benzyloxy-1-methyl-1,6-dihydro-pyrrolo[2,3-b]pyrrol-3-ol, 6H-Pyrrolo[2,3-b]pyrrole-1,3-diamine, N1-methyl-6H-pyrrolo[2,3-b]pyrrole-1,3-diamine, N1,N1-diethyl-6H-pyrrolo[2,3-b]pyrrole-1,3-diamine, 2-[(3-amino-6H-pyrrolo[2,3-b]pyrrol-1-yl)-(2-hydroxy-ethyl)-amino]-ethanol, N1-isopropyl-6H-pyrrolo[2,3-b]pyrrole-1,3-diamine, N1-benzyl-6H-pyrrolo[2,3-b]pyrrole-1,3-diamine, 6-methyl-6H-pyrrolo[2,3-b]pyrrole-1,4-diamine, 6N1,N1-triethyl-6H-pyrrolo[2,3-b]pyrrole-1,4-diamine, 2-(3-amino-6-methylamino-6H-pyrrolo[2,3-b]pyrrol-1-yl)-ethanol, 6-benzyl-N1-methyl-6H-pyrrolo[2,3-b]pyrrole-1,4-diamine, 1-amino-6-methyl-1,6-dihydro-pyrrolo[2,3-b]pyrrol-3-ol, 1-diethylamino-6-isopropyl-1,6-dihydro-pyrrolo[2,3-b]pyrrol-3-ol, 6-amino-1-methyl-1,6-dihydro-pyrrolo[2,3-b]pyrrol-3-ol, 6-diethylamino-1-methyl-1,6-dihydro-pyrrolo[2,3-b]pyrrol-3-ol, and 6-benzylamino-1-methyl-1,6-dihydro-pyrrolo[2,3-b]pyrrol-3-ol.

Especially preferred couplers are selected from the group consisting of 6H-pyrrolo[2,3-b]pyrrole-1,3-diamine, N1-methyl-6H-pyrrolo[2,3-b]pyrrole-1,3-diamine, N1,N1-diethyl-6H-pyrrolo[2,3-b]pyrrole-1,3-diamine, 2-[(3-amino-6H-pyrrolo[2,3-b]pyrrol-1-yl)-(2-hydroxy-ethyl)-amino]-ethanol, N1-isopropyl-6H-pyrrolo[2,3-b]pyrrole-1,3-diamine, N1-benzyl-6H-pyrrolo[2,3-b]pyrrole-1,3-diamine, 6-methyl-6H-pyrrolo[2,3-b]pyrrole-1,4-diamine, 6N1,N1-triethyl-6H-pyrrolo[2,3-b]pyrrole-1,4-diamine, 2-(3-amino-6-methylamino-6H-pyrrolo[2,3-b]pyrrol-1-yl)-ethanol, 6-benzyl-N1-methyl-6H-pyrrolo[2,3-b]pyrrole-1,4-diamine, 1-amino-6-methyl-1,6-dihydro-pyrrolo[2,3-b]pyrrol-3-ol, 1-diethylamino-6-isopropyl-1,6-dihydro-pyrrolo[2,3-b]pyrrol-3-ol, 6-amino-1-methyl-1,6-dihydro-pyrrolo[2,3-b]pyrrol-3-ol, 6-diethylamino-1-methyl-1,6-dihydro-pyrrolo[2,3-b]pyrrol-3-ol, and 6-benzylamino-1-methyl-1,6-dihydro-pyrrolo[2,3-b]pyrrol-3-ol.

E. Furo[2,3-b]pyrrole

1. Preferred Developers

Preferred furo[2,3-b]pyrrole developers are selected from the group consisting of 4,5-Diamino-furo[2,3-b]pyrrol-6-ol, 6-methoxy-6H-furo[2,3-b]pyrrole-4,5-diamine, 6-ethoxy-6H-furo[2,3-b]pyrrole-4,5-diamine, 2-(4,5-diamino-furo[2,3-b]pyrrol-6-yloxy)-ethanol, 6-isopropoxy-6H-furo[2,3-b]pyrrole-4,5-diamine, 6-benzyloxy-6H-furo[2,3-b]pyrrole-4,5-diamine, 5-amino-furo[2,3-b]pyrrole-4,6-diol, 5-amino-6-methoxy-6H-furo[2,3-b]pyrrol-4-ol, 6-methoxy-6H-furo[2,3-b]pyrrole-2,3-diaamine, 2-amino-furo[2,3-b]pyrrole-3,6-diol, 2-amino-6-methoxy-6H-furo[2,3-b]pyrrol-3-ol, furo[2,3-b]pyrrole-4,5,6-triamine, N6-methyl-furo[2,3-b]pyrrole-4,5,6-triamine, N6-ethyl-furo[2,3-b]pyrrole-4,5,6-triamine, 2-(4,5-diamino-furo[2,3-b]pyrrol-6-ylamino)-ethanol, N6-isopropyl-furo[2,3-b]pyrrole-4,5,6-triamine, N6-benzyl-furo[2,3-b]pyrrole-4,5,6-triamine, N6,N6-dimethyl-furo[2,3-b]pyrrole-4,5,6-triamine, 2-[(4,5-diamino-furo[2,3-b]pyrrol-6-yl)-ethyl-amino]-ethanol, 2-[(4,5-diamino-furo[2,3-b]pyrrol-6-yl)-(2-hydroxy-ethyl)-amino]-ethanol, N6-isopropyl-N6-methyl-furo[2,3-b]pyrrole-4,5,6-triamine, 5,6-diamino-6H-furo[2,3-b]pyrrol-4-ol, 5-amino-6-dimethylamino-6H-furo[2,3-b]pyrrol-4-ol, 2-[(2,3-diamino-furo[2,3-b]pyrrol-6-yl)-methyl-amino]-ethanol, N6,N6-dimethyl-furo[2,3-b]pyrrole-2,3,6-triamine, 2,6-diamino-6H-furo[2,3-b]pyrrol-3-ol, and 2-amino-6-dimethylamino-6H-furo[2,3-b]pyrrol-3-ol.

Especially preferred developers are selected from the group consisting of 4,5-diamino-furo[2,3-b]pyrrol-6-ol, 6-methoxy-6H-furo[2,3-b]pyrrole-4,5-diamine, 6-ethoxy-6H-furo[2,3-b]pyrrole-4,5-diamine, 2-(4,5-diamino-furo[2,3-b]pyrrol-6-yloxy)-ethanol, 6-isopropoxy-6H-furo[2,3-b]pyrrole-4,5-diamine, and 6-benzyloxy-6H-furo[2,3-b]pyrrole-4,5-diamine.

F. Thieno[2,3-b]pyrrole

1. Preferred Developers

Preferred thieno[2,3-b]pyrrole developers are selected from the group consisting of 4,5-Diamino-thieno[2,3-b]pyrrol-6-ol, 6-methoxy-6H-thieno[2,3-b]pyrrole-4,5-diamine, 6-ethoxy-6H-thieno[2,3-b]pyrrole-4,5-diamine, 2-(4,5-diamino-thieno[2,3-b]pyrrol-6-yloxy)-ethanol, 6-isopropoxy-6H-thieno[2,3-b]pyrrole-4,5-diamine, 6-benzyloxy-6H-thieno[2,3-b]pyrrole-4,5-diamine, 5-amino-thieno[2,3-b]pyrrole-4,6-diol, 5-amino-6-methoxy-6H-thieno[2,3-b]pyrrol-4-ol, 2,3-diamino-thieno[2,3-b]pyrrol-6-ol, 6-methoxy-6H-thieno[2,3-b]pyrrole-2,3-diamine, 2-amino-thieno[2,3-b]pyrrole-3,6-diol, 2-amino-6-methoxy-6H-thieno[2,3-b]pyrrol-3-ol, thieno[2,3-b]pyrrole-4,5,6-triamine, N6-methyl-thieno[2,3-b]pyrrole-4,5,6-triamine, N6-ethyl-thieno[2,3-b]pyrrole-4,5,6-triamine, 2-(4,5-diamino-thieno[2,3-b]pyrrol-6-ylamino)-ethanol, N6-isopropyl-thieno[2,3-b]pyrrole-4,5,6-triamine, N6-benzyl-thieno[2,3-b]pyrrole-4,5,6-triamine, N6,N6-dimethyl-thieno[2,3-b]pyrrole-4,5,6-triamine, 2-[(4,5-diamino-thieno[2,3-b]pyrrol-6-yl)-ethyl-amino]-ethanol, 2-[(4,5-diamino-thieno[2,3-b]pyrrol-6-yl)-(2-hydroxy-ethyl)-amino]-ethanol, N6-isopropyl-N6-methyl-thieno[2,3-b]pyrrole-4,5,6-triamine, 5,6-diamino-6H-thieno[2,3-b]pyrrol-4-ol, 5-amino-6-dimethylamino-6H-thieno[2,3-b]pyrrol-4-ol, thieno[2,3-b]pyrrole-2,3,6-triamine, N6-methyl-thieno[2,3-b]pyrrole-2,3,6-triamine, 2-[(2,3-diamino-thieno[2,3-b]pyrrol-6-yl)-methyl-amino]-ethanol, N6,N6-dimethyl-thieno[2,3-b]pyrrole-2,3,6-triamine, 2-[(2,3-diamino-thieno[2,3-b]pyrrol-6-yl)-(2-hydroxy-ethyl)-amino]-ethanol, 2,6-diamino-6H-thieno[2,3-b]pyrrol-3-ol, and 2-amino-6-dimethylamino-6H-thieno[2,3-b]pyrrol-3-ol. Especially preferred developers are selected from the group consisting of 4,5-diamino-thieno[2,3-b]pyrrol-6-ol, 6-methoxy-6H-thieno[2,3-b]pyrrole-4,5-diamine, 6-ethoxy-6H-thieno[2,3-b]pyrrole-4,5-diamine, 2-(4,5-diamino-thieno[2,3-b]pyrrol-6-yloxy)-ethanol, 6-isopropoxy-6H-thieno[2,3-b]pyrrole-4,5-diamine, and 6-benzyloxy-6H-thieno[2,3-b]pyrrole-4,5-diamine.

2. Preferred Couplers

Preferred thieno[2,3-b]pyrrole couplers are selected from the group consisting of 4-Amino-thieno[2,3-b]pyrrol-6-ol, 6-methoxy-6H-thieno[2,3-b]pyrrol-4-ylamine, 6-ethoxy-6H-thieno[2,3-b]pyrrol-4-ylamine, 2-(4-amino-thieno[2,3-b]pyrrol-6-yloxy)-ethanol, 6-isopropoxy-6H-thieno[2,3-b]pyrrol-4-ylamine, 6-benzyloxy-6H-thieno[2,3-b]pyrrol-4-ylamine, 3-amino-thieno[2,3-b]pyrrol-6-ol, 6-ethoxy-6H-thieno[2,3-b]pyrrol-3-ylamine, 2-(3-amino-thieno[2,3-b]pyrrol-6-yloxy)-ethanol, 6-isopropoxy-6H-thieno[2,3-b]pyrrol-3-ylamine, thieno[2,3-b]pyrrole-4,6-diol, 6-ethoxy-6H-thieno[2,3-b]pyrrol-4-ol, thieno[2,3-b]pyrrole-3,6-diol, 6-ethoxy-6H-thieno[2,3-b]pyrrol-3-ol, 6-benzyloxy-6H-thieno[2,3-b]pyrrol-3-ol, thieno[2,3-b]pyrrole-4,6-diamine, N6-methyl-thieno[2,3-b]pyrrole-4,6-diamine, N6,N6-diethyl-thieno[2,3-b]pyrrole-4,6-diamine, 2-[(4-amino-thieno[2,3-b]pyrrol-6-yl)-(2-hydroxy-ethyl)-amino]-ethanol, N6-isopropyl-thieno[2,3-b]pyrrole-4,6-diamine, N6-benzyl-thieno[2,3-b]pyrrole-4,6-diamine, thieno[2,3-b]pyrrole-3,6-diamine, N6,N6-diethyl-thieno[2,3-b]pyrrole-3,6-diamine, 2-[(3-amino-thieno[2,3-b]pyrrol-6-yl)-(2-hydroxy-ethyl)-amino]-ethanol, N6-isopropyl-thieno[2,3-b]pyrrole-3,6-diamine, 6-amino-6H-thieno[2,3-b]pyrrol-4-ol, 6-diethylamino-6H-thieno[2,3-b]pyrrol-4-ol, 6-amino-6H-thieno[2,3-b]pyrrol-3-ol, 6-diethylamino-6H-thieno[2,3-b]pyrrol-3-ol, and 6-benzylamino-6H-thieno[2,3-b]pyrrol-3-ol.

Especially preferred couplers are selected from the group consisting of 4-amino-thieno[2,3-b]pyrrol-6-ol, 6-methoxy-6H-thieno[2,3-b]pyrrol-4-ylamine, 6-ethoxy-6H-thieno[2,3-b]pyrrol-4-ylamine, 2-(4-amino-thieno[2,3-b]pyrrol-6-yloxy)-ethanol, thieno[2,3-b]pyrrole-4,6-diamine, N6-methyl-thieno[2,3-b]pyrrole-4,6-diamine, N6,N6-diethyl-thieno[2,3-b]pyrrole-4,6-diamine, and 2-[(4-amino-thieno[2,3-b]pyrrol-6-yl)-(2-hydroxy-ethyl)-amino]-ethanol.

SYNTHESIS EXAMPLES

The following are non-limiting synthesis examples of the present invention.

Example A

Furo[3,2-b]pyrrole-2,4,5-triamine, obtaintable from the following synthesis strategy

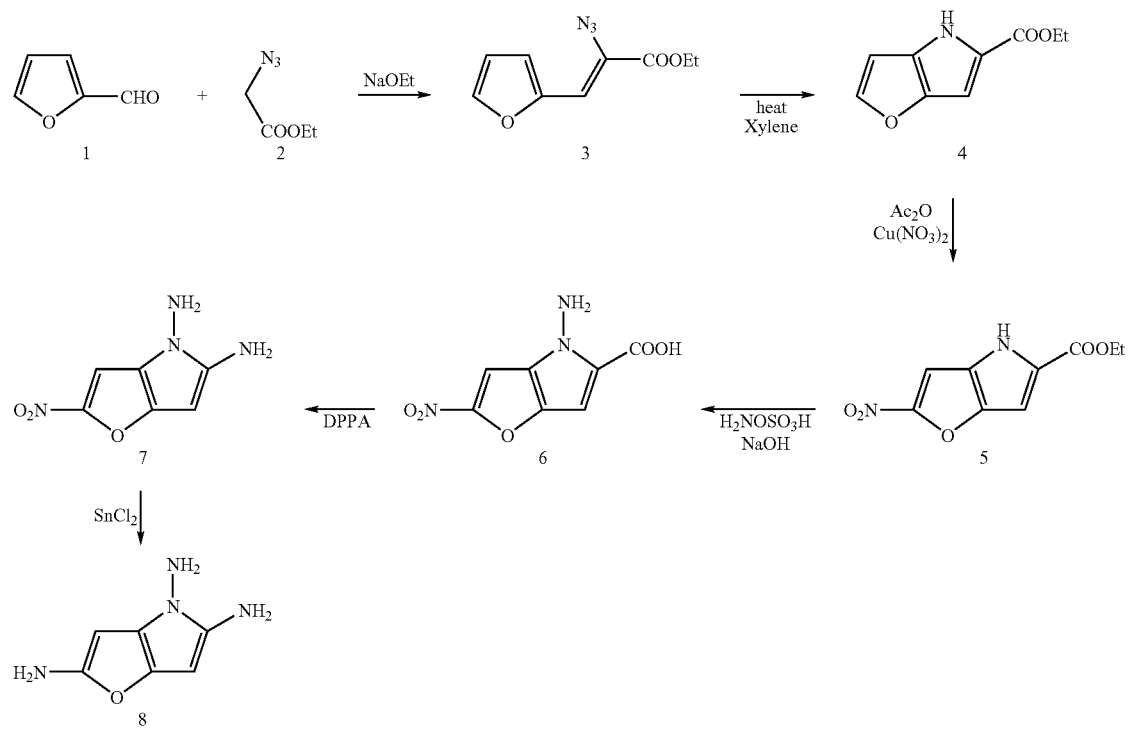

Condensation of 2-furaldehydede 1 with ethyl azidoacetate 2 in the presence of sodium ethoxide affords compound 3. Cyclization of 3 to the furopyrrole ring 4 is carried out by heating in xylene. Nitration of 4 with copper(II) nitrate in acetic anhydride produces compound 5 (J. Heterocyclic Chem. 1984, 21, 215). Treatment of 5 with hydroxylamine 0-sulfonic acid and potassium hydroxide (J. Med. Chem. 1996, 39, 570) affords compound 6. Curtius rearrangement of 6 with diphenylphosphoryl azide (DPPA) affords compound 7. Reduction of 7 with tin (II) chloride provides furo[3,2-b]pyrrole-2,4,5-triamine 8.

Example B

Thieno[3,2-b]pyrrole-2,4-diamine, obtaintable from the following synthesis strategy

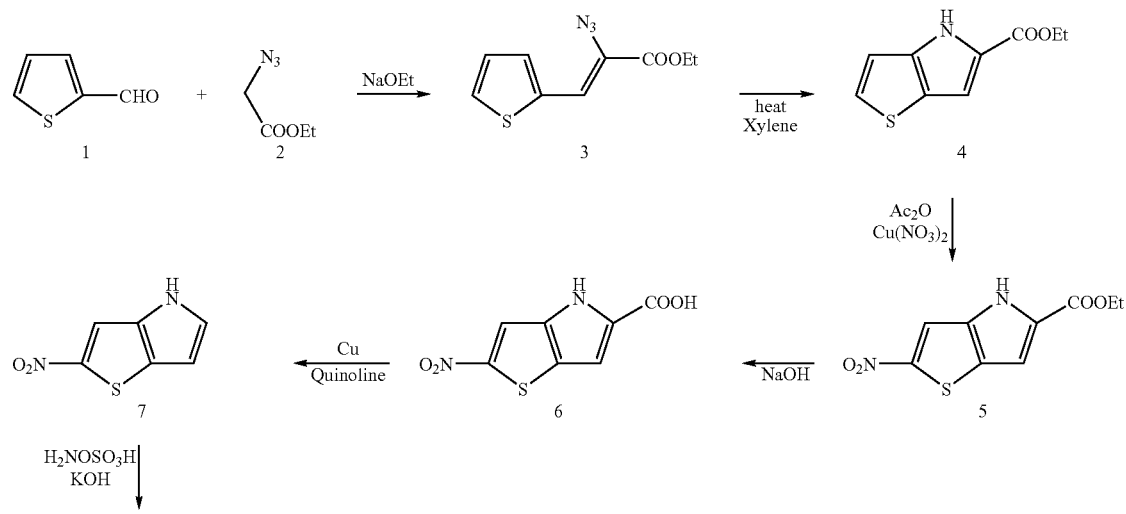

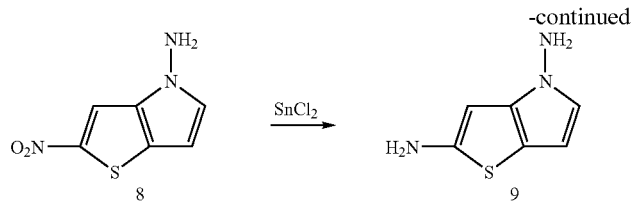

Condensation of 2-thiophenecarboxaldehyde 1 with ethyl azidoacetate 2 in the presence of sodium ethoxide affords compound 3. Cyclization of 3 to the thienopyrrole ring 4 is carried out by heating in xylene. Nitration of 4 with copper (II) nitrate in acetic anhydride produces compound 5 (J. Heterocyclic Chem. 1984, 21, 215). Hydrolysis of 5 with sodium hydroxide leads to compound 6. Decarboxylation of 6 with copper powder in quinoline gives compound 7. Treatment of 7 with hydroxylamine 0-sulfonic acid and potassium hydroxide (J. Med. Chem. 1996, 39, 570) affords compound 8. Reduction of 8 with tin (II) chloride provides thieno[3,2-b]pyrrole-2,4-diamine 9.

II. Keratin Dyeing Composition Components

The inventive compositions for the oxidative dyeing of keratin fibers comprise the hair-dyeing compound described above in the hair-dyeing compounds section and a medium suitable for dyeing. The inventive compositions may further comprise additional components known, conventionally used, or otherwise effective for use in oxidative dye compositions, including but limited to: developer dye compounds; coupler dye compounds; direct dyes; oxidizing agents; thickeners; chelants; pH modifiers and buffering agents; carbonate ion sources and radical scavenger systems; anionic, cationic, nonionic, amphoteric or zwitterionic surfactants, or mixtures thereof; anionic, cationic, nonionic, amphoteric or zwitterionic polymers, or mixtures thereof; fragrances; buffers; dispersing agents; peroxide stabilizing agents; natural ingredients, e.g. proteins and protein derivatives, and plant materials (e.g. aloe, chamomile and henna extracts); silicones (volatile or non-volatile, modified or non-modified), film-forming agents, ceramides, preserving agents; and opacifiers.

Some adjuvants referred to above, but not specifically described below, which are suitable are listed in the International Cosmetics Ingredient Dictionary and Handbook, (8$^{th}$ ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose.

A. Medium Suitable for Dyeing

The medium suitable for dyeing may be selected from water, or a mixture of water and at least one organic solvent to dissolve the compounds that would not typically be sufficiently soluble in water. Suitable organic solvents for use herein include, but are not limited to: C1 to C4 lower alkanols (e.g., ethanol, propanol, isopropanol), aromatic alcohols (e.g. benzyl alcohol and phenoxyethanol); polyols and polyol ethers (e.g., carbitols, 2-butoxyethanol, propylene glycol, propylene glycol monomethyl ether, diethylene glycol monoethyl ether, monomethyl ether, hexylene glycol, glycerol, ethoxy glycol), and propylene carbonate. When present, organic solvents are typically present in an amount ranging from 1% to 30%, by weight, of the composition. Preferred solvents are water, ethanol, propanol, isopropanol, glycerol, 1,2-propylene glycol, hexylene glycol, ethoxy diglycol, and mixtures thereof. Additional mediums suitable for dyeing may include oxidizing agents as described below.

B. Auxiliary Developers

Suitable developers for use in the compositions described herein include, but are not limited to p-phenylenediamine derivatives, e.g. benzene-1,4-diamine (commonly known as p-phenylenediamine), 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol, (commonly known as N,N-bis(2-hydroxyethyl)-p-phenylenediamine) (2,5-diamino-phenyl)-methanol, 1-(2'-Hydroxyethyl)-2,5-diaminobenzene, 2-(2,5-diaminophenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, N$^4$,N$^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)-oxy]ethoxy} ethoxy)ethoxy]benzene-1,4-diamine; 1,3-Bis(N(2-Hydroxyethyl)-N-(4-amino-phenyl) amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylinediamine; p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-1-hydroxy-2-(2'-hydroxyethylaminomethyl)benzene, 4-amino-2-methoxymethyl-phenol, 5-amino-2-hydroxy-benzoic acid, 1-(5-amino-2-hydroxyphenyl)-ethane-1,2-diol, 4-amino-2-(2-hydroxy-ethyl)-phenol, 4-amino-3-(hydroxymethyl)phenol, 4-amino-3-fluorophenol, 4-amino-2-(aminomethyl)-phenol, 4-amino-2-fluoro-phenol; 1-Hydroxy-2,4-diaminobenzene; 1-(2'-Hydroxyethyloxy)-2,4-diaminobenzene; 2,4-Diamino-5-methylphenetol; o-phenylenediamine derivatives such as: 3,4-Diaminobenzoic acid and salts thereof; o-aminophenol derivatives such as: 2-amino-phenol (commonly known as o-aminophenol), 2,4-diaminophenol, 2-amino-5-methylphenol, 2-amino-6-methyl-phenol, N-(4-amino-3-hydroxyphenyl)-acetamide, and 2-amino-4-methyl-phenol; and heterocyclic derivatives such as: pyrimidine-2,4,5,6-tetramine (commonly known as 2,4,5,6-tetraaminopyridine), 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4 (1H)-one, pyridine-2,5-diaamine, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5-diamine, pyrazolo[1,5-a]-pyrimidine-3,7-diamine, 5,6,7-trimethylpyrazolo[1,5-a]pyrimidin-3-ylamine hydrochloride, 7-methylpyrazolo[1,5-a]pyrimidin-3-ylamine hydrochloride, 2,5,6,7-teramethyl-pyrazolo[1,5-a]pyrimidin-3-ylamine hydrochloride, 5,7-di-tert-butylpyrazolo[1,5-a]pyrimidin-3-ylamine hydrochloride, 5,7-di-trifluoromethyl-pyrazolo[1,5-a]pyrimidin-3-ylamine hydrochloride, 2-methylpyrazolo[1,5-a]pyrimidin-3,7-diamine hydrochloride; 4-Hydroxy-2,5,6-triaminopyrimidine; 1-(2'-hydroxyethyl)-amino-3,4-methylene dioxybenzene; and 1-Hydroxyethyl-4,5-diaminopyrazole sulphate.

Additional developers are selected from the group consisting of N-(3-furylmethyl)benzene-1,4-diamine; N-Thiophen-3-ylmethyl-benzene-1,4-diamine; N-(2-furylmethyl)benzene-1,4-diamine; N-Thiophen-2-ylmethyl-benzene-1,4-diamine; 4-Hydroxy-benzoic acid (2,5-diamino-benzylidene)-hydrazide; 3-(2,5-Diamino-phenyl)-N-ethyl-acrylamide; 2-[3-(3-Amino-phenylamino)-propenyl]-benzene-1,4-diamine; 2-[3-(4-Amino-phenylamino)-propenyl]-benzene-1,4-diamine; 2-(6-Methyl-pyridin-2-yl)-benzene-1,4-diamine; 2-Pyridin-2-yl-benzene-1,4-diamine; 2-[3-(4-Amino-phenylamino)-propenyl]-benzene-1,4-diamine; 2-[3-(3-Amino-phenylamino)-propenyl]-benzene-1,4-diamine; 3-(2,5-Diamino-phenyl)-N-ethyl-acrylamide; 2-Thiazol-2-yl-benzene-1,4-diamine; 4-Hydroxy-benzoic acid (2,5-diamino-benzylidene)-hydrazide; 3'-Fluoro-biphenyl-2,5-diamine; 2-Propenyl-benzene-1,4-diamine; 2'-Chloro-biphenyl-2,5-diamine; N-Thiophen-3-ylmethyl-benzene-1,4-diamine; N-(3-furylmethyl)benzene-1,4-diamine; 4'-Methoxy-biphenyl-2,5-diamine; N-(4-Amino-benzyl)-benzene-1,4-diamine; 2-Methyl-5-[(1-H-pyrrol-2-ylmethyl)-amino]-phenol; 5-[(Furan-2-ylmethyl)-amino]-2-methyl-phenol; 5-Isopropylamino-2-methyl-phenol; Biphenyl-2,4,4'-triamine hydrochloride; 5-(4-Amino-phenyl)aminomethyl-benzene-1,3-diamine hydrochloride; 5-Phenylaminomethyl-benzene-1,3-diamine hydrochloride; 2-[4-Amino-2-(3,5-diamino-benzylamino)-phenoxy]-ethanol hydrochloride; 5-(3-Amino-phenyl)aminomethyl-benzene-1,3-diamine hydrochloride; N-(2-Amino-benzyl)-benzene-1,3-diamine hydrochloride; N-Furan-2-ylmethyl-benzene-1,3-diamine hydrochloride; 2-[(3-Amino-phenylamino)-methyl]-phenol hydrochloride; 4-Amino-2-propylaminomethyl-phenol; hydrochloride; N-Benzo[1,3]dioxol-5-ylmethyl-benzene-1,3-diamine hydrochloride; N-[4-Amino-2-(2-hydroxy-ethyl)-2H-pyrazol-3-yl]-3-(5-amino-2-hydroxy-phenyl)-acrylamide; hydrochloride; 4-Amino-2-(isopropylamino-methyl)-phenol; hydrochloride; 4-Thiophen-3-yl-benzene-1,3-diamine; hydrochloride hydrochloride; 5-Phenylaminomethyl-benzene-1,3-diamine hydrochloride; 5-(3-Amino-phenyl)aminomethyl-benzene-1,3-diamine hydrochloride; 4-Thiophen-3-yl-benzene-1,3-diamine; hydrochloride; 2',4'-Diamino-biphenyl-4-ol; hydrochloride; 5-Cyclobutylamino-2-methyl-phenol; 4-Amino-2-(pyridin-3-ylaminomethyl)-phenol; 5-(3-Amino-phenyl)aminomethyl-benzene-1,3-diamine hydrochloride; 5-Allylaminomethyl-benzene-1,3-diamine hydrochloride; N-(4-Amino-benzyl)-benzene-1,3-diamine hydrochloride; N-Benzyl-benzene-1,3-diamine hydrochloride; 3-[(3-Amino-phenylamino)-methyl]-phenol hydrochloride; N-(4-Methoxy-benzyl)-benzene-1,3-diamine hydrochloride; N-Thiophen-2-ylmethyl-benzene-1,3-diamine hydrochloride; 4-Amino-2-[(2-hydroxy-5-nitro-phenylamino)-methyl]-phenol; hydrochloride; 2',4'-Diamino-biphenyl-4-ol hydrochloride; Biphenyl-2,4,4'-triamine; 5-(4-Amino-phenyl)aminomethyl-benzene-1,3-diamine hydrochloride; 2-[4-Amino-2-(3,5-diamino-benzylamino)-phenoxy]-ethanol hydrochloride; 5-Allylaminomethyl-benzene-1,3-diamine hydrochloride; 5-(3-Amino-phenyl)aminomethyl-benzene-1,3-diamine hydrochloride; N-(4-Amino-benzyl)-benzene-1,3-diamine hydrochloride; N-Benzyl-benzene-1,3-diamine hydrochloride; 3-[(3-Amino-phenylamino)-methyl]-phenol hydrochloride; N-(2-Amino-benzyl)-benzene-1,3-diamine hydrochloride; N-(4-Methoxy-benzyl)-benzene-1,3-diamine hydrochloride; N-Furan-2-ylmethyl-benzene-1,3-diamine hydrochloride; 2-[(3-Amino-phenylamino)-methyl]-phenol hydrochloride; N-Thiophen-2-ylmethyl-benzene-1,3-diamine hydrochloride; N-Benzo[1,3]dioxol-5-ylmethyl-benzene-1,3-diamine hydrochloride; N-[4-Amino-2-(2-hydroxy-ethyl)-2H-pyrazol-3-yl]-3-(5-amino-2-hydroxy-phenyl)-acrylamide hydrochloride; 4-Amino-2-propylaminomethyl-phenol; hydrochloride; 4-Amino-2-(isopropylamino-methyl)-phenol hydrochloride; 4-Amino-2-[(2-hydroxy-5-nitro-phenylamino)-methyl]-phenol hydrochloride; 2-Methyl-5-[(1-H-pyrrol-2-ylmethyl)-amino]-phenol; 5-[(Furan-2-ylmethyl)-amino]-2-methyl-phenol; 5-Isopropylamino-2-methyl-phenol; 5-Cyclobutylamino-2-methyl-phenol; 4-Amino-2-(pyridin-3-ylaminomethyl)-phenol; and 5-Cyclobutylamino-2-methyl-phenol.

Preferred developers include but are not limited to: p-phenylenediamine derivatives such as: 2-methyl-benzene-1,4-diamine; benzene-1,4-diamine; 1-(2,5-diamino-phenyl)-ethanol; 2-(2,5-diamino-phenyl)-ethanol; N-(2-methoxyethyl)benzene-1,4-diamine; 2-[(4-amino-phenyl)-(2-hydroxy-ethyl)-amino]-ethanol; 1-(2,5-diaminophenyl)ethane-1,2-diol; 1-(2'-Hydroxyethyl)-2,5-diaminobenzene; 1,3-Bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylinediamine; and mixtures thereof; p-aminophenol derivatives such as: 4-amino-phenol, 4-methylamino-phenol, 4-amino-3-methyl-phenol, 4-amino-2-methoxymethyl-phenol; 1-(5-amino-2-hydroxy-phenyl)-ethane-1,2-diol; 1-Hydroxy-2,4-diaminobenzene; 1-(2'-Hydroxyethyloxy)-2,4-diaminobenzene; 4-Amino-2-aminomethylphenol; 2,4-Diamino-5-methylphenetol; 4-Amino-1-hydroxy-2-(2'-hydroxyethylaminomethyl)benzene; 1-methoxy-2-amino-4-(2'hydroxyethylamino)benzene; 5-aminosalicylic acid and salts thereof; and mixtures thereof; o-phenylenediamine derivatives such as: 3,4-Diaminobenzoic acid and salts thereof; o-aminophenol derivatives such as: 2-amino-phenol, 2-amino-5-methyl-phenol, 2-amino-6-methyl-phenol, N-(4-amino-3-hydroxy-phenyl)-acetamide; 2-amino-4-methyl-phenol; and mixtures thereof; and heterocyclic derivatives such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2,N^2$-dimethyl-pyridine-2,5-diamine; 4-Hydroxy-2,5,6-triaminopyrimidine; 1-(2'hydroxyethyl)-amino-3,4-methylene dioxybenzene; and 1-Hydroxyethyl-4,5-diaminopyrazole sulphate; and mixtures thereof.

More preferred developers include: 2-methyl-benzene-1,4-diamine; benzene-1,4-diamine; N,N-Bis(2-hydroxyethyl)-p-phenylenediamine; 4-amino-phenol; 4-methylamino-phenol; 4-amino-3-methyl-phenol; 1-Hydroxy-2,4-diaminobenzene; 2-amino-phenol; 2-amino-5-methyl-phenol; 2-amino-6-methyl-phenol; 1-methyl-1H-pyrazole-4,5-diamine; 1-Hydroxyethyl-4,5-diaminopyrazole sulphate; 2-(4,5-diamino-1H-pyrazol-1-yl)ethanol; and mixtures thereof.

C. Auxiliary Couplers

Suitable couplers for use in the compositions described herein include, but are not limited to: phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, 2,3-dihydroxy-[1,4]naphthoquinone; and 1-Acetoxy-2-methylnaphthalene; m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-methyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methyl-benzene-1,3-diamine, 4-fluoro-6-methylbenzene-1,3-diamine, 2-({3-[(2-hydroxyethyl)amino]-4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, 2,4-Diamino-5-(2'-hydroxyethyloxy)toluene; N,N-Dimethyl-3-ureidoaniline; N-(2-aminoethyl)benzene-1,3-diamine, 4-{[(2,4-diamino-phenyl)oxy]methoxy}-benzene-1,3-diamine, 1-methyl-2,6-bis(2-hydroxyethylamino)benzene; and 2,4-dimethoxybenzene-1,3-diamine; m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopenty-lamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxy-propyl)amino]-2-methylphenol, 3-[(3-hydroxy-2-methylphenyl)-amino]propane-1,2-diol, 3-[(2-hydroxyethyl)amino]-2-methylphenol; 1-Methyl-2-hydroxy-4-(2'-hydroxyethyl)amino-benzene; 1,3-Bis-(2,4-Diaminophenoxy)propane; 1-Hydroxy-2-methyl-5-amino-6-chlorobenzene; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxy-ethoxy)-pyridin-2-yl]oxy}-ethanol, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine; 3,4-dihydro-2H-1,4-benzoxazin-6-amine; 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole, 2,6-dihydroxypyridine, 2,6-dihydroxy-3,4-dimethylpyridine, 5-methylpyrazolo[5,1-e]-1,2,3-triazole, 5-methyl-6-chloropyrazolo[5,1-e]-1,2,3,-triazole, 5-phenylpyrazolo[5,1-e]-1,2,3-triazole and its addition salts, 1H-2,6-dimethylpyrazolo[1,5-b]-1,2,4-triazole tosylate, 7,8-dicyano-4-methylimidazolo-[3,2-a]imidazole, 2,7-dimethylpyrazolo[1,5-a]pyrimidin-5-one, 2,5-dimethylpyrazolo[1,5-a]pyrimidin-7-one, and 2-methyl-5-methoxymethyl-pyrazolo[1,5-a]pyrimidin-7-one; 6-Hydroxybenzomorpholine; and 3-Amino-2-methylamino-6-methoxypyridine; 1-Phenyl-3-methyl-5-pyrazolone-2,4-dihydro-5,2-phenyl-3H-pyrazole-3-one.

Additional couplers are selected from the group consisting of N-(3-furylmethyl)benzene-1,4-diamine; N-Thiophen-3-ylmethyl-benzene-1,4-diamine; N-(2-furylmethyl)benzene-1,4-diamine; N-Thiophen-2-ylmethyl-benzene-1,4-diamine; 4-Hydroxy-benzoic acid (2,5-diamino-benzylidene)-hydrazide; 3-(2,5-Diamino-phenyl)-N-ethyl-acrylamide; 2-[3-(3-Amino-phenylamino)-propenyl]-benzene-1,4-diamine; 2-[3-(4-Amino-phenylamino)-propenyl]-benzene-1,4-diamine; 2-(6-Methyl-pyridin-2-yl)-benzene-1,4-diamine; 2-Pyridin-2-yl-benzene-1,4-diamine; 2-[3-(4-Amino-phenylamino)-propenyl]-benzene-1,4-diamine; 2-[3-(3-Amino-phenylamino)-propenyl]-benzene-1,4-diamine; 3-(2,5-Diamino-phenyl)-N-ethyl-acrylamide; 2-Thiazol-2-yl-benzene-1,4-diamine; 4-Hydroxy-benzoic acid (2,5-diamino-benzylidene)-hydrazide; 3'-Fluoro-biphenyl-2,5-diamine; 2-Propenyl-benzene-1,4-diamine; 2'-Chloro-biphenyl-2,5-diamine; N-Thiophen-3-ylmethyl-benzene-1,4-diamine; N-(3-furylmethyl)benzene-1,4-diamine; 4'-Methoxy-biphenyl-2,5-diamine; N-(4-Amino-benzyl)-benzene-1,4-diamine; 2-Methyl-5-[(1-H-pyrrol-2-ylmethyl)-amino]-phenol; 5-[(Furan-2-ylmethyl)-amino]-2-methyl-phenol; 5-Isopropylamino-2-methyl-phenol; Biphenyl-2,4,4'-triamine hydrochloride; 5-(4-Amino-phenyl)aminomethyl-benzene-1,3-diamine hydrochloride; 5-Phenylaminomethyl-benzene-1,3-diamine hydrochloride; 2-[4-Amino-2-(3,5-diamino-benzylamino)-phenoxy]-ethanol hydrochloride; 5-(3-Amino-phenyl)aminomethyl-benzene-1,3-diamine hydrochloride; N-(2-Amino-benzyl)-benzene-1,3-diamine hydrochloride; N-Furan-2-ylmethyl-benzene-1,3-diamine hydrochloride; 2-[(3-Amino-phenylamino)-methyl]-phenol hydrochloride; 4-Amino-2-propylaminomethyl-phenol; hydrochloride; N-Benzo[1,3]dioxol-5-ylmethyl-benzene-1,3-diamine hydrochloride; N-[4-Amino-2-(2-hydroxy-ethyl)-2H-pyrazol-3-yl]-3-(5-amino-2-hydroxy-phenyl)-acrylamide; hydrochloride;

4-Amino-2-(isopropylamino-methyl)-phenol; hydrochloride; 4-Thiophen-3-yl-benzene-1,3-diamine; hydrochloride hydrochloride; 5-Phenylaminomethyl-benzene-1,3-diamine hydrochloride; 5-(3-Amino-phenyl)aminomethyl-benzene-1,3-diamine hydrochloride; 4-Thiophen-3-yl-benzene-1,3-diamine; hydrochloride; 2',4'-Diamino-biphenyl-4-ol; hydrochloride; 5-Cyclobutylamino-2-methyl-phenol; 5-Cyclobutylamino-2-methyl-phenol; 4-Amino-2-(pyridin-3-ylaminomethyl)-phenol; 5-(3-Amino-phenyl)aminomethyl-benzene-1,3-diamine hydrochloride; 5-Allylaminomethyl-benzene-1,3-diamine hydrochloride; N-(4-Amino-benzyl)-benzene-1,3-diamine hydrochloride; N-Benzyl-benzene-1,3-diamine hydrochloride; 3-[(3-Amino-phenylamino)-methyl]-phenol hydrochloride; N-(4-Methoxy-benzyl)-benzene-1,3-diamine hydrochloride; N-Thiophen-2-ylmethyl-benzene-1,3-diamine hydrochloride; 4-Amino-2-[(2-hydroxy-5-nitro-phenylamino)-methyl]-phenol; hydrochloride; 2',4'-Diamino-biphenyl-4-ol hydrochloride; Biphenyl-2,4,4'-triamine; 5-(4-Amino-phenyl)aminomethyl-benzene-1,3-diamine hydrochloride; 2-[4-Amino-2-(3,5-diamino-benzylamino)-phenoxy]-ethanol hydrochloride; 5-Allylaminomethyl-benzene-1,3-diamine hydrochloride; 5-(3-Amino-phenyl)aminomethyl-benzene-1,3-diamine hydrochloride; N-(4-Amino-benzyl)-benzene-1,3-diamine hydrochloride; N-Benzyl-benzene-1,3-diamine hydrochloride; 3-[(3-Amino-phenylamino)-methyl]-phenol hydrochloride; N-(2-Amino-benzyl)-benzene-1,3-diamine hydrochloride; N-(4-Methoxy-benzyl)-benzene-1,3-diamine hydrochloride; N-Furan-2-ylmethyl-benzene-1,3-diamine hydrochloride; 2-[(3-Amino-phenylamino)-methyl]-phenol hydrochloride; N-Thiophen-2-ylmethyl-benzene-1,3-diamine hydrochloride; N-Benzo[1,3]dioxol-5-ylmethyl-benzene-1,3-diamine hydrochloride; N-[4-Amino-2-(2-hydroxy-ethyl)-2H-pyrazol-3-yl]-3-(5-amino-2-hydroxy-phenyl)-acrylamide hydrochloride; 4-Amino-2-propylaminomethyl-phenol; hydrochloride; 4-Amino-2-(isopropylamino-methyl)-phenol hydrochloride; 4-Amino-2-[(2-hydroxy-5-nitro-phenylamino)-methyl]-phenol hydrochloride; 2-Methyl-5-[(1-H-pyrrol-2-ylmethyl)-amino]-phenol; 5-[(Furan-2-ylmethyl)-amino]-2-methyl-phenol; 5-Isopropylamino-2-methyl-phenol; 5-Cyclobutylamino-2-methyl-phenol; 4-Amino-2-(pyridin-3-ylaminomethyl)-phenol; and 5-Cyclobutylamino-2-methyl-phenol.

Preferred couplers include but are not limited to: phenol, resorcinol, and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol; 1,2,4-Trihydroxybenzene; 1-Acetoxy-2-methylnaphthalene;and mixtures thereof; m-phenylenediamine derivatives such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol; 2,4-Diamino-5-(2'-hydroxyethyloxy)toluene; N,N-Dimethyl-3-ureidoaniline; 2,4-Diamino-5-fluorotoluenesulfatehydrate; 1-methyl-2,6-bis(2-hydroxyethylamino)benzene; and mixtures thereof; m-aminophenol derivatives such as: 3-amino-phenol, 5-amino-2-methyl-phenol, 5-(2-hydroxy-ethylamino)-2-methyl-phenol, and 3-amino-2-methyl-phenol; 1-Methyl-2-hydroxy-4-(2'-hydroxyethyl)aminobenzene; 1-Hydroxy-3-amino-2,4-dichlorobenzene; 1,3-Bis-(2,4-Diaminophenoxy)propane; 1-Hydroxy-2-methyl-5-amino-6-chlorobenzene; 5-Amino-4-chloro-2-methylphenol; and mixtures thereof; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, 2-aminopyridin-3-ol, 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole; 2,6-dihydroxypyridine; 2,6-dihydroxy-3,4-dimethylpyridine; 6-Hydroxybenzomorpholine; 2,6-Dihydroxy-3,4-dimethylpyridine; 3,5-Diamino-2,6-dimethoxypyridine; 3-Amino-2-methylamino-6-methoxypyridine; 1-Phenyl-3-methyl-5-pyrazolone-2,4-dihydro-5,2-phenyl-3H-pyrazole-3-one; and mixtures thereof.

More preferred couplers include: benzene-1,3-diol; 4-chlorobenzene-1,3-diol; 2-methyl-benzene-1,3-diol; benzene-1,3-diamine; 3-amino-phenol; 5-amino-2-methyl-phenol; 1-Methyl-2-hydroxy-4-(2'-hydroxyethyl)aminobenzene; 4-methyl-2-phenyl-2,4-dihydro-3H-pyrazol-3-one; 2-aminopyridin-3-ol; 1-phenyl-3-methylpyrazol-5-one; 1-Phenyl-3-methyl-5-pyrazolone-2,4-dihydro-5,2-phenyl-3H-pyrazole-3-one; and mixtures thereof.

Additional preferred developers and couplers include 5-methoxymethyl-2-aminophenol, 5-ethyl-2-aminophenol, 5-phenyl-2-aminophenol, and 5-cyanoethyl-2-aminophenol.

Further preferred developers and couplers include: 5-membered heteroaromatic keratin dyeing compounds with one, two, or three heteroatoms relating to the following compounds:

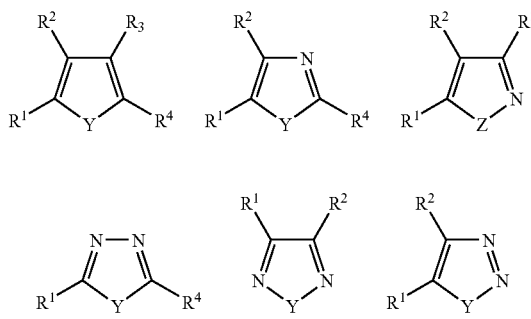

wherein Z is selected from the group consisting of S and O;

wherein Y is selected from the group consisting of $NA^1$, S and O; Bicyclic fused 5-5 heteroaromatic keratin dyeing compounds with two or three heteroatoms relating to the following compounds:

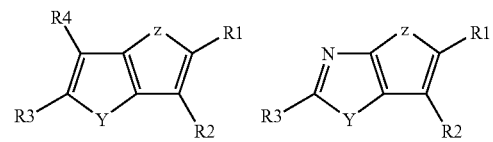

wherein Y and Z are independently selected from the group consisting of $NA^1$, S and O; Bicyclic 5-5 heteroaromatic compounds having a ring junction nitrogen according to the following formulas:

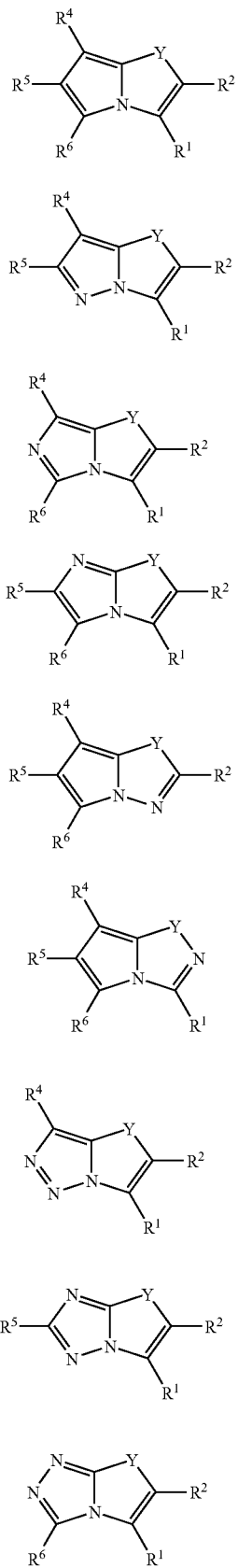
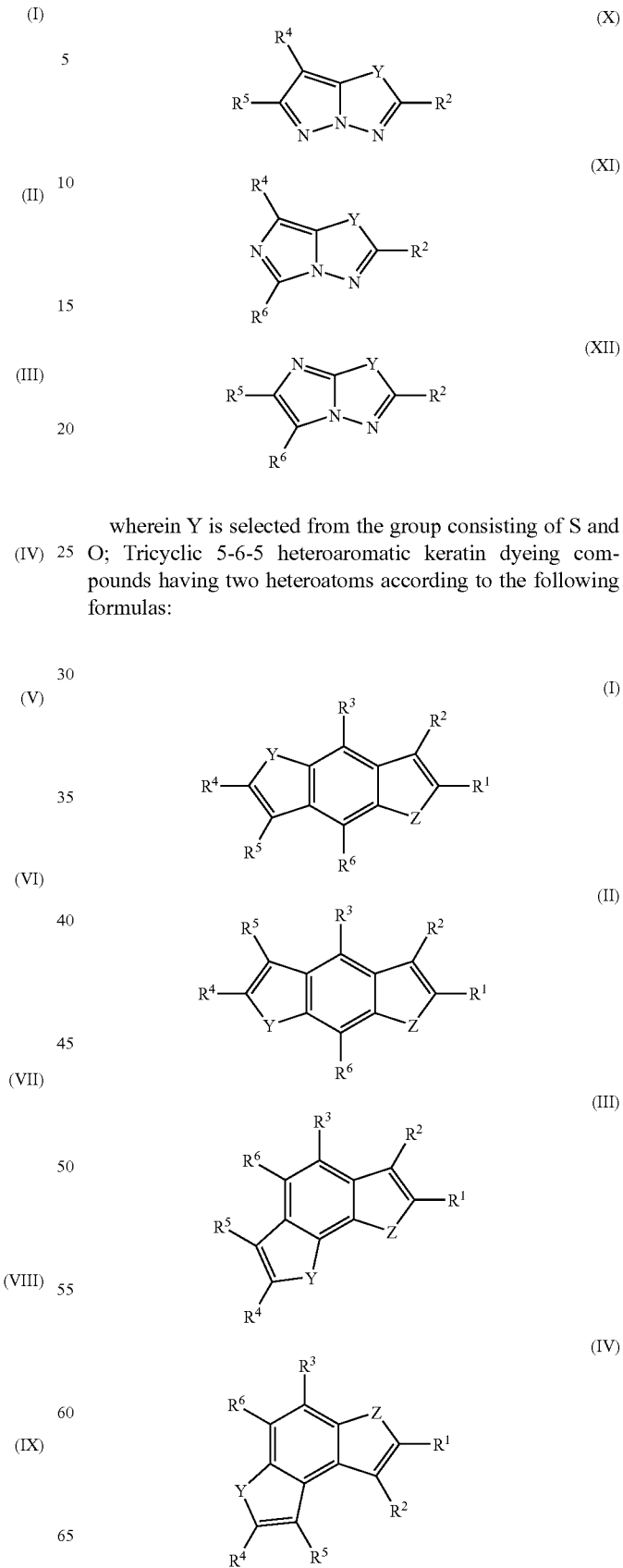
wherein Y is selected from the group consisting of S and O; Tricyclic 5-6-5 heteroaromatic keratin dyeing compounds having two heteroatoms according to the following formulas:

wherein Y and Z are selected from the group consisting of NA¹, S, and O; Bicyclic 5-6 heteroaromatic keratin dyeing compounds with one ring junction nitrogen and one or two extra heteroatoms according to the following formulas:
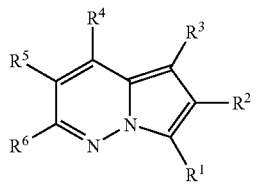
(I)
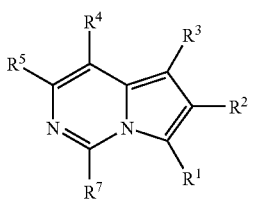
(II)
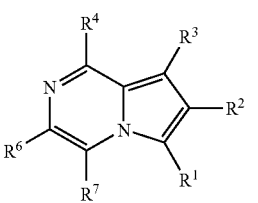
(III)
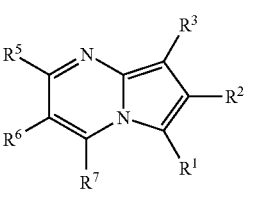
(IV)
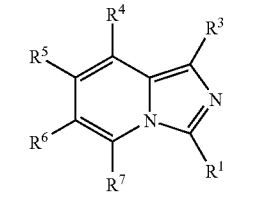
(V)
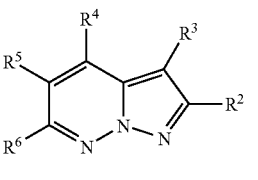
(VI)
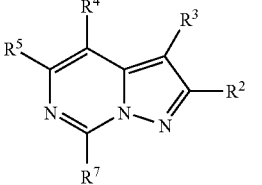
(VII)
-continued
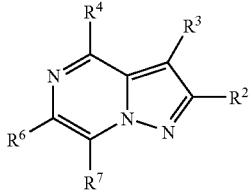
(VIII)
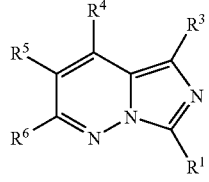
(IX)
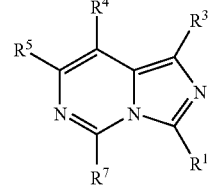
(X)
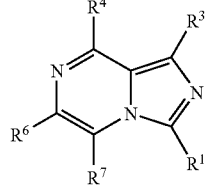
(XI)
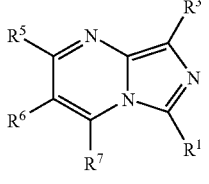
(XII)
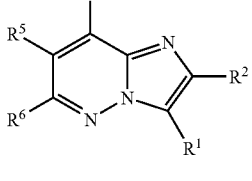
(XIII)
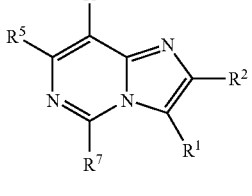
(XIV)
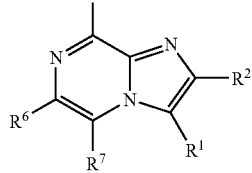
(XV)

-continued

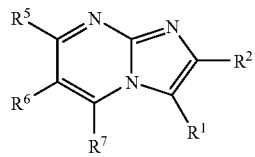
(XVI)

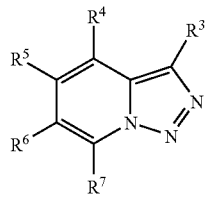
(XVII)

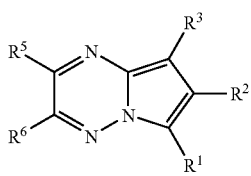
(XVIII)

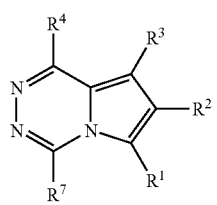
(XIX)

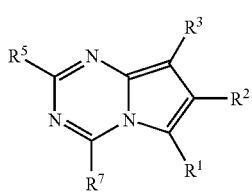
(XX)

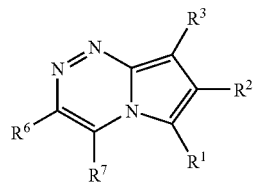
(XXI)

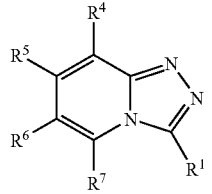
(XXII)

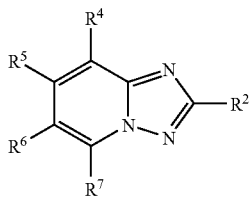
(XXIII)

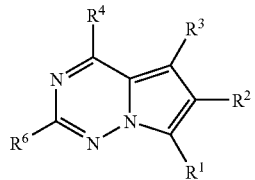
(XXIV)

Tricyclic fused 6-5-6 heteroaromatic keratin dyeing compounds having one heteroatom according to the following formula:

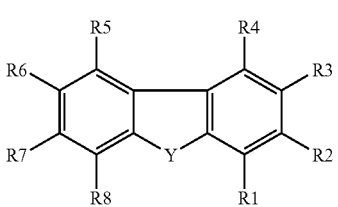

wherein Y is independently selected from the group consisting of $NA^1$, S and O; 5-membered aza heteroaromatic keratin dyeing compounds with an N-hydroxy or N-amino group and derivatives thereof, according to the following formulas:

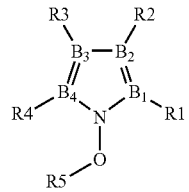
I

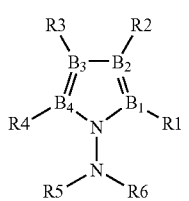
II wherein $B_1$, $B_2$, $B_3$, and $B_4$ are selected from the group consisting of CH and N;

wherein the corresponding $R^1$, $R^2$, $R^3$, and $R^4$ is absent when B is N; Bicyclic 5-6 systems of aza heteroaromatic keratin dyeing compounds wherein the 5-membered rings have one to three nitrogen atoms and an N-hydroxy or N-amino group and derivatives thereof, according to the following formulas:

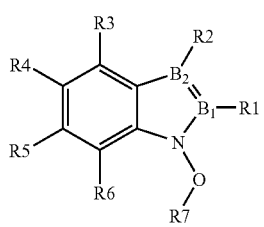
I

-continued

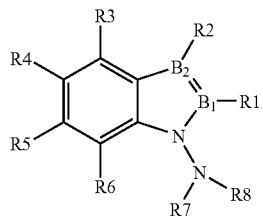
II wherein B₁ and B₂ are independently selected from CH or N;

wherein the corresponding $R^1$ and $R^2$ is absent when B is N; Bicyclic fused 5-5-membered aza heteroaromatic keratin dyeing compounds having a ring junction nitrogen and an N-hydroxy or N-amino group and derivatives thereof, according to the following formulas:

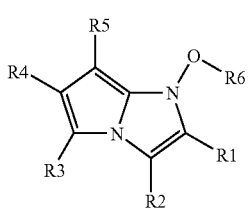
Ia,c,e

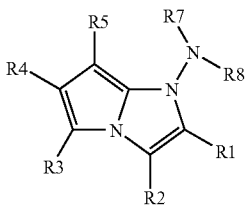
Ib,d,f

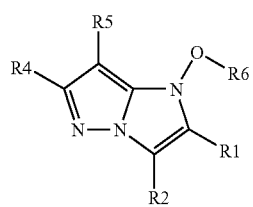
IIa,c

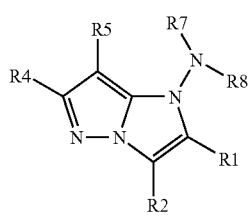
IIb,d

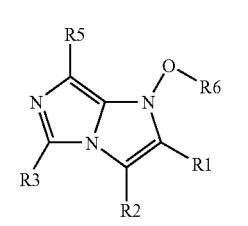
IIIa,c,e

-continued

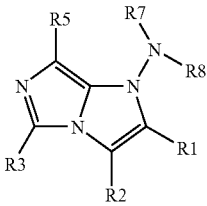
IIIb,d,f

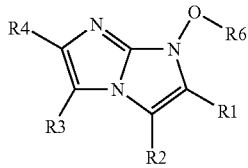
IVa,c

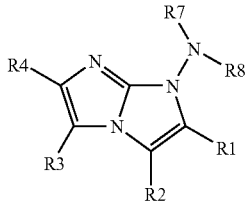
IVb,d

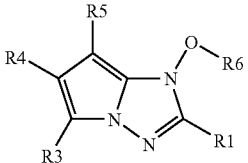
Va,c,e

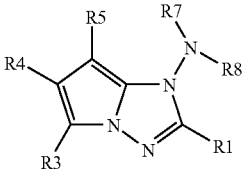
Vb,d,f

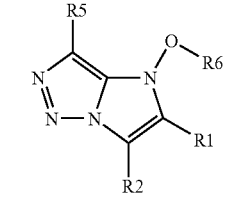
VIa,c

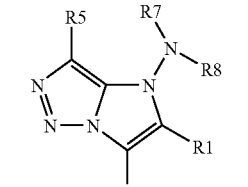
VIb,d

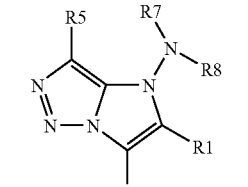
VIIa,c

-continued

VIIb,d

VIIIa,c

VIIIb,d

IXa,c,e

IXb,d,f

Xa,c

Xb,d

XIa,c

-continued

XIb,d

XIIa,c,e

XIIb,d,f

XIIIa,c

XIIIb,d

XIVa,c

XIVb,d

-continued

XVa,c
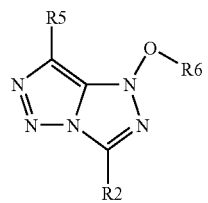

XVb,d
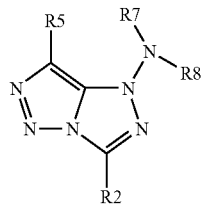

XVIa
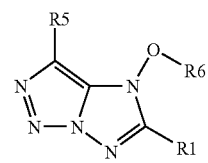

XVIb
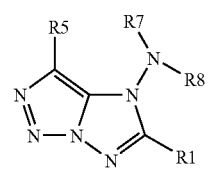

XVIIa
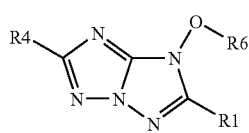

XVIIb
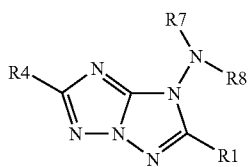

XVIIIa
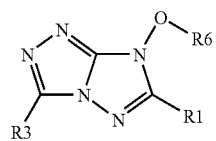

XVIIIb
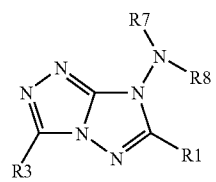

Bicyclic fused 5-5-membered aza heteroaromatic keratin dyeing compounds having a ring junction nitrogen and an N-hydroxy or N-amino group and derivatives thereof, according to the following formulas:

A
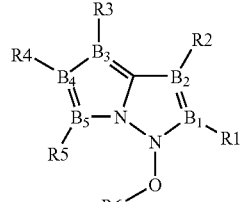

B
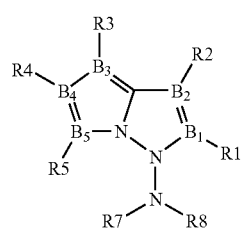

wherein $B_1$, $B_2$, $B_3$, $B_4$, and $B_5$ are selected from the group consisting of CH and N;

wherein the corresponding R1, R2, R3, R4, and R5 is absent when B is N;

N-oxides of six-membered rings with one or two nitrogen atoms according to the following formulas:

I
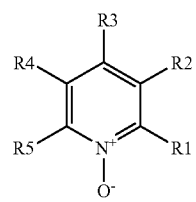

II
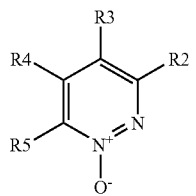

III
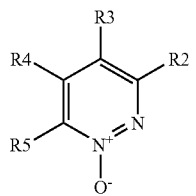

IV
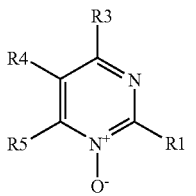

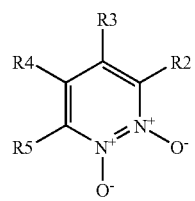
V
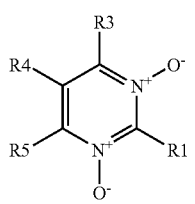
VI
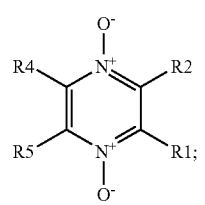
VII
Bicyclic 6-6 (0:1, 0:2, 1:1, 1:2) aza heteroaromatic keratin dyeing compounds with one or two N-oxides, according to the following formulas:
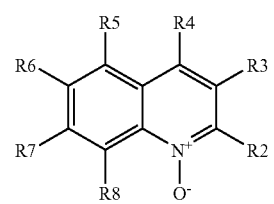
I
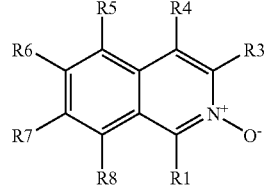
II
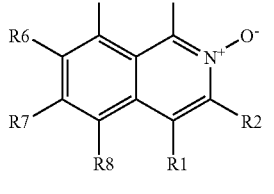
III
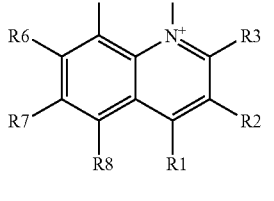
IV
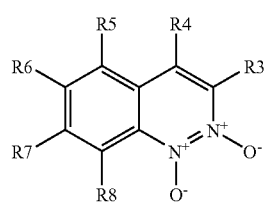
V
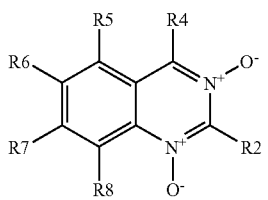
VI
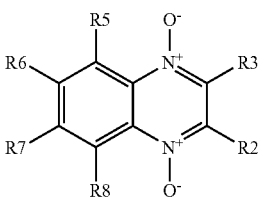
VII
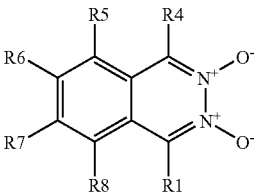
VIII
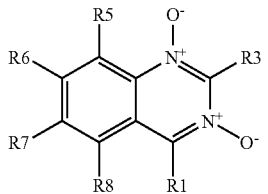
IX
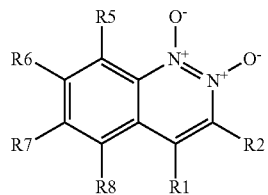
X
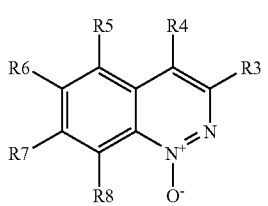
XI -continued
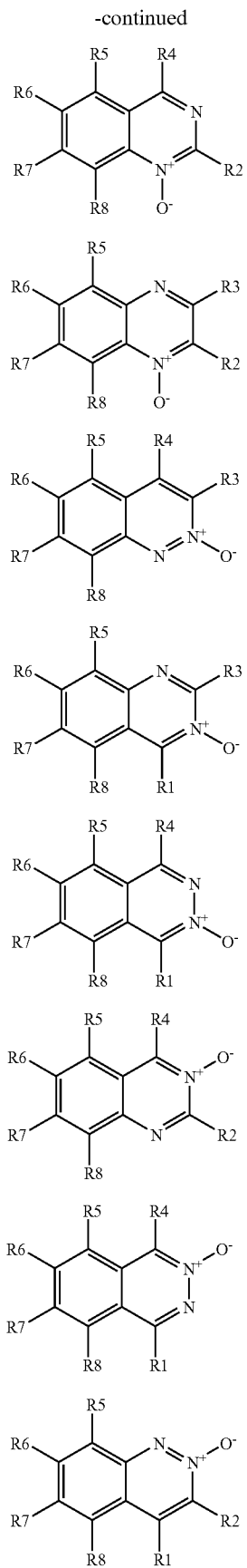
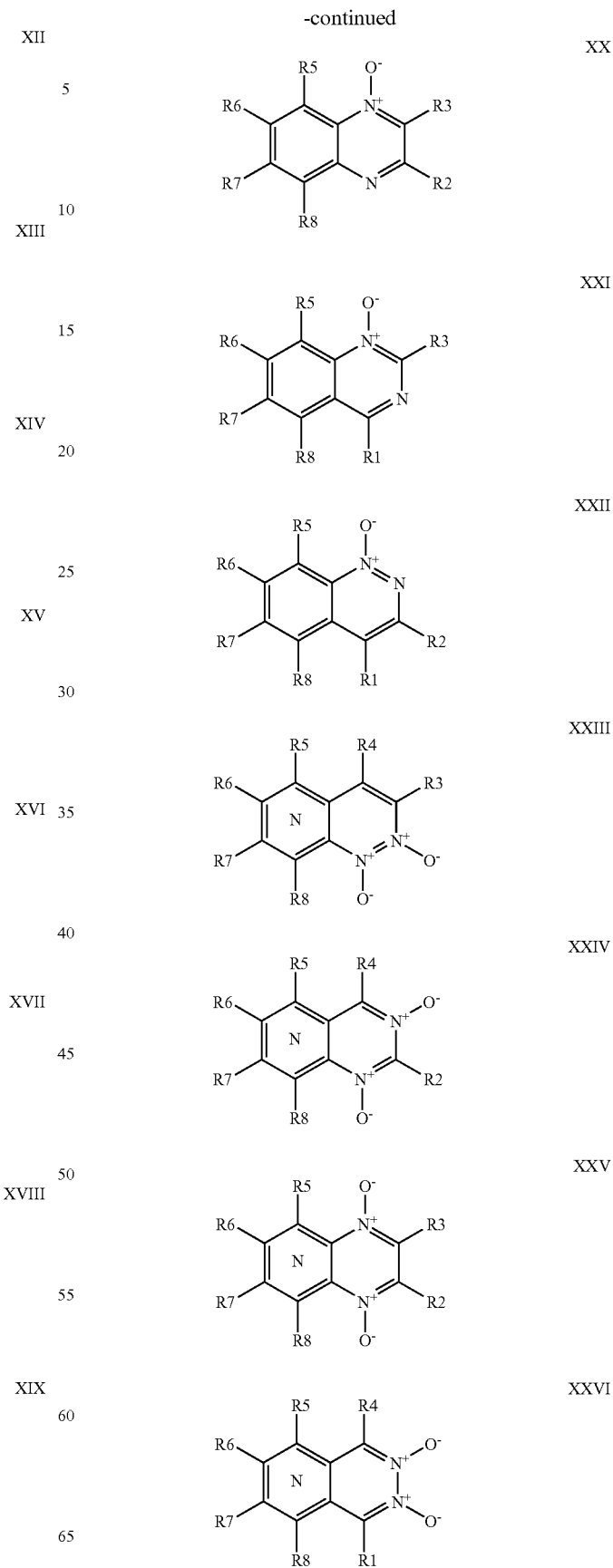

-continued
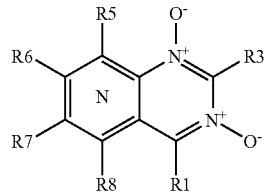
XXVII
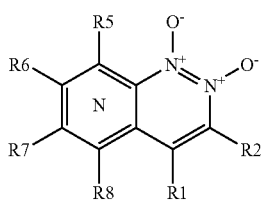
XXVIII
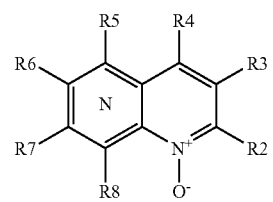
XXIX
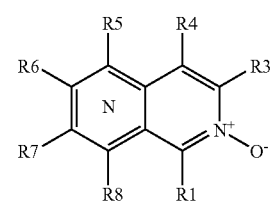
XXX
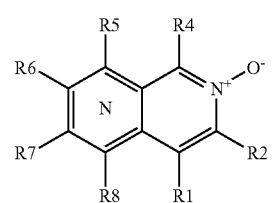
XXXI
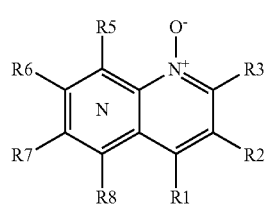
XXXII
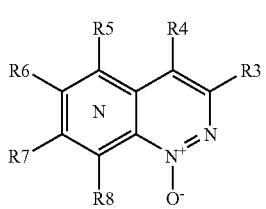
XXXIII
-continued
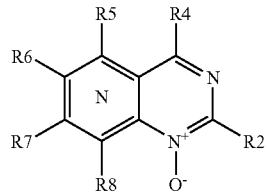
XXXIV
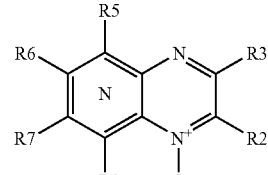
XXXV
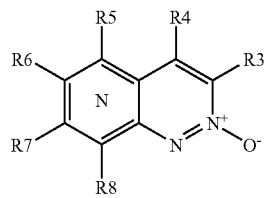
XXXVI
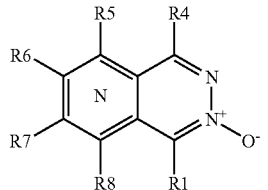
XXXVII
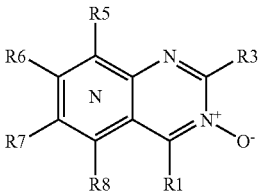
XXXVIII
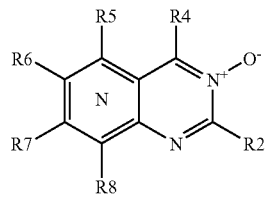
XXXIX
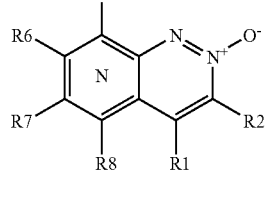
XXXX
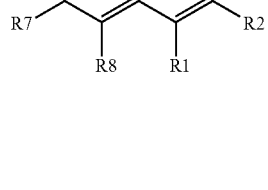
XXXXI -continued
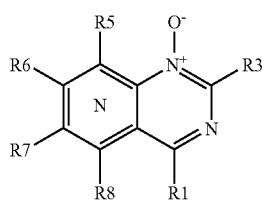
XXXXII
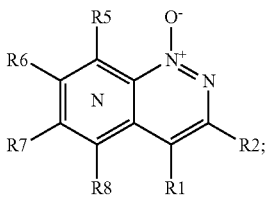
XXXXIII
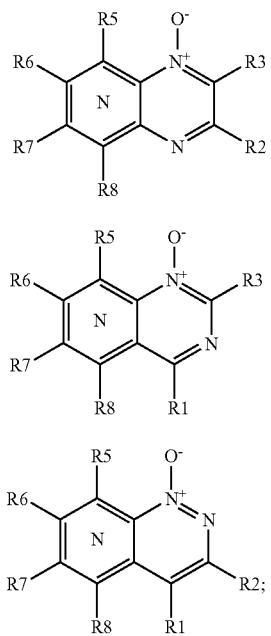
XXXXIV
Bicyclic 5-5 heteroaromatic compounds with a ring junction N (1:0, 1:1, 2:0, 2:1), according to the following formulas:
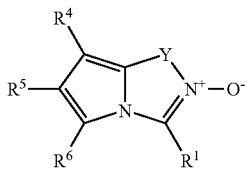
(I)
(II)
(III)
(IV)
(V)
-continued
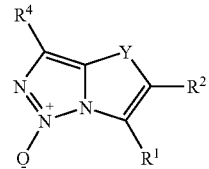
(VI)
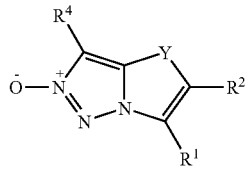
(VII)
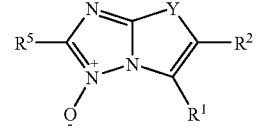
(VIII)
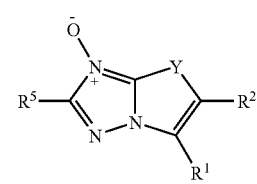
(IX)
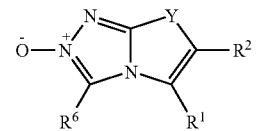
(X)
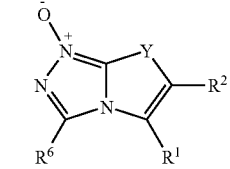
(XI)
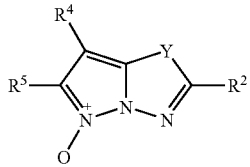
(XII)
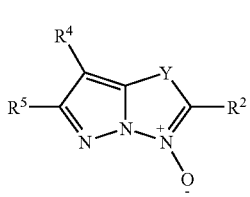
(XIII)
(XIV)

-continued

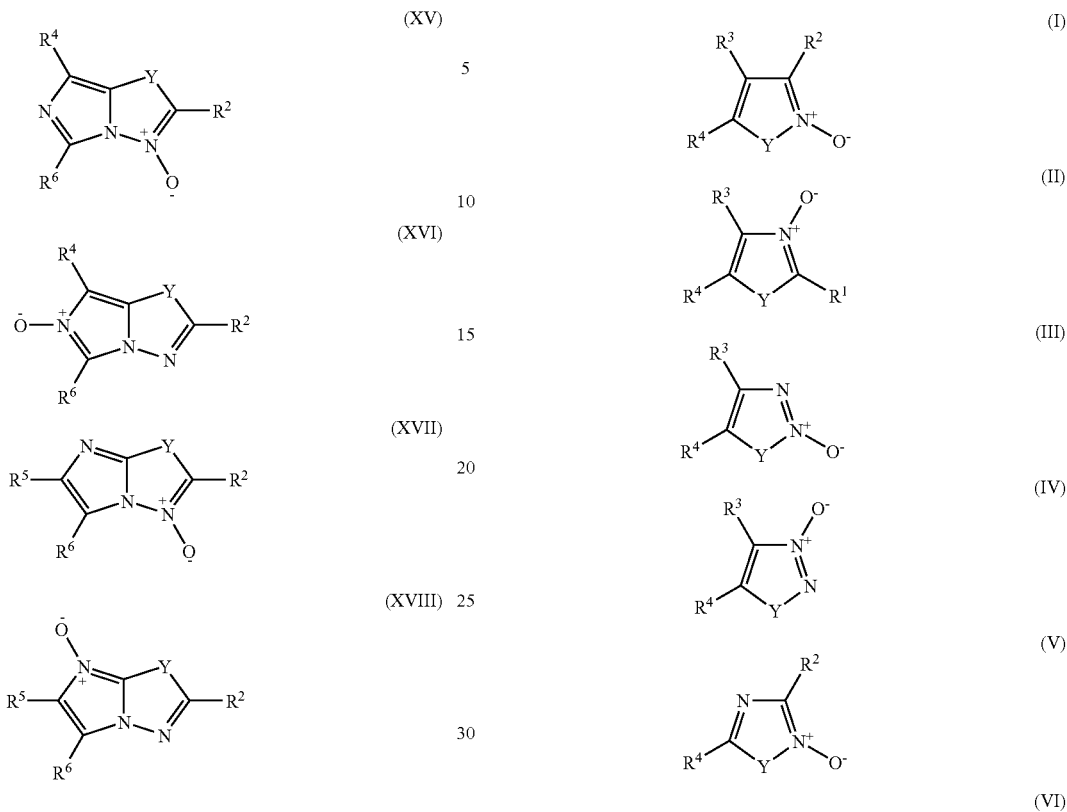

wherein Y is selected from the group consisting of CH$_2$, NR$^7$, O or S; Bicyclic 5-5 (1:2) heteroaromatic N-oxide keratin dyeing compounds and derivatives thereof, according to the following formulas:

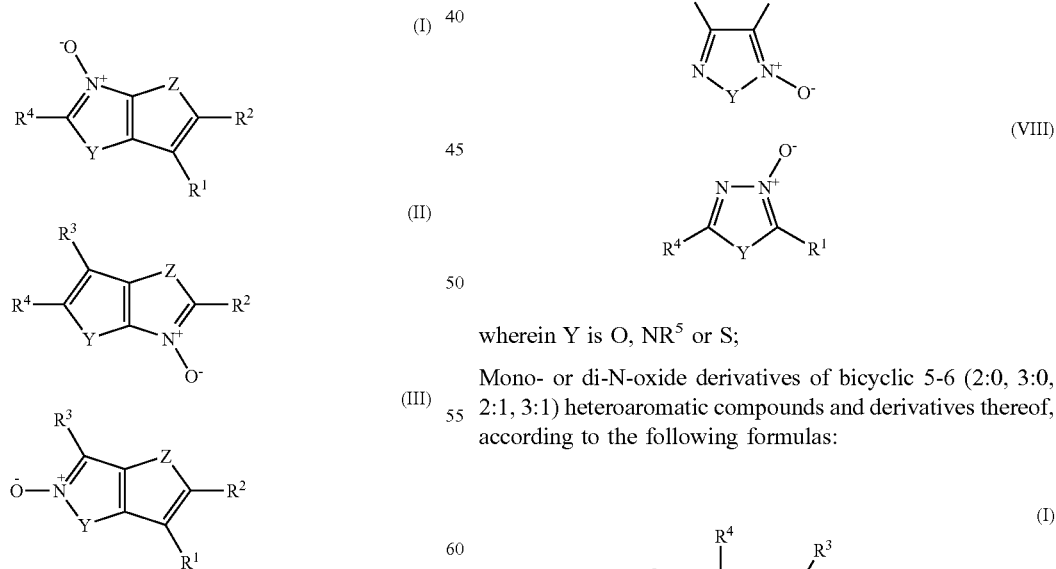

wherein Y is O, NR$^5$ or S;

Mono- or di-N-oxide derivatives of bicyclic 5-6 (2:0, 3:0, 2:1, 3:1) heteroaromatic compounds and derivatives thereof, according to the following formulas:

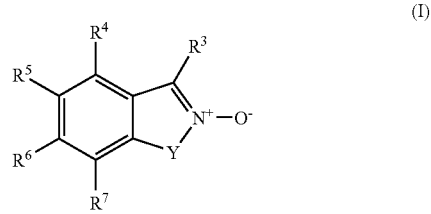

wherein Y and Z are selected from the group consisting of NR$^5$, O and S; Mono N-oxide derivatives of 5-membered heteroaromatic compounds and derivatives thereof, according to the following formulas:

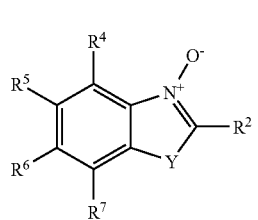
(II)
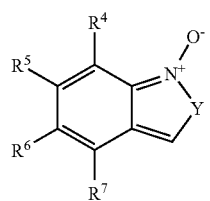
(III)
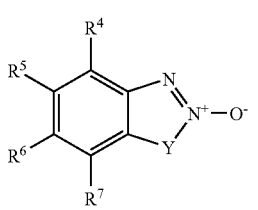
(IV)
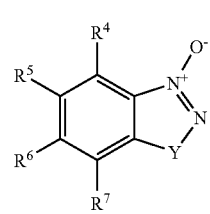
(V)
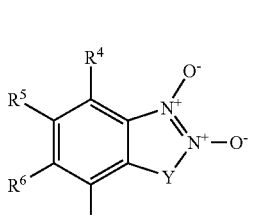
(VI)
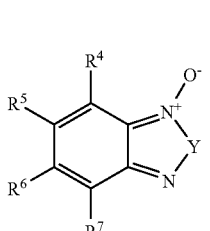
(VII)
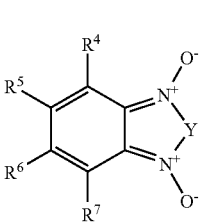
(VIII)
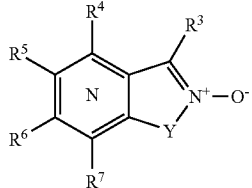
(IX)
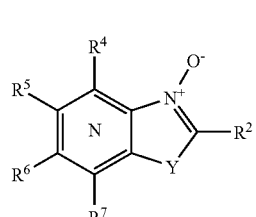
(X)
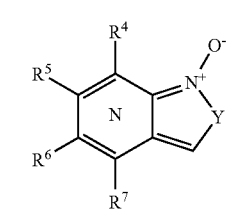
(XI)
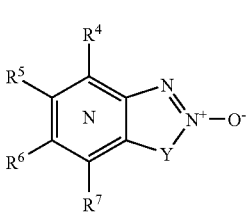
(XII)
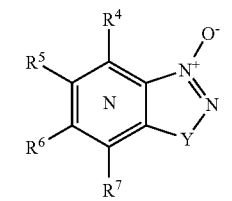
(XIII)
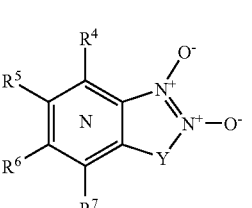
(XIV)
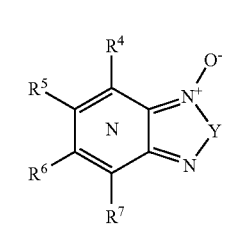
(XV)

-continued
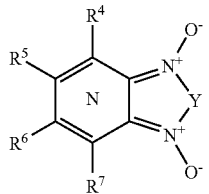
(XVI)
wherein Y is selected from the group consisting of $NR^8$, O or S;
N-oxide derivatives of bicyclic 5-6 heteroaromatic compounds with a ring junction N (0:1, 1:0 & 1:1) and derivatives thereof, according to the following formulas:
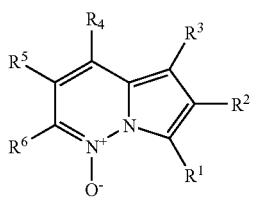
(I)
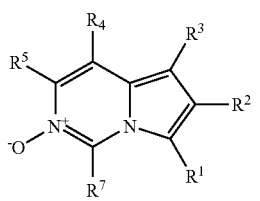
(II)
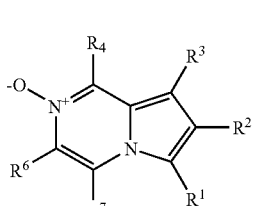
(III)
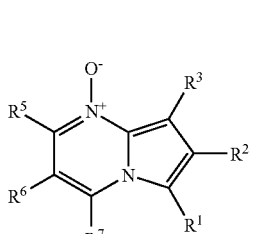
(IV)
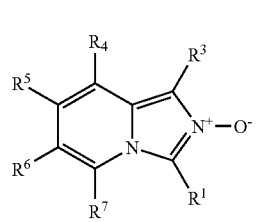
(V)
-continued
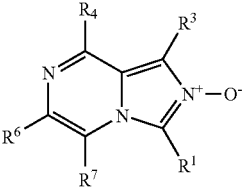
(VI)
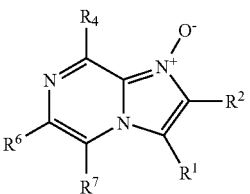
(VII)
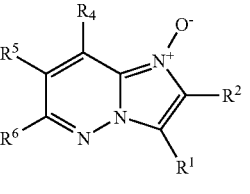
(VIII)
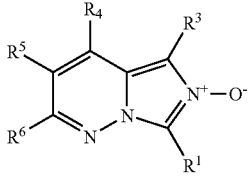
(IX)
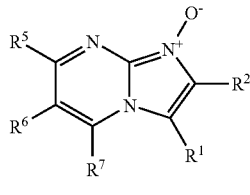
(X)
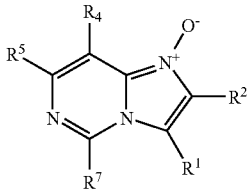
(XI)
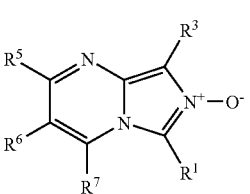
(XII)
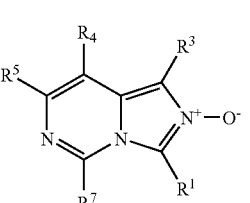
(XIII)

-continued (XIV) 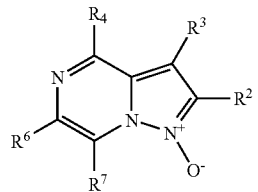

(XV) 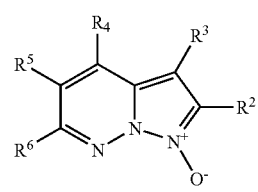

(XVI) 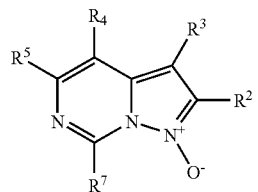

(XVII) 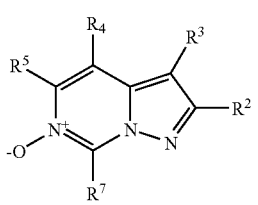

(XVIII) 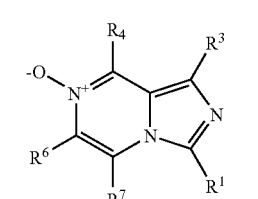

(XVIX) 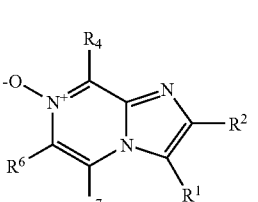

(XX) 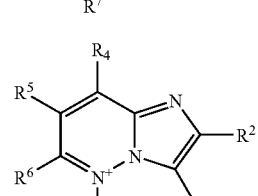

(XXI) 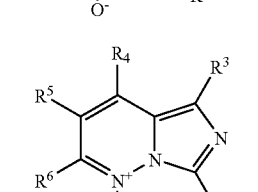

-continued (XXII) 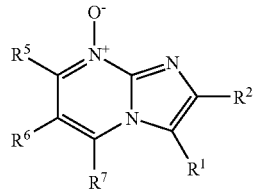

(XXIII) 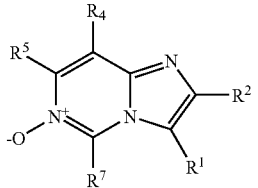

(XXIV) 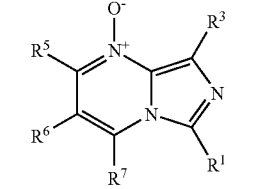

(XXVI) 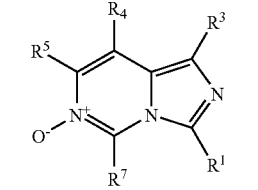

(XXVII) 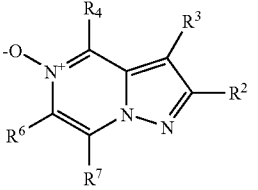

(XXVIII) 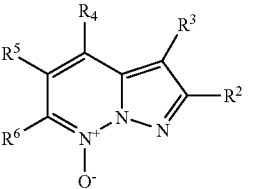

wherein all of the aforementioned R groups are the same or different and are selected from the group consisting of:
(a) C-linked monovalent substituents selected from the group consisting of:
(i) substituted or unsubstituted, straight or branched, alkyl, mono- or poly-unsaturated alkyl, heteroalkyl, aliphatic, heteroaliphatic, or heteroolefinic systems,
(ii) substituted or unsubstituted, mono- or poly-cyclic aliphatic, aryl, or heterocyclic systems, and
(iii) substituted or unsubstituted, mono-, poly-, or per-fluoro alkyl systems;
wherein said systems of (i), (ii) and (iii) comprise from about 1 to about 10 carbon atoms and from about 0 to about 5 heteroatoms selected from the group consisting of O, S, N, P, and Si;

wherein substituents of the substituted systems of the C-linked monovalent substituents are selected from the group consisting of amino, hydroxyl, alkylamino (linear, branched, or cyclic C1-C5), dialkylamino (linear, branched, or cyclic C1-C5), hydroxyalkylamino (linear, branched, or cyclic C1-C5), dihydroxyalkylamino (linear, branched, or cyclic C1-C5), arylamino or substituted arylamino (substituents are halogen, C1-C5 alkyl, C1-C5 alkoxy, trifluoromethyl, amino, C1-C5 alkylamino), heteroarylamino or substituted heteroarylamino (substituents are halogen, C1-C5 alkyl, C1-C5 alkoxy, trifluoromethyl, amino, C1-C5 alkylamino), arylmethylamino or substituted arylmethylamino (substituents are halogen, C1-C5 alkyl, C1-C5 alkoxy, trifluoromethyl, amino, C1-C5 alkylamino), and heteroarylmethylamino or substituted heteroarylmethylamino (substituents are halogen, C1-C5 alkyl, C1-C5 alkoxy, trifluoromethyl, amino, C1-C5 alkylamino), (b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;

(c) O-linked monovalent substituents selected from the group consisting of $OA^1$, and $ONA^1A^2$;

(d) N-linked monovalent substituents selected from the group consisting of $NA^1A^2$, $(NA^1A^2A^3)^+$, $NA^1OA^2$, $NA^1SA^2$, $NO_2$, $N=NA^1$, $N=NOA^1$, $NA^1CN$, and $NA^1NA^2A^3$;

(e) monovalent substituents selected from the group consisting of $COOA^1$, $CONA^1_2$, $CONA^1COA^2$, $C(=NA^1)NA^1A^2$, CN, and X;

(f) fluoroalkyl monovalent substituents selected from the group consisting of mono-, poly-, and per-fluoro alkyl systems comprising from about 1 to about 12 carbon atoms and from about 0 to about 4 heteroatoms; and (g) hydrogen, wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, or per-fluoro alkyl systems, or $A^1$ and $A^2$ together with nitrogen atoms to which they are bound form a ring; wherein said systems comprise from about 1 to about 10 carbon atoms and from about 0 to about 5 heteroatoms selected from the group consisting of O, S, N, P, and Si;

wherein X is a halogen selected from the group consisting of F, Cl, Br, and I.

D. Direct Dyes

The inventive compositions may also comprise compatible direct dyes, in an amount sufficient to provide additional coloring, particularly with regard to intensity. Typically, such an amount will range from 0.05% to 4%, by weight, of the composition. Suitable direct dyes include but are not limited to: Acid Yellow 1, Acid Orange 3, Disperse Red 17, Basic Brown 17, Acid Black 52, Acid Black 1, Disperse Violet 4, 4-Nitro-o-Phenylenediamine, 2-Nitro-p-Phenylenediamine, Picramic Acid, HC Red No. 13, 1,4-Bis-(2'-Hydroxyethyl)-amino-2-nitrobenzene, HC Yellow No. 5, HC Red No. 7, HC Blue No. 2, HC Yellow No. 4, HC Yellow No. 2, HC Orange No. 1, HC Red No. 1, 2-Chloro-5-nitro-N-Hydroxyethyl-p-phenylenediamine, HC Red No. 3, 4-Amino-3-nitrophenol, 2-Hydroxyethylamino-5-nitroanisole, 3-nitro-p-Hydroxyethylaminophenol, 2-amino-3-nitrophenol, 6-nitro-o-toluidine, 3-methylamino-4-nitrophenoxyethanol, 2-nitro-5-glycerymethylanaline, HC Yellow No. 11, HC Violet No. 1, HC Orange No. 2, HC Orange No. 3, HC Yellow No. 9, 4-Nitrophenyl Aminoethylurea, HC Red No. 10, HC Red No. 11, 2-Hydroxyethyl picramic acid, HC Blue No. 12, HC Yellow No. 6, Hydroxyethyl-2-nitro-p-toluidine, HC Yellow No. 12, HC Blue No. 10, HC Yellow No. 7, HC Yellow No. 10, HC Blue No. 9, N-ethyl-3-nitro PABA, 4-amino-2-nitrophenyl-amine-2'-carboxylic acid, 2-chloro-6-ethylamino-4-nitrophenol, 6-Nitro-2,5-pyridinediamine, HC Violet No. 2, 2-amino-6chloro-4-nitrophenol, 4-hydroxypropylamino-3-nitrophenol, HC Yellow No. 13, 1,2,3,4-Tetrahydro-6-nitrochinoxalin, HC Red No. 14, HC Yellow No. 15, HC Yellow No. 14, 3-Amino-6-methylamino-2-nitropyridine, 2,6-diamino-3-((pyridine-3-yl)azo)pyridine, Basic Red No. 118, Basic Orange No. 69, N-(2-nitro-4-aminophenyl)-allylamine, 4-[(4-Amino-3-methylphenyl)(4-Imino-3-methyl-2,5-Cyclohexadien-1-ylidene) Methyl]-2-Methyl-benzeneamine-Hydrochloride, 1H-Imidazolium,2-[[4-(dimethyl-amino)phenyl]azo]-1,3-dimethylchloride, Pyridinium, 1-methyl-4-[(methylphenylhydrazono)methyl]-, methyl sulfate, 1H-Imidazolium, 2-[(4-aminophenyl)azo]-1,3-dimethyl, chloride, Basic Red 22, Basic Red 76, Basic Brown 16, Basic Yellow 57, 7-(2',4'-Dimethyl-5'-sulfophenylazo)-5-sulfo-8-hydroxynaphthalene, Acid Orange 7, Acid Red 33, 1-(3'-Nitro-5'-sulfo-6'-oxophenylazo)-oxo-naphthalene chromium complex, Acid Yellow 23, Acid Blue 9, Basic Violet 14, Basic Blue 7, Basic Blue 26, Sodium salt of mixture of mono- & disulfonic acids (mainly the latter) of quinophthlanone or 2-quinolylindandione, Basic Red 2, Basic Blue 99, Disperse Red 15, Acid Violet 43, Disperse Violet 1, Acid Blue 62, Pigment Blue 15, Acid Black 132, Basic Yellow 29, Disperse Black 9, 1-(N-Methylmorpholinium-propylamino)-4-hydroxy-anthraquinone methylsulfate, HC Blue No. 8, HC Red No. 8, HC Green No. 1, HC Red No. 9, 2-Hydroxy-1,4-naphthoquinone, Acid Blue 199, Acid Blue 25, Acid Red 4, Henna Red, Indigo, Cochenille, HC Blue 14, Disperse Blue 23, Disperse Blue 3, Violet 2, Disperse Blue 377, Basic Red 51, Basic Orange 31, Basic Yellow 87, and mixtures thereof. Preferred direct dyes include but are not limited to: Disperse Black 9, HC Yellow 2, HC Yellow 4, HC Yellow 15, 4-nitro-o-phenylenediamine, 2-amino-6-chloro-4-nitrophenol, HC Red 3, Disperse Violet 1, HC Blue 2, Disperse Blue 3, Disperse Blue 377, Basic Red 51, Basic Orange 31, Basic Yellow 87, and mixtures thereof.

E. Oxidizing Agent

The inventive compositions may comprise an oxidizing agent, present in an amount sufficient to bleach melanin pigment in hair and/or cause formation of dye chromophores from oxidative dye precursors (including developers and/or couplers when present). Typically, such an amount ranges from 1% to 20%, preferably from 3% to 15%, more preferably from 6% to 12%, by weight, of the developer composition. Inorganic peroxygen materials capable of yielding hydrogen peroxide in an aqueous medium are preferred, and include but are not limited to: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal salts of perborates, percarbonates, perphosphates, persilicates, and persulphates, preferably sodium salts thereof), which may be incorporated as monohydrates, tetrahydrates, etc.; alkali metal bromates; enzymes; and mixtures thereof. Preferred is hydrogen peroxide.

F. Thickeners

The inventive compositions may comprise a thickener in an amount sufficient to provide the composition with a viscosity so that it can be readily applied to the hair without unduly dripping off the hair and causing mess. Typically, such an amount will be at least 0.1%, preferably at least 0.5%, more preferably, at least 1%, by weight, of the composition.

Preferred for use herein are salt tolerant thickeners, including but not limited to: xanthan, guar, hydroxypropyl guar, scleroglucan, methyl cellulose, ethyl cellulose (available as AQUACOTE (™)), hydroxyethyl cellulose (NATROSOL (™)), carboxymethyl cellulose, hydroxypropylmethyl cellulose, microcrystalline cellulose, hydroxybutyl-methyl cellulose, hydroxypropyl cellulose (available as KLUCEL (™)), hydroxyethyl ethyl cellulose, cetyl hydroxyethyl cellulose (available as NATROSOL (™) Plus 330), N-vinylpyrollidone (available as POVIDONE (™)), Acrylates/Ceteth-20 Itaconate Copolymer (available as STRUCTURE (™) 3001), hydroxypropyl starch phosphate (available as STRUCTURE (™) ZEA), polyethoxylated urethanes or polycarbamyl polyglycol ester (e.g. PEG-150/Decyl/SMDI copolymer (available as ACULYN(™) 44), PEG-150/Stearyl/SMDI copolymer available as ACULYN(™) 46), trihydroxystearin (available as THIXCIN(™)), acrylates copolymer (e.g. available as ACULYN(™) 33) or hydrophobically modified acrylate copolymers (e.g. Acrylates/Steareth-20 Methacrylate Copolymer (available as ACULYN(™) 22), non-ionic amphophilic polymers comprising at least one fatty chain and at least one hydrophilic unit selected from polyether urethanes comprising at least one fatty chain, and blends of Ceteth-10 phosphate, Dicetyl phosphate and Cetearyl alcohol (available as CRODAFOS(™) CES).

G. Chelants

The inventive compositions may comprise chelants in an amount sufficient to reduce the amount of metals available to interact with formulation components, particularly oxidizing agents, more particularly peroxides. Typically such an amount will range from at least 0.25%, preferably at least 0.5%, by weight, of the composition. Suitable chelants for use herein include but are not limited to: diamine-N,N'-dipolyacid, monoamine monoamide-N,N'-dipolyacid, and N,N'-bis(2-hydroxybenzyl)ethylenediamine-N,N'-diacetic acid chelants (preferably EDDS (ethylenediaminedisuccinic acid)), carboxylic acids (preferably aminocarboxylic acids), phosphonic acids (preferably aminophosphonic acids) and polyphosphoric acids (in particular straight polyphosphoric acids), their salts and derivatives.

H. pH Modifiers and Buffering Agents

The inventive compositions may further comprise a pH modifier and/or buffering agent in an amount that is sufficiently effective to adjust the pH of the composition to fall within a range from 3 to 13, preferably from 8 to 12, more preferably from 9 to 11. Suitable pH modifiers and/or buffering agents for use herein include, but are not limited to: ammonia, alkanolamides such as monoethanolamine, diethanolamine, triethanolamine, monopropanolaamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, preferably sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

I. Carbonate Ion Source and Radical Scavenger System

The inventive compositions may comprise a system comprising a source of carbonate ions, carbamate ions and or hydrocarbonate ions, and a radical scavenger, in a sufficient amount to reduce damage to the hair during the coloring process. Typically, such an amount will range from 0.1% to 15%, preferably 0.1% to 10%, more preferably 1% to 7%, by weight of the composition, of the carbonate ion, and from 0.1% to 10%, preferably from 1% to 7%, by weight of the composition, of radical scavenger. Preferably, the radical scavenger is present at an amount such that the ratio of radical scavenger to carbonate ion is from 1:1 to 1:4. The radical scavenger is preferably selected such that it is not an identical species as the alkalizing agent.

Suitable sources for the ions include but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Preferred sources of carbonate ions are sodium hydrogen carbonate and potassium hydrogen carbonate. Also preferred are ammonium carbonate, and ammonium hydrogen carbonate.

The radical scavenger is a species that can react with a carbonate radical to convert the carbonate radical by a series of fast reactions to a less reactive species. Preferably, when the radical scavenger comprises an N atom, it has a pKa>7 to prevent the protonation of the nitrogen. Preferred radical scavengers may be selected from the classes of alkanolamines, amino sugars, amino acids and mixtures thereof, and may include, but are not limited to: monoethanolamine, 3-amino-1-propanol, 4-amino-1-butanol,5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan and potassium, sodium and ammonium salts of the above and mixtures thereof. Other preferred radical scavenger compounds include benzylamine, glutamic acid, imidazole, di-tert-butylhydroxytoluene, hydroquinone, catechol and mixtures thereof.

III. Methods of Manufacture

The compounds of this invention may be obtained using conventional methods. A general description of how to make the compounds is provided above and specific examples are provided below. The compositions of this invention may also be obtained using conventional methods. The keratin dyeing compositions may be formed as solutions, preferably as aqueous or aqueous-alcohol solutions. The hair dye product compositions may preferably be formed as thick liquids, creams, gels, or emulsions whose composition is a mixture of the dye compound and other dye ingredients with conventional cosmetic additive ingredients suitable for the particular preparation.

IV. Methods of Use

The inventive keratin dyeing compositions may be used by admixing them with a suitable oxidant, which reacts with the oxidative dye precursors to develop the hair dye product composition. The oxidant is usually provided in an aqueous composition, which normally is provided as a separate component of the finished keratin dyeing product system and present in a separate container. Upon mixing the keratin dyeing composition, the adjuvants are provided in the hair dye composition as it is applied to the hair to achieve desired product attributes, e.g., pH, viscosity, rheology, etc.

The keratin dyeing composition, as it is applied to the hair, can be weakly acidic, neutral or alkaline according to their composition, typically having a pH from 6 to 11, preferably from 7 to 10, more preferably from 8 to 10. The pH of the developer composition is typically acidic, and generally the pH is from 2.5 to 6.5, preferably from 3 to 5. The pH of the hair compositions may be adjusted using a pH modifier as mentioned above.

In order to use the keratin dyeing composition, the above-described compositions are mixed immediately prior to use and a sufficient amount of the mixture is applied to the hair, according to the hair abundance, generally from 60 to 200 grams. Upon such preparation the hair dye composition is applied to the hair to be dyed and remains in contact with the hair for an amount of time effective to dye the hair. Typically, the hair dye composition is allowed to act on the hair for 2 to 60, preferably 15 to 45, more preferably, 30 minutes, at a temperature ranging from 15° to 50° C. Thereafter, the hair is rinsed with water, to remove the hair dye composition and dried. If necessary, the hair is washed with a shampoo and rinsed, e.g., with water or a weakly acidic solution, such as a citric acid or tartaric acid solution, and dried. Optionally, a separate conditioning product may also be provided.

Together, components of the keratin dyeing composition form a system for dyeing hair. This system may be provided as a kit comprising in a single package separate containers of the keratin dyeing composition components or other hair treatment product, and instructions for use.

EXAMPLES

The following are non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified.

The following compositions can be used for dyeing hair. The dyeing composition is mixed with an equal weight of a 20-volume hydrogen peroxide solution (6% by weight). The resulting mixture is applied to the hair and permitted to remain in contact with the hair for 30 minutes. This dyed hair is then shampooed and rinsed with water and dried.

Common base (CB) for dyeing

| Ingredients | Weight (g) |
|---|---|
| Propylene glycol | 9.5 |
| Ammonium hydroxide | 5 |
| Ethoxydiglycol | 4 |
| Ethanolamine | 4.5 |
| Oleic acid | 1 |
| Hexylene glycol | 6 |
| Cocamidopropyl betaine | 3.5 |
| Oleth-10 | 0.3 |
| Oleth-2 | 0.3 |
| Dilinoleic acid | 1.5 |
| C12-C15 Pareth-3 | 0.5 |
| Soytrimonium chloride | 7 |
| Sodium metasilicate | 0.05 |
| Erythorbic acid | 0.5 |
| EDTA | 0.03 |
| Sodium sulfite | 0.3 |
| 1-Phenyl-3-methyl-5-pyrazolone | 0.2 |

| Ingredients | 1 | 2 | 3 | 4 | 5 | 6 | 7 |
|---|---|---|---|---|---|---|---|
| 1-Ethoxy-4-methyl-1,4-dihydro-pyrrolo[3,2-b]pyrrole-2,5-diamine | 0.05 | 0.04 | 0.03 | 0.01 | 0.05 | 0.15 | 0.2 |
| N,N-Bis(2-hydroxyethyl)-p-phenylendiamine | 0.1 | | | | | | 0.02 |
| 4-Aminophenol | 0.2 | 0.02 | 0.3 | | 0.2 | 0.4 | |
| 4-Amino-2-methylphenol | | | | 0.4 | | | 0.2 |
| 3-Aminophenol | 0.1 | | | | | | |
| 5-Amino-2-methylphenol | | | 0.02 | 0.02 | | 0.02 | 0.04 |
| 1-Naphthol | 0.05 | | | | | | |
| Resorcinol | 0.15 | 0.1 | 0.1 | 0.4 | 0.1 | 0.5 | 0.4 |
| 2-Methylresorcinol | | | 0.4 | | | | |
| 1-Hydroxyethyl-4,5-diaminopyrazole | | | | | | 0.2 | |
| Common base (CB) | 44.18 | 44.18 | 44.18 | 44.18 | 44.18 | 44.18 | 44.18 |
| Water | qs | qs | qs | qs | qs | qs | qs |

| Ingredients | 8 | 9 | 10 | 11 | 12 | 13 | 14 |
|---|---|---|---|---|---|---|---|
| Furo[3,2-b]pyrrole-2,4,5-triamine | 0.3 | 0.2 | 0.2 | 0.1 | 0.1 | 0.2 | 0.6 |
| N,N-Bis(2-hydroxyethyl)-p-phenylendiamine | 0.33 | 0.02 | | | | | |
| 4-Aminophenol | 0.5 | | 0.7 | | 0.9 | 1.2 | 0.3 |
| 4-Amino-2-methylphenol | | 1 | | 1.2 | | | |
| 3-Aminophenol | 0.3 | | | | | | |
| 5-Amino-2-methylphenol | | 0.4 | 0.4 | 2.5 | 2.5 | 1 | 0.8 |
| 1-Naphthol | | | | | | | |
| Resorcinol | 0.3 | 0.1 | 0.1 | 0.1 | 0.1 | 0.6 | 0.1 |
| 2-Methylresorcinol | 0.4 | 0.6 | 0.6 | | | | |
| 1-Hydroxyethyl-4,5-diaminopyrazole | | | | 0.2 | 0.2 | 0.4 | |
| Common base (CB) | 44.18 | 44.18 | 44.18 | 44.18 | 44.18 | 44.18 | 44.18 |
| Water | qs | qs | qs | qs | qs | qs | qs |

| Ingredients | 15 | 16 | 17 | 18 | 19 | 20 | 21 |
|---|---|---|---|---|---|---|---|
| Thieno[3,2-b]pyrrole-2,4-diamine | 0.3 | 0.5 | 0.4 | 0.3 | | | |
| 6H-pyrrolo[2,3-b]pyrrole-1,3-diamine | | | | | 0.5 | 0.4 | 0.3 |
| N,N-Bis(2-hydroxyethyl)-p-phenylendiamine | 0.1 | 0.1 | 0.3 | | 0.1 | 0.3 | |
| p-Phenylenediamine | | | | 0.4 | | | 0.4 |
| 4-Aminophenol | 0.5 | | 0.1 | 0.2 | | 0.1 | 0.2 |
| 4-Amino-2-methylphenol | | 1 | | | 1 | | |
| 3-Aminophenol | 0.3 | | 0.2 | | | 0.2 | |
| 5-Amino-2-methylphenol | | 0.4 | 0.2 | 0.5 | 0.4 | 0.2 | 0.5 |
| 1-Naphthol | | | 0.1 | | | 0.1 | |
| Resorcinol | 0.3 | 0.2 | 0.4 | 0.3 | 0.2 | 0.4 | 0.3 |
| 2-Methylresorcinol | 0.4 | 0.2 | | | 0.2 | | |
| 1-Hydroxyethyl-4,5-diaminopyrazole | | | 0.5 | 0.1 | 0.3 | 0.5 | 0.1 | 0.3 |
| Common base (CB) | 44.18 | 44.18 | 44.18 | 44.18 | 44.18 | 44.18 | 44.18 |
| Water | qs | qs | qs | qs | qs | qs | qs |

-continued

| Ingredients | 22 | 23 | 24 | 25 | 26 | 27 | 28 |
|---|---|---|---|---|---|---|---|
| N4,N4-diethyl-furo[3,2-b]pyrrole-3,4-diamine | 0.3 | 0.5 | 0.4 | 0.3 | | | |
| 4-methoxy-4H-thieno[3,2-b]pyrrol-3-ylamine | | | | | 0.5 | 0.4 | 0.3 |
| N,N-Bis(2-hydroxyethyl)-p-phenylendiamine | 0.1 | 0.1 | 0.3 | | 0.1 | 0.3 | |
| p-Phenylenediamine | | | | 0.4 | | | 0.4 |
| 4-Aminophenol | 0.5 | | 0.1 | 0.2 | | 0.1 | 0.2 |
| 4-Amino-2-methylphenol | | 1 | | | 1 | | |
| 3-Aminophenol | 0.3 | | 0.2 | | | 0.2 | |
| 5-Amino-2-methylphenol | | 0.4 | 0.2 | 0.5 | 0.4 | 0.2 | 0.5 |
| 1-Naphthol | | | 0.1 | | | 0.1 | |
| Resorcinol | 0.3 | 0.2 | 0.4 | 0.3 | 0.2 | 0.4 | 0.3 |
| 2-Methylresorcinol | 0.4 | 0.2 | | | 0.2 | | |
| 1-Hydroxyethyl-4,5-diaminopyrazole | | 0.5 | 0.1 | 0.3 | 0.5 | 0.1 | 0.3 |
| Common base (CB) | 44.18 | 44.18 | 44.18 | 44.18 | 44.18 | 44.18 | 44.18 |
| Water | qs | qs | qs | qs | qs | qs | qs |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All documents cited in the Background, Summary of the Invention, and Detailed Description of the Invention are, in relevant part, incorporated herein by reference; the citation of any document is not to be construed as an admission that it is prior art with respect to the present invention.

What is claimed is:

1. A keratin dyeing composition comprising:
   (A) a medium suitable for dyeing; and
   (B) at least one bicyclic fused 5-5-membered aza heteroaromatic keratin dyeing compounds with an N-hydroxy or N-amino group and derivatives thereof, according to the following formulas:

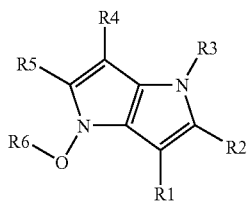

I

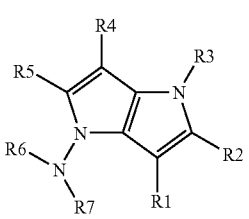

II

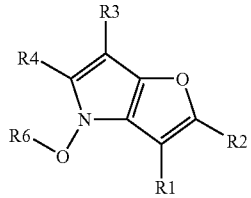

III

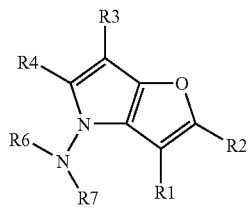

IV

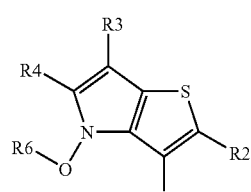

V

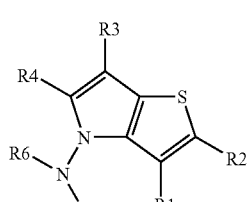

VI

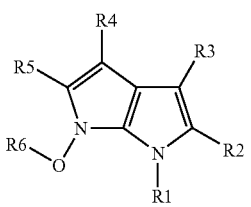

VII

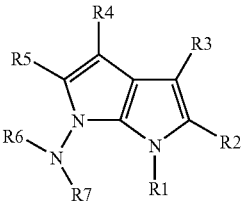

VIII

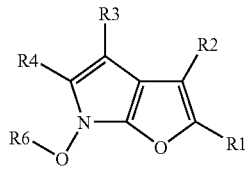

IX

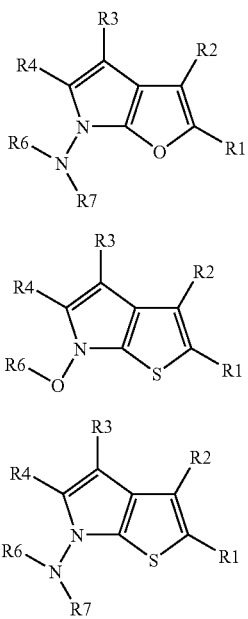

wherein R1, R2, R3, R4, R5, R6, and R7 are the same or different and are selected from the group consisting of:
(a) C-linked monovalent substituents selected from the group consisting of:
  (i) substituted or unsubstituted, straight or branched, alkyl, mono- or poly-unsaturated alkyl, heteroalkyl, aliphatic, heteroaliphatic, or heteroolefinic systems,
  (ii) substituted or unsubstituted, mono- or poly-cyclic aliphatic, aryl, or heterocyclic systems, and
  (iii) substituted or unsubstituted, mono-, poly-, or per-fluoro alkyl systems; wherein said systems of (i), (ii) and (iii) comprise from about 1 to about 10 carbon atoms and from about 0 to about 5 heteroatoms selected from the group consisting of O, S, N, P, and Si;
(b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked monovalent substituents selected from the group consisting of $OA^1$, and $ONA^1A^2$;
(d) N-linked monovalent substituents selected from the group consisting of $NA^1A^2$, $(NA^1A^2A^3)^+$, $NA^1OA^2$, $NA^{SA2}$, $NO_2$, $N=NA^1$, $N=NOA^1$, $NA^1CN$, and $NA^1NA^2A^3$;
(e) monovalent substituents selected from the group consisting of $COOA^1$, $CONA^1_2$, $CONA^1COA^2$, $C(=NA^1)NA^1A^2$, CN, and X; and
(f) fluoroalkyl monovalent substituents selected from the group consisting of mono-, poly-, and per-fluoro alkyl systems comprising from about 1 to about 12 carbon atoms and from about 0 to about 4 heteroatoms;
(g) hydrogen;
wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, or per-fluoro alkyl systems, or $A^1$ and $A^2$ together with nitrogen atoms to which they are bound form a ring; wherein said systems comprise from about 1 to about 10 carbon atoms and from about 0 to about 5 heteroatoms selected from the group consisting of O, S, N, P, and Si;
wherein X is a halogen selected from the group consisting of F, Cl, Br, and I.

2. The composition of claim 1 wherein said, $R^1$, $R^2$, $R^3$, $R^4$, $R^5$, $R^6$, and $R^7$ are selected from the group consisting of a hydrogen atom; a halogen atom; an amino substituent, a hydroxyl substituent; a cyano substituent; a $C1-C_4$ alkyl substituent; a trifluoromethyl substituent, an alkylamino substituent; a hydroxyalkylamino substituent; an acetylamido substituent; a carboxyl substituent or its esters; an alkoxy substituent; an alkoxyalkyl substituent; a carbamoyl substituent; an alkylcarbamoylsubstituent; a hydroxyalkylcarbamoyl substituent; an amido substituent; an alkylamido substituent; an alkylcarbonyl substituent; an alkoxycarbonyl substituent; an aryloxy substituent; an acyloxy substituent; an alkylthio substituent; an arylthio substituent; a heteroarylthio substituent; a heteroaryloxy substituent; a 3-, 4-, 5-, 6-, or 7-membered heterocycle having at least one nitrogen, oxygen or sulfur atom; an aryl substituent; a sulfonyl substituent; a sulfinyl substituent; a phosphonyl substituent; a sulfamoyl substituent; a siloxy substituent; an acyloxy substituent; a carbamoyloxy substituent; a sulphonamide substituent; an imide substituent; a ureido substituent; a sulfamoylamino substituent; an alkoxycarbonylamino substituent; an aryloxycarbonylamino substituent; an aryloxycarbonyl substituent; and a benzenesulfonamido substituent.

3. The composition of claim 1 wherein at least one of said $R^1$, $R^2$, $R^3$, and $R^4$ is an amino group and at least one of the remaining said $R^1$, $R^2$, $R^3$, and $R^4$ is selected from the group consisting of amino, hydroxyl, a 3-, 4-, 5-, 6-, or 7-membered heterocycle having at least one nitrogen, oxygen or sulfur atom, Alkylamino (linear or branched C1-C5), Dialkylamino (linear or branched C1-C5), Hydroxyalkylamino (linear or branched C1-C5), Dihydroxyalkylamino (linear or branched C1-C5), Arylamino or substituted arylamino; Heteroarylamino or substituted heteroarylamino; Arylmethylamino or substituted arylmethylamino; and Heteroarylmethylamino or substituted heteroarylmethylamino, wherein substituents are selected from the group consisting of halogen, C1-C5 alkyl, C1-C5 alkoxy, trifluoromethyl, amino, and C1-C5 alkylamino.

4. The composition of claim 1 wherein at least one of said $R^1$, $R^2$, $R^3$, and $R^4$ is selected from the group consisting of hydrogen, Amino, Hydroxyl, Alkylamino (linear or branched C1-C5), Hydroxyalkylamino (linear or branched C1-C5), Arylamino or substituted arylamino; Heteroarylamino or substituted heteroarylamino; Arylmethylamino or substituted arylmethylamino; and Heteroarylmethylamino or substituted heteroarylmethylamino, wherein substituents are selected from the group consisting of halogen, C1-C5 alkyl, C1-C5 alkoxy, trifluoromethyl, amino, and C1-C5 alkylamino.

5. The composition of claim 1 wherein at least one of said $R^1$, $R^2$, $R^3$, $R^4$, $R^5$, $R^6$, and $R^7$ is selected from the group consisting of hydrogen, chlorine, cyano, alkoxy, phenoxy, methylsulfonyoxy, pyridone and pyridazone.

6. The composition of claim 1 wherein said bicyclic fused 5-5-membered aza heteroaromatic keratin dyeing compounds with an N-hydroxy or N-amino group and derivatives thereof are selected from the group consisting of pyrrolo[3,2-b]pyrrole, furo[3,2-b]pyrrole, thieno[3,2-b]pyrrole, pyrrolo[2,3-b]pyrrole, furo[2,3-b]pyrrole, and thieno[2,3-b]pyrrole.

7. The composition of claim 6 wherein said pyrrolo[3,2-b]pyrroles are selected from the group consisting of 2,5-Diamino-4H-pyrrolo[3,2-b]pyrrol-1-ol, 2,5-diamino-4-methyl-4H-pyrrolo[3,2-b]pyrrol-1-ol, 1-methoxy-4-methyl-1,4-dihydro-pyrrolo[3,2-b]pyrrole-2,5-diamine, 1-ethoxy-4-methyl-1,4-dihydro-pyrrolo[3,2-b]pyrrole-2,5-diamine, 2-(2,5-diamino-4-methyl-4H-pyrrolo[3,2-b]pyrrol-1-yloxy)-ethanol, 2-(5-amino-2-ethylamino-4-methyl-4H-pyrrolo[3,2-b]pyrrol-1-yloxy)-ethanol, 4, N1-dimethyl-4H-pyrrolo[3,2-b]pyrrole-1,2,5-triamine, N1-ethyl-4-methyl-4H-pyrrolo[3,2-b]pyrrole-1,2,5-triamine, 2-(2,5-diamino-4-methyl-4H-pyrrolo[3,2-b]pyrrol-1-ylamino)-ethanol, 2-(5-amino-2-ethylamino-4-methyl-4H-pyrrolo[3,2-b]pyrrol-1-ylamino)-ethanol, 2-[5-amino-2-(2-hydroxy-ethylamino)-4-methyl-4H-pyrrolo[3,2-b]pyrrol-1-ylamino]-ethanol, 2-{5-amino-2-[bis-(2-hydroxy-ethyl)-amino]-4-methyl-4H-pyrrolo[3,2-b]pyrrol-1-ylamino}-ethanol, 2-(5-amino-4-methyl-2-pyrrolidin-1-yl-4H-pyrrolo[3,2-b]pyrrol-1-ylamino)-ethanol, 4N5-dimethyl-4H-pyrrolo[3,2-b]pyrrole-1,2,5-triamine, N5-ethyl-4,N1-dimethyl-4H-pyrrolo[3,2-b]pyrrole-1,2,5-triamine, 2-[(5-amino-1-methyl-4-methylamino-1,4-dihydro-pyrrolo[3,2-b]pyrrol-2-yl)-(2-hydroxy-ethyl)-amino]-ethanol, 2-(2-amino-4-methyl-5-pyrrolidin-1-yl-4H-pyrrolo[3,2-b]pyrrol-1-ylamino)-ethanol, 4N1,N1-trimethyl-4H-pyrrolo[3,2-b]pyrrole-1,2,5-triamine, N1,N1-diethyl-4-methyl-4H-pyrrolo[3,2-b]pyrrole-1,2,5-triamine, 2-[(2,5-diamino-4-methyl-4H-pyrrolo[3,2-b]pyrrol-1-yl)-(2-hydroxy-ethyl)-amino]-ethanol, 1-methyl-4-pyrrolidin-1-yl-1,4-dihydro-pyrrolo[3,2-b]pyrrole-2,5-diamine, 2-[(5-amino-4-methyl-2-pyrrolidin-1-yl-4H-pyrrolo[3,2-b]pyrrol-1-yl)-(2-hydroxy-ethyl)-amino]-ethanol, and 2-[(2-amino-4-methyl-5-pyrrolidin-1-yl-4H-pyrrolo[3,2-b]pyrrol-1-yl)-methyl-amino]-ethanol.

8. The composition of claim 6 wherein said pyrrolo[3,2-b]pyrroles are selected from the group consisting of 4H-pyrrolo[3,2-b]pyrrol-1-ol, 1-methoxy-1,4-dihydro-pyrrolo[3,2-b]pyrrole, 1-ethoxy-1,4-dihydro-pyrrolo[3,2-b]pyrrole, 2-(4H-pyrrolo[3,2-b]pyrrol-1-yloxy)-ethanol, 1-isopropoxy-1,4-dihydro-pyrrolo[3,2-b]pyrrole, 4H-pyrrolo[3,2-b]pyrrole-1,2-diol, 1-methoxy-4-methyl-1,4-dihydro-pyrrolo[3,2-b]pyrrol-2-ol, 4H-pyrrolo[3,2-b]pyrrole-1,5-diol, 4-methyl-4H-pyrrolo[3,2-b]pyrrole-1,5-diol, 4-methoxy-1,4-dihydro-pyrrolo[3,2-b]pyrrol-2-ol, 4-methoxy-1-methyl-1,4-dihydro-pyrrolo[3,2-b]pyrrol-2-ol, 4-methyl-4H-pyrrolo[3,2-b]pyrrole-1,6-diol, 4-methoxy-1-methyl-1,4-dihydro-pyrrolo[3,2-b]pyrrol-3-ol, 4H-pyrrolo[3,2-b]pyrrole-1,3-diol, 1-methoxy-4-methyl-1,4-dihydro-pyrrolo[3,2-b]pyrrol-3-ol, 3-amino-4H-pyrrolo[3,2-b]pyrrol-1-ol, 1-methoxy-4-methyl-1,4-dihydro-pyrrolo[3,2-b]pyrrol-3-ylamine, 6-amino-4H-pyrrolo[3,2-b]pyrrol-1-ol, 4-methoxy-1-methyl-1,4-dihydro-pyrrolo[3,2-b]pyrrol-3-ylamine, 5-amino-4H-pyrrolo[3,2-]pyrrol-1-ol, and 4-methoxy-1-methyl-1,4-dihydro-pyrrolo[3,2-b]pyrrol-2-ylamine.

9. The composition of claim 6 wherein said furo[3,2-b]pyrroles are selected from the group consisting of 2,5-diamino-furo[3,2-b]pyrrol-4-ol, 2,5-diamino-furo[3,2-b]pyrrol-4-ol, 4-methoxy-4H-furo[3,2-b]pyrrole-2,5-diamine, 4-ethoxy-4H-furo[3,2-b]pyrrole-2,5-diamine, 2-(2,5-diamino-furo[3,2-b]pyrrol-4-yloxy)-ethanol, 2-(2-amino-5-ethylamino-furo[3,2-b]pyrrol-4-yloxy)-ethanol, 2-[2-amino-5-(2-hydroxy-ethylamino)-furo[3,2-b]pyrrol-4-yloxy]-ethanol, 2-{2-amino-5-[bis-(2-hydroxy-ethyl)-amino]-furo[3,2-b]pyrrol-4-yloxy}-ethanol, 2-(2-amino-5-pyrrolidin-1-yl-furo[3,2-b]pyrrol-4-yloxy)-ethanol, 5-amino-2-methylamino-furo[3,2-b]pyrrol-4-ol, N2-ethyl-4-methoxy-4H-furo[3,2-b]pyrrole-2,5-diamine, 2-[(5-amino-4-methoxy-4H-furo[3,2-b]pyrrol-2-yl)-(2-hydroxy-ethyl)-amino]-ethanol, 2-(5-amino-2-pyrrolidin-1-yl-furo[3,2-b]pyrrol-4-yloxy)-ethanol, furo[3,2-b]pyrrole-2,4,5-triamine, N4-methyl-furo[3,2-b]pyrrole-2,4,5-triamine, N4-ethyl-furo[3,2-b]pyrrole-2,4,5-triamine, 2-(2,5-diamino-furo[3,2-b]pyrrol-4-ylamino)-ethanol, 2-(2-amino-5-ethylamino-furo[3,2-b]pyrrol-4-ylamino)-ethanol, 2-[2-amino-5-(2-hydroxy-ethylamino)-furo[3,2-b]pyrrol-4-ylamino]-ethanol, 2-{2-amino-5-[bis-(2-hydroxy-ethyl)-amino]-furo[3,2-b]pyrrol-4-ylamino}-ethanol, 2-(2-amino-5-pyrrolidin-1-yl-furo[3,2-b]pyrrol-4-ylamino)-ethanol, 2-[(2-Amino-5-pyrrolidin-1-yl-furo[3,2-b]pyrrol-4-yl)-hydroxyethyl-amino]-ethanol, N2-methyl-furo[3,2-b]pyrrole-2,4,5-triamine, N2-ethyl-N4-methyl-furo[3,2-b]pyrrole-2,4,5-triamine, 2-[(5-amino-4-pyrrolidin-1-yl-4H-furo[3,2-b]pyrrol-2-yl)-(2-hydroxy-ethyl)-amino]-ethanol, 2-[(5-amino-2-pyrrolidin-1-yl-furo[3,2-b]pyrrol-4-yl)-methyl-amino]-ethanol, and 2-[(5-amino-2-pyrrolidin-1-yl-furo[3,2-b]pyrrol-4-yl)-(2-hydroxy-ethyl)-amino]-ethanol.

10. The composition of claim 6 wherein said furo[3,2-b]pyrroles are selected from the group consisting of furo[3,2-b]pyrrole-4,5-diol, 4-methoxy-4H-furo[3,2-b]pyrrol-5-ol, furo[3,2-b]pyrrole-4,6-diol, 4-methoxy-4H-furo[3,2-b]pyrrol-6-ol, furo[3,2-b]pyrrole-2,4-diol, 4-methoxy-4H-furo[3,2-b]pyrrol-2-ol, 4-ethoxy-4H-furo[3,2-b]pyrrol-2-ol, 4-amino-4H-furo[3,2-b]pyrrol-5-ol, 4-methylamino-4H-furo[3,2-b]pyrrol-5-ol, 4-diethylamino-4H-furo[3,2-b]pyrrol-5-ol, 4-amino-4H-furo[3,2-b]pyrrol-6-ol, 4-methylamino-4H-furo[3,2-b]pyrrol-6-ol, and 4-diethylamino-4H-furo[3,2-b]pyrrol-6-ol.

11. The composition of claim 6 wherein said thieno[3,2-b]pyrroles are selected from the group consisting of 2,5-diamino-thieno[3,2-b]pyrrol-4-ol, 2,5-diamino-thieno[3,2-b]pyrrol-4-ol, 4-methoxy-4H-thieno[3,2-b]pyrrole-2,5-diamine, 4-ethoxy-4H-thieno[3,2-b]pyrrole-2,5-diamine, 2-(2,5-diamino-thieno[3,2-b]pyrrol-4-yloxy)-ethanol, 2-(2-amino-5-ethylamino-thieno[3,2-b]pyrrol-4-yloxy)-ethanol, 2-[2-amino-5-(2-hydroxy-ethylamino)-thieno[3,2-b]pyrrol-4-yloxy]-ethanol, 2-{2-amino-5-[bis-(2-hydroxy-ethyl)-amino]-thieno[3,2-b]pyrrol-4-yloxy}-ethanol, 2-(2-amino-5-pyrrolidin-1-yl-thieno[3,2-b]pyrrol-4-yloxy)-ethanol, 5-amino-2-methylamino-thieno[3,2-b]pyrrol-4-ol, N2-ethyl-4-methoxy-4H-thieno[3,2-b]pyrrole-2,5-diamine, 2-[(5-amino-4-methoxy-4H-thieno[3,2-b]pyrrol-2-yl)-(2-hydroxy-ethyl)-amino]-ethanol, 2-(5-amino-2-pyrrolidin-1-yl-thieno[3,2-b]pyrrol-4-yloxy)-ethanol, thieno[3,2-b]pyrrole-2,4,5-triamine, N4-methyl-thieno[3,2-b]pyrrole-2,4,5-triamine, N4-ethyl-thieno[3,2-b]pyrrole-2,4,5-triamine, 2-(2,5-diamino-thieno[3,2-b]pyrrol-4-ylamino)-ethanol, 2-(2-amino-5-ethylamino-thieno[3,2-b]pyrrol-4-ylamino)-ethanol, 2-[2-amino-5-(2-hydroxy-ethylamino)-thieno[3,2-b]pyrrol-4-ylamino]-ethanol, 2-{2-amino-5-[bis-(2-hydroxy-ethyl)-amino]-thieno[3,2-b]pyrrol-4-ylamino}-ethanol, 2-(2-amino-5-pyrrolidin-1-yl-thieno[3,2-b]pyrrol-4-ylamino)-ethanol, 2-[(2-amino-5-pyrrolidin-1-yl-thieno[3,2-b]pyrrol-4-yl)-(2-hydroxy-ethyl)-amino]-ethanol, N2-methyl-thieno[3,2-b]pyrrole-2,4,5-triamine, N2-ethyl-N4-methyl-thieno[3,2-b]pyrrole-2,4,5-triamine, 2-[(5-amino-4-pyrrolidin-1-yl-4H-thieno[3,2-b]pyrrol-2-yl)-(2-hydroxy-ethyl)-amino]-ethanol, 2-[(5-amino-2-pyrrolidin-1-yl-thieno[3,2-b]pyrrol-4-yl)-methyl-amino]-ethanol, and 2-[(5-amino-2-pyrrolidin-1-yl-thieno[3,2-b]pyrrol-4-yl)-(2-hydroxy-ethyl)-amino]-ethanol.

12. The composition of claim 6 wherein said thieno[3,2-b]pyrroles are selected from the group consisting of thieno[3,2-b]pyrrole-4,5-diol, 4-methoxy-4H-thieno[3,2-b]pyrrol-5-ol, thieno[3,2-b]pyrrole-4,6-diol, 4-methoxy-4H-thieno[3,2-b]pyrrol-6-ol, 4-amino-4H-thieno[3,2-b]pyrrol-5-ol, 4-methylamino-4H-thieno[3,2-b]pyrrol-5-ol, 4-diethylamino-4H-thieno[3,2-b]pyrrol-5-ol, 4-amino-4H-thieno[3,2-b]pyrrol-6-ol, 4-methylamino-4H-thieno[3,2-b]pyrrol-6-ol, and 4-diethylamino-4H-thieno[3,2-b]pyrrol-6-ol.

13. The composition of claim 6 wherein said pyrrolo[2,3-b]pyrroles are selected from the group consisting of 2,3-diamino-6H-pyrrolo[2,3-b]pyrrol-1-ol, 1-methoxy-1,6-dihydro-pyrrolo[2,3-b]pyrrole-2,3-diamine, 1-ethoxy-1,6-dihydro-pyrrolo[2,3-b]pyrrole-2,3-diamine, 2-(2,3-diamino-6H-pyrrolo[2,3-b]pyrrol-1-yloxy)-ethanol, 1-isopropoxy-1,6-dihydro-pyrrolo[2,3-b]pyrrole-2,3-diamine, 1-benzyloxy-1,6-dihydro-pyrrolo[2,3-b]pyrrole-2,3-diamine, 6H-pyrrolo[2,3-b]pyrrole-1,2,3-triamine, N1-methyl-6H-pyrrolo[2,3-b]pyrrole-1,2,3-triamine, N1-ethyl-6H-pyrrolo[2,3-b]pyrrole-1,2,3-triamine, 2-(2,3-diamino-6H-pyrrolo[2,3-b]pyrrol-1-ylamino)-ethanol, N1-isopropyl-6H-pyrrolo[2,3-b]pyrrole-1,2,3-triamine, and N1-benzyl-6H-pyrrolo[2,3-b]pyrrole-1,2,3-triamine.

14. The composition of claim 6 wherein said pyrrolo[2,3-b]pyrroles are selected from the group consisting of 6H-pyrrolo[2,3-b]pyrrole-1,3-diamine, N1-methyl-6H-pyrrolo[2,3-b]pyrrole-1,3-diamine, N1,N1-diethyl-6H-pyrrolo[2,3-b]pyrrole-1,3-diamine, 2-[(3-amino-6H-pyrrolo[2,3-b]pyrrol-1-yl)-(2-hydroxy-ethyl)-amino]-ethanol, N1-isopropyl-6H-pyrrolo[2,3-b]pyrrole-1,3-diamine, N1-benzyl-6H-pyrrolo[2,3-b]pyrrole-1,3-diamine, 6-methyl-6H-pyrrolo[2,3-b]pyrrole-1,4-diamine, 6N1,N1-triethyl-6H-pyrrolo[2,3-b]pyrrole-1,4-diamine, 2-(3-amino-6-methylamino-6H-pyrrolo[2,3-b]pyrrol-1-yl)-ethanol, 6-benzyl-N1-methyl-6H-pyrrolo[2,3-b]pyrrole-1,4-diamine, 1-amino-6-methyl-1,6-dihydro-pyrrolo[2,3-b]pyrrol-3-ol, 1-diethylamino-6-isopropyl-1,6-dihydro-pyrrolo[2,3-b]pyrrol-3-ol, 6-amino-1-methyl-1,6-dihydro-pyrrolo[2,3-b]pyrrol-3-ol, 6-diethylamino-1-methyl-1,6-dihydro-pyrrolo[2,3-b]pyrrol-3-ol, and 6-benzylamino-1-methyl-1,6-dihydro-pyrrolo[2,3-b]pyrrol-3-ol.

15. The composition of claim 6 wherein said furo[2,3-b]pyrroles are selected from the group consisting of 4,5-diamino-furo[2,3-b]pyrrol-6-ol, 6-methoxy-6H-furo[2,3-b]pyrrole-4,5-diamine, 6-ethoxy-6H-furo[2,3-b]pyrrole-4,5-diamine, 2-(4,5-diamino-furo[2,3-b]pyrrol-6-yloxy)-ethanol, 6-isopropoxy-6H-furo[2,3-b]pyrrole-4,5-diamine, and 6-benzyloxy-6H-furo[2,3-b]pyrrole-4,5-diamine.

16. The composition of claim 6 wherein said thieno[2,3-b]pyrroles are selected from the group consisting of 4,5-diamino-thieno[2,3-b]pyrrol-6-ol, 6-methoxy-6H-thieno[2,3-b]pyrrole-4,5-diamine, 6-ethoxy-6H-thieno[2,3-b]pyrrole-4,5-diamine, 2-(4,5-diamino-thieno[2,3-b]pyrrol-6-yloxy)-ethanol, 6-isopropoxy-6H-thieno[2,3-b]pyrrole-4,5-diamine, and 6-benzyloxy-6H-thieno[2,3-b]pyrrole-4,5-diamine.

17. The composition of claim 6 wherein said thieno[2,3-b]pyrroles are selected from the group consisting of 4-amino-thieno[2,3-b]pyrrol-6-ol, 6-methoxy-6H-thieno[2,3-b]pyrrol-4-ylamine, 6-ethoxy-6H-thieno[2,3-b]pyrrol-4-ylamine, 2-(4-amino-thieno[2,3-b]pyrrol-6-yloxy)-ethanol, thieno[2,3-b]pyrrole-4,6-diamine, N6-methyl-thieno[2,3-b]pyrrole-4,6-diamine, N6,N6-diethyl-thieno[2,3-b]pyrrole-4,6-diamine, and 2-[(4-amino-thieno[2,3-b]pyrrol-6-yl)-(2-hydroxy-ethyl)-amino]-ethanol.

18. The composition of claim 1 further comprising auxiliary developers.

19. The composition of claim 1 further comprising auxiliary couplers.

20. The composition of claim 1 further comprising direct dyes.

21. The composition of claim 1 further comprising at least one additional component selected from the group consisting of oxidizing agents, thickeners, chelants, pH modifiers, buffering agents, and carbonate ion source and radical scavenger systems.

22. A method of dyeing hair comprising the steps of
(a) applying the composition of claim 1; and
(b) rinsing hair.

23. A kit comprising
(a) the composition of claim 1;
(b) an oxidizing agent; and
(c) auxiliary couplers and/or auxiliary developers.

* * * * *